US007439373B2

(12) United States Patent
Molnar et al.

(10) Patent No.: US 7,439,373 B2
(45) Date of Patent: Oct. 21, 2008

(54) CRYSTALLINE MYCOPHENOLATE SODIUM

(75) Inventors: Sandor Molnar, Debrecen (HU); Csaba Szabo, Debrecen (HU); Tivadar Tamas, Debrecen (HU); Janos Hajko, Debrecen (HU); Adrienne Kovacsne-Mezei, Debrecen (HU); Judith Aronhime, Rehovot (IL)

(73) Assignee: TEVA Gyógyszergyár Zártkörúen Múködö Részvénytársaság, Debrecen (HU)

( * ) Notice: Subject to any disclaimer, the term of this patent is extended or adjusted under 35 U.S.C. 154(b) by 266 days.

(21) Appl. No.: 11/186,560

(22) Filed: Jul. 20, 2005

(65) Prior Publication Data
US 2006/0069152 A1    Mar. 30, 2006

Related U.S. Application Data

(60) Provisional application No. 60/631,849, filed on Nov. 29, 2004, provisional application No. 60/589,909, filed on Jul. 20, 2004.

(51) Int. Cl.
C07D 307/00     (2006.01)
C07D 413/00     (2006.01)
(52) U.S. Cl. .................................. 549/305; 544/153
(58) Field of Classification Search ................ 549/305; 544/153
See application file for complete search history.

(56) References Cited

U.S. PATENT DOCUMENTS

| | | | |
|---|---|---|---|
| 4,452,891 A | 6/1984 | Kida et al. | |
| 4,748,173 A | 5/1988 | Nelson et al. | |
| 4,753,935 A | 6/1988 | Nelson et al. | |
| 4,786,637 A | 11/1988 | Allison et al. | |
| 4,808,592 A | 2/1989 | Nelson et al. | |
| 4,861,776 A | 8/1989 | Nelson et al. | |
| 4,868,153 A | 9/1989 | Allison et al. | |
| 4,948,793 A | 8/1990 | Allison et al. | |
| 4,952,579 A | 8/1990 | Nelson et al. | |
| 5,247,083 A | 9/1993 | Knox et al. | |
| 5,455,045 A | 10/1995 | Samuels et al. | |
| 5,543,408 A | 8/1996 | Fu et al. | |
| 5,545,637 A | 8/1996 | Fu et al. | |
| 5,688,529 A | 11/1997 | Lidgate et al. | |
| 6,333,198 B1 | 12/2001 | Edmeades et al. | |
| 6,709,846 B1 | 3/2004 | Sircar et al. | |
| 2004/0167130 A1 | 8/2004 | Lee et al. | |

FOREIGN PATENT DOCUMENTS

| | | |
|---|---|---|
| EP | 0 281 713 | 9/1988 |
| EP | 0 963 980 | 12/1999 |
| GB | 1 157 099 | 7/1969 |
| GB | 1 158387 | 7/1969 |
| WO | WO 94/01427 | 1/1994 |
| WO | WO 97/38689 | 10/1997 |
| WO | WO 00/34503 | 6/2000 |
| WO | WO 01/21607 | 3/2001 |
| WO | WO 01/64931 | 9/2001 |
| WO | WO 02/100855 | 12/2002 |
| WO | WO 2004064806 | * 1/2004 |
| WO | WO 2004/020426 | 3/2004 |
| WO | WO 2004/064806 | 8/2004 |
| WO | WO 2004/087174 A1 | 10/2004 |
| ZA | 68/4959 | 11/1967 |

OTHER PUBLICATIONS

Rihs et al., "Metal-Organic Compounds: Sodium Mycophenolate", *Acta Crystallographic* 2000, C56, pp. 423-433.
Wrigglesworth et al. "Analogues of Capsaicin with Agonist Activity as Novel Analgesic Agents: Structure-Activity Studies", *Journal of Medicinal Chemistry*, 1996, pp. 4942-4951, vol. 39, No. 25.
Caira, "Crystalline Polymorphism of Organic Compounds", *Topics in Current Chemistry*, 1998, pp. 163-208, vol. 198.
Sadhukhan et al. "Optimization of Mycophenolic Acid Production in Solid State Fermentation Using Response Surface Methodology", *Journal of Industrial Microbiology and Biotechnology*, 1999, pp. 33-38, vol. 22, No. 1.
Makara et al. "Nuclear Magnetic Resonance and Molecular Modeling Study on Mcyophenolic Acid: Implications for Binding to Inosine Monophosphate Dehydrogenase", *Journal of Medicinal Chemistry*, 1996, pp. 1236-1242, vol. 39, No. 6+.
Abraham, "The Effect Of Mycophenolic Acid On The Growth Of *Staphylococcus aureus* In Heart Broth", *Biochem. J.*, 1945, pp. 398-408, vol. 39, No. 5.
Ando, et al., "Antiviral Activity Of Mycophenolic Acid Studies On Antiviral And Antitumor Antibiotics. IV", *The Journal of Antibiotics*, Aug. 19, 1968, pp. 649-652, vol. 21, No. 11.
Bentley, "Bartolomeo Gosio, 1863-1944: An Appreciation", *Advances In Applied Microbiology*, 2001, pp. 229-251, vol. 48.
Bentley, "Mycophenolic Acid: A One Hundred Year Odyssey From Antibiotic To Immunosuppressant", *Chem. Rev.* 2000, pp. 3801-3825, vol. 100, No. 10.
Guillory, "Polymorphism in Pharmaceutical Solids", *Drugs and the Pharmaceutical Sciences*, edited by Brittain, 1999, pp. 184-222, vol. 95. Marcel Dekker, Inc.
Clutterbuck, et al., "The Metabolic Products Of The Penicillium Brevi-Compactum Series", *Studies In The Biochemistry Of Micro-Organisms*, 1932, pp. 1441-1458.
Craig, et al., "The Relevance Of The Amorphous State To Pharmaceutical Dosage Forms: Glassy Drugs And Freeze Dried Systems", *International Journal of Pharmaceutics*, 1999, pp. 179-207, vol. 179.
Desrosiers, et al., "High Throughput Screening Techniques For Pre-Formulation: Salt Selection And Polymorph Studies", *Acta Cryst.*, 2002, A58 (Supplement), C9.
Filtenborg, et al., "Simple Screening Method For Molds Producing Intracellular Mycotoxins In Pure Cultures", *Applied and Environmental Microbiology*, Feb. 1983, pp. 581-585, vol. 45, No. 2.

(Continued)

*Primary Examiner*—D. Margaret Seaman
*Assistant Examiner*—Nizal S Chandrakumar
(74) *Attorney, Agent, or Firm*—Kenyon & Kenyon LLP

(57) ABSTRACT

Provided are crystalline mycophenolate sodium forms and processes for their preparation.

4 Claims, 76 Drawing Sheets

OTHER PUBLICATIONS

Franklin, et al., "The Inhibition Of Nucleic Acid Synthesis By Mycophenolic Acid", *Biochem. J.*, 1969, pp. 515-524, vol. 113.

Frisvad, et al., "Classification Of *Terverticillate penicilla* Based On Profiles Of Mycotoxins And Other Secondary Metabolites", *Applied and Environmental Microbiology*, 1983, pp. 1301-1310, vol. 46, No. 6.

Gainer, et al., "GLC Of Mycophenolic Acid And Related Compounds", *Journal of Pharmaceutical Sciences*, 1970, pp. 1157-1159, vol. 59, No. 8.

Gilliver, "The Inhibitory Action Of Antibiotics On Plant Pathogenic Bacteria And Fungi", *Annals of Botany, N.S.*, 1946, pp. 271-282, vol. 10, No. 39.

Gosio, "Sur La Reconnaissance De L'Arsenic, Au Moyen De Certaines Moisissures", *Archives Italiennes De Biologie*, 1893, pp. 299-305.

Gu, et al., "Grouping Solvents By Statistical Analysis Of Solvent Property Parameters: Implication To Polymorph Screening", *International Journal of Pharmaceutics*, 2004, pp. 117-125, vol. 283.

Gu, et al., "Polymorph Screening: Influence Of Solvents On The Rate Of Solvent-Mediated Polymorphic Transformation", *Journal of Pharmaceutical Sciences*, 2001, pp. 1878-1890, vol. 90, No. 11.

Hilfiker, et al., "Polymorphism—Integrated Approach From High-Throughput Screening To Crystallization Optimization", *Journal of Thermal Analysis and Calorimetry*, 2003, pp. 429-440, vol. 73.

Makara, et al., "Nuclear Magnetic Resonance And Molecular Study On Mycophenolic Acid: Implications For Binding To Monophosphate Dehydrogenase", *Journal of Medicinal Chemistry*, 1996, pp. 1236-1242, vol. 39, No. 6.

Noto, et al., "Some Biological Properties Of Mycophenolic Acid", *The Journal of Antibiotics*, 1969, pp. 165-169, vol. 22, No. 4.

Nowak, et al., "Mycophenolic Acid Binding To Human Serum Albumin: Characterization And Relation To Pharmacodynamics", *Clinical Chemistry*, 1995, pp. 1011-1017, vol. 41, No. 7.

Rihs, et al., "Sodium Mycophenolate", *Acta Crystallographica*, 2000, pp. 432-433, vol. C56.

Snyder, et al., *Introduction To Modern Liquid Chromatography, 2nd Ed.*, 1979, pp. 549-572, John Wiley & Sons, Inc.

Sollinger, Hans W., "Mycophenolate Mofetil", *Kidney International*, 1995, pp. S-14-S-17, vol. 48, Suppl. 52.

Strobel, et al., *Chemical Instrumentation: A Systematic Approach, 3rd Ed.*, 1989, pp. 391-393, 879-894, 922-925, 953.

Wagner, et al., "Carboxylic Esters", *Synthetic Organic Chemistry*, 1953, pp. 479-531.

Wiwattanawongsa, et al., "Determination Of Mycophenolic Acid And Its Phenol Glucuronide Metabolite In Human Plasma And Urine By High-Performance Liquid Chromatography", *Journal of Chromatography B*, 2001, pp. 35-45, vol. 763.

\* cited by examiner

Characteristic XRD pattern of Form M1.

Characteristic FT-IR spectrum of Form M1

FIG. 3 Characteristic XRD pattern of Form M2.

Characteristic FT-IR spectra of Form M2

Characteristic XRD pattern of form M4.

FIG. 8 Characteristic XRD pattern of form M5

Characteristic XRD pattern of form M7

Characteristic XRD pattern of form M8.

Characteristic XRD pattern of Form M9.

Characteristic XRD pattern of form M10.

Characteristic XRD pattern of Form M11.

Characteristic FT-IR spectra of Form M12.

FIG. 17 Characteristic XRD pattern of Form D1.

Characteristic FT-IR spectra of Form D1.

Characteristic XRD pattern of Form D2.

FIG.20 Characteristic XRD diffractogram of Mycophenolate Monosodium form M15

FIG.24 Characteristic XRD diffractogram of Mycophenolate Monosodium form M19

Characteristic FT-IR spectrum of Mycophenolate Monosodium form M15

Characteristic FT-IR spectrum of Mycophenolate Monosodium form M16

Characteristic FT-IR spectrum of Mycophenolate Monosodium form M18

Characteristic FT-IR spectrum of Mycophenolate Monosodium form M20

Characteristic FT-IR spectrum of Mycophenolate Monosodium form M21

Characteristic DSC curve of form M2.

FIG.44 Characteristic DSC curve of form M3.

Characteristic DSC curve of form M4

Characteristic DSC curve of form M7

Characteristic DSC curve of form M8

Characteristic DSC curve of form M9

Characteristic DSC curve of form M10

FIG. 52 Characteristic DSC curve of form M11

Characteristic DSC curve of form M12

Characteristic DSC curve of Mycophenolate Monosodium form M15

FIG.55 Characteristic DSC curve of Mycophenolate Monosodium form M16

FIG.56 Characteristic DSC curve of Mycophenolate Monosodium form M17

FIG.57 Characteristic DSC curve of Mycophenolate Monosodium form M18

FIG.58 Characteristic DSC curve of Mycophenolate Monosodium form M19

FIG. 59 Characteristic DSC curve of Mycophenolate Monosodium form M20

Characteristic DSC curve of Mycophenolate Monosodium form M26

Characteristic DSC curve of Mycophenolate Monosodium form M27

FIG.64 Characteristic DSC curve of Mycophenolate Monosodium form M28

Calculated XRD pattern of single crystal data of Article Acta Christallographica Sect. C, (2000), C56,432-434

FIG.70 Characteristic TGA curve of Mycophenolate Monosodium form M19

Characteristic TGA curve of Mycophenolate Monosodium form M26

FIG. 75 Characteristic TGA curve of Mycophenolate Monosodium form M27

CRYSTALLINE MYCOPHENOLATE SODIUM

CROSS-REFERENCE TO RELATED APPLICATIONS

This application claims the benefits of U.S. Provisional Patent Application Nos. 60/589,909, filed Jul. 20, 2004, and 60/631,849 filed Nov. 29, 2004, the contents of all of which are incorporated herein by reference.

FIELD OF THE INVENTION

The present invention relates to the solid state chemistry of mycophenolate sodium.

BACKGROUND OF THE INVENTION

At the end of 1960's, Eli Lilly disclosed the inhibiting effect of mycophenolate sodium salt (MPS) on the growth of malignant tumor cells in warm-blooded mammals. Nowadays Novartis has introduced an enteric-coated formulation of mycophenolate sodium, referred to as Myfortic®. Mycophenolic acid can be formed either as mono- or disodium salt. South African patent No. 6804959 describes the preparation of mono- and disodium mycophenolate. Monosodium mycophenolate can be isolated after reaction of one molar equivalent of sodium methoxide with mycophenolic acid in a mixture of methanol and chloroform by precipitation with n-pentane. Preparation of the corresponding disodium salt is also described. In this case two molar equivalents of sodium methoxide were added to a solution of mycophenolic acid in 2:1 benzene-chloroform mixture. The evaporated material was crystallized from aqueous acetone.

The synthetic route of WO 97/38689 is identical to the one described in South African patent No. 6804959. The compound may be obtained in crystalline form by recrystallization from acetone/ethanol if necessary with water (m.p. 189-191° C.).

The present invention relates to the solid state physical properties of mycophenolate sodium. These properties may be influenced by controlling the conditions under which mycophenolate sodium is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid may have therapeutic consequences since it imposes an upper limit on the rate at which an orally-administered active ingredient may reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic Form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetry (DSC) and may be used to distinguish some polymorphic forms from others. A particular polymorphic form may also give rise to distinct spectroscopic properties that may be detectable by powder X-ray crystallography, solid state C NMR spectrometry and infrared spectrometry.

WO2004/020426 discloses preparation of sodium mycophenolate by reacting mycophenolic acid or its ammonium or dibenzyl-amine salt with a sodium salt of $C_2$ to $C_{10}$ carboxylic acid. Mycophenolic acid is converted to its ammonium salt by reacting with ammonia. This compound is reacted with sodium acetate to obtain the sodium salt of mycophenolic acid.

WO 2004/064806 discloses additional polymorphic forms of mycophenolate sodium and acid.

Monosodium Salt

South African patent No. 68/4,959 provides an example for preparing monosodium mycophenolate salt (Example 3). Sodium methylate in anhydrous methanol was added to mycophenolic acid in chloroform, then the monosodium salt was precipitated by adding n-pentane and collected by filtration and vacuum dried.

Acta Chrtystallographica Sect. C, (2000), C56, 432-433 describes another process for producing monosodium mycophenolate. A methanolic solution of the commercially available mycophenolic acid was treated with one equivalent of sodium methanolate. After stirring for 1 hour at room temperature, the solvent was evaporated to dryness in vacuum. The melting point of the product was 463 K (190° C.). Single crystals were grown by evaporation and cooling of a water/ethyl acetate solution from about 323K to room temperature. The crystal structure of the produced sodium mycophenolate measured by single crystal diffractometer is also described.

Based on the given crystal parameters, the calculated powder diffractogram done by the inventors of the present invention show that the crystal form obtained is the crystal form denominated Form M2. Form M2 is an anhydrous form. Form M2 is characterized by a powder XRD pattern with peaks at 5.3, 8.0, 9.8, 10.7, and 21.9±0.2 degrees 2 theta (FIG. 3) and FTIR peaks at 1719, 1571, 1317, 1266, 1134 and 927 cm-1 (FIG. 4). Form M2 may be further characterized by XRD peaks at 13.6 and 19.0±0.2 degrees 2 theta. Form M2 may be further characterized by IR peaks at 1194, 1108, 1075, 1034, 971, 875, 826, 794 and 722 cm-1. Form M2 may be further characterized by a DSC curve (FIG. 43).

PCT 97/38689 describes sodium mycophenolate salts as known from South African Patent. It also describes the process for obtaining monosodium salt in crystalline form by recrystallization from acetone/ethanol if necessary with water. The melting point provided is 189-191° C.

J. Med. Chem. (1996), 39, 1236-1242 describes treating a solution of mycophenolic acid in ethanol with equimolar sodium ethylate at room temperature and stirring for 30 minutes. The solvent was evaporated in vacuum.

J. Pharm. Sciences (1970), 59(8), 1157-1159 asserts that monosodium mycophenolate may be formed by adjusting the slurry of mycophenolic acid to pH 7-8 with sodium hydroxide. No physical data is provided.

Disodium Salt

South African patent No. 68/4,959 provides an example for producing disodium mycophenolate (Example 2). Mycophenolic acid was dissolved in benzene:chloroform 2:1 solvent mixture and sodium methoxide dissolved in anhydrous methanol was added to it. The solution was stirred for 15-20 minutes, evaporated to dryness and redissolved in water.

Crystallization was effected by the addition of acetone to the hot water solution and chilling overnight. No physical data was given.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

SUMMARY OF THE INVENTION

The invention encompasses crystalline forms of monosodium mycophenolate denominated forms M1, M3, M4, M5, M6, M7, M8, M9, M10, M11, M15, M16, M17, M18, M19, M20, M21, M22, M26, M27 and M28, amorphous mycophenolate monosodium M12, crystalline disodium mycophenolate forms D1 and D2, and preparations thereof. The invention also encompasses pharmaceutical compositions comprising any one of the mycophenolate forms of the invention.

The present invention provides for mycophenolate sodium hydrates. The mycophenolate sodium hydrates of this invention may be mycophenolate sodium monohydrates. The mycophenolate sodium monohydrates of this invention may be further characterized by water content of about 3.5% to about 5%. Mycophenolate sodium Forms M1 and M9 discussed below are mycophenolate sodium monohydrates. Mycophenolate sodium M16, M17, M18 and M22 discussed below are mycophenolate sodium hydrates.

The present invention provides for anhydrous mycophenolate sodium. The anhydrous mycophenolate sodium of this invention may be further characterized by having not more than 1% weight loss. Mycophenolate sodium Forms M3 and M5 discussed below are anhydrous mycophenolate sodium.

The present invention provides for mycophenolate sodium solvates. The mycophenolate sodium solvates of this invention may be mycophenolate sodium monosolvates. Mycophenolate sodium Forms M4, M6, M7, M10, M11, M8, M15, M19, M20, M21, M26, M27 and M28 discussed below are mycophenolate sodium solvates.

The present invention provides for mycophenolate sodium acetone solvate. The mycophenolate sodium acetone solvate of this invention may be mycophenolate sodium monoacetone solvate of 1:1 ratio. The mycophenolate sodium acetone solvate 1:1 of this invention may be further characterized by acetone content of about 14% to about 18%. Mycophenolate sodium Form M6 discussed below is a acetone solvated form of 1:1 ratio.

The present invention provides for mycophenolate sodium acetonitrile solovate. The mycophenolate sodium acetonitrile solvate of this invention may be mycophenolate sodium acetonitrile solvate of 1:1 ratio. The mycophenolate sodium acetonitrile solvate of this invention may be further characterized by acetonitrile content of about 9.5% to about 11.5%. Mycophenolate sodium Form M10 discussed below is a acetonitrile solvated form of 1:1 ratio.

The present invention provides for amorphous mycophenolate sodium. Mycophenolate sodium Form M12 discussed below is an amorphous form.

In one embodiment, the present invention encompasses a crystalline mycophenolate sodium, denominated Form M1, characterized by a powder XRD pattern with peaks at 4.7, 6.6, 11.2 and 15.6±0.2 degrees 2 theta (FIG. 1). Form M1 may be further characterized by XRD peaks at 8.2, 21.5 and 23.4±0.2 degrees 2 theta. Form M1 may also be characterized by FTIR peaks at 3450, 1723, 1619, 1578, 1268 and 1132 cm-1 (FIG. 2). In addition, Form M1 may be characterized by DSC peaks as shown in FIG. 42.

One process for preparing crystalline mycophenolate sodium M1 comprises preparing a solution of mycophenolic acid in a $C_1$-$C_4$ alcohol; combining a base and a source of sodium with the solution to form a mixture; cooling the mixture to precipitate the crystalline form and recovering the crystalline form before transition to another crystalline form. Stirring is preferably carried out for about 1 to about 5 hours.

Another process for preparing crystalline mycophenolate sodium M1 comprises dissolving sodium mycophenolate in water; crystallizing the crystalline form; and recovering the crystalline form.

Another process for preparing crystalline mycophenolate sodium M1 comprises preparing a solution of sodium mycophenolate in ethanol; crystallizing the crystalline form from the solution; and recovering the crystalline form.

Another process for preparing crystalline mycophenolate sodium M1 comprises contacting crystalline mycophenolate sodium with water vapor.

The present invention encompasses crystalline mycophenolate sodium, denominated Form M3, characterized by a powder XRD pattern with peaks at 6.0, 9.3, 15.5, and 18.4±0.2 degrees 2 theta (FIG. 5) and FTIR peaks at 3414, 1713, 1618, 1567, 1264 and 1134 cm-1 (FIG. 6). Form M3 may be further characterized by a powder XRD pattern with peaks at 7.2, 10.8, 13.8, and 24.0±0.2 degrees 2 theta. In addition, Form M3 may be characterized by DSC peaks as shown in FIG. 44.

The process for preparing crystalline mycophenolate sodium M3 comprises the steps of: preparing a solution of mycophenolic acid in a $C_1$ to $C_4$ alcohol, preferably methanol; combining a base and a source of sodium with the solution to form a mixture; cooling the mixture to crystallize the crystalline form and recovering the crystalline form. The crystalline form is preferably dried.

The present invention is a crystalline mycophenolate sodium, denominated Form M4, characterized by a powder XRD pattern with peaks at 7.1, 7.6, 10.7, 14.0 and 16.3±0.2 degrees 2 theta (FIG. 7). Form M4 may be further characterized by XRD peaks at 5.4, 19.7 and 20.2±0.2 degrees 2 theta. In addition, Form M4 may be characterized by DSC peaks as shown in FIG. 45.

The process for preparing crystalline mycophenolate sodium M4 comprises the steps of: preparing a solution of mycophenolic acid in methanol; combining a base and a source of sodium with the solution to form a mixture; cooling the mixture to crystallize the crystalline form; and recovering the crystalline form.

The present invention is a crystalline mycophenolate sodium, denominated Form M5, characterized by a powder XRD pattern with peaks at 9.8, 17.4, 22.2, 27.1, and 31.7±0.2 degrees 2 theta (FIG. 8). Form M5 may be further characterized by XRD peaks at 21.0, 26.3 and 31.4±0.2 degrees 2 theta. In addition, Form M5 may be characterized by DSC peaks as shown in FIG. 46.

The process for preparing crystalline mycophenolate sodium M5 comprises the steps of: preparing a mixture of sodium mycophenolate and 1,4-dioxane; crystallizing the crystalline form from the mixture; and recovering the crystalline form.

The present invention is a crystalline mycophenolate sodium, denominated Form M6, characterized by a powder XRD pattern with peaks at 6.1, 7.9, 14.6, 18.2 and 18.5±0.2 degrees 2 theta (FIG. 9). Form M6 may be further characterized by XRD peaks at 21.0 and 22.5±0.2 degrees 2 theta. In addition, Form M6 may be characterized by DSC peaks as shown in FIG. 47.

The process for preparing crystalline mycophenolate sodium M6 comprises the steps of: preparing a solution of sodium mycophenolate in water; combining a $C_3$ to $C_7$ ketone with the solution to precipitate the crystalline form; and recovering the crystalline form.

The present invention is a crystalline mycophenolate sodium, denominated Form M7, characterized by a powder XRD pattern with peaks at 13.0, 13.7, 17.6, 22.6, and 23.6±0.2 degrees 2 theta (FIG. 10). Form M7 may be further characterized by XRD peaks at 9.6, 12.6, 19.2, 23.2 and 27.4±0.2 degrees 2 theta. In addition, Form M7 may be characterized by DSC peaks as shown in FIG. 48.

The process for preparing crystalline mycophenolate sodium M7 comprises the steps of: preparing a solution of sodium mycophenolate in dimethylformamide; combining a $C_3$ to $C_7$ ketone with the solution to precipitate the crystalline form; and recovering the crystalline form.

The present invention is a crystalline mycophenolate sodium, denominated Form M8, characterized by a powder XRD pattern with peaks at 5.4, 7.5, 9.8, 10.6, 18.2 and 20.9±0.2 degrees 2 theta (FIG. 11). Form M8 may be further characterized by XRD peaks at 8.1, 11.7 and 15.9±0.2 degrees 2 theta. In addition, Form M8 may be characterized by DSC peaks as shown in FIG. 49.

The process for preparing crystalline mycophenolate sodium M8 comprises the steps of: preparing a solution of sodium mycophenolate in ethyl lactate; combining ethyl acetate with the solution to precipitate the crystalline form; and recovering the crystalline form.

The present invention is a crystalline mycophenolate sodium, denominated M9, characterized by a powder XRD pattern with peaks at 5.6, 6.0, 7.5 and 9.9±0.2 degrees 2 theta (FIG. 12). Form M9 may be further characterized by XRD peaks at 5.1, 11.9, 13.7, 16.4 and 19.1±0.2 degrees 2 theta. In addition, Form M9 may be characterized by DSC peaks as shown in FIG. 50.

The process for preparing crystalline mycophenolate sodium M9 comprises the steps of: preparing a solution of sodium mycophenolate in a $C_1$ to $C_4$ alcohol; combining methylene chloride with the solution to precipitate the crystalline form; and recovering the crystalline form.

The present invention is a crystalline mycophenolate sodium, denominated Form M10, characterized by a powder XRD pattern with peaks at 5.8, 9.0, 9.3, and 19.7±0.2 degrees 2 theta (FIG. 13). Form M10 may be further characterized by XRD peaks at 5.1, 11.8, 15.5 17.3, and 18.6±0.2 degrees 2 theta. In addition, Form M10 may be characterized by DSC peaks as shown in FIG. 51.

The process for preparing crystalline mycophenolate sodium M10 comprises the steps of: preparing a solution of mycophenolic acid in acetonitrile; combining a base and a source of sodium with the solution to precipitate the crystalline form; and recovering the crystalline form.

The present invention is a crystalline mycophenolate sodium, denominated Form M11, characterized by a powder XRD pattern with a peak 10.3±0.2 degrees 2 theta (FIG. 14). Form M11 may be further characterized by XRD peaks at 4.7, 5.3, 6.5, 8.2, 9.9, 15.5 and 19.1±0.2 degrees 2 theta. In addition, Form M11 may be characterized by DSC peaks as shown in FIG. 52.

The process for preparing crystalline mycophenolate sodium M11 comprises the steps of: preparing a solution of mycophenolic acid in acetonitrile; combining a base and a source of sodium with the solution to form a precipitate; recovering the precipitate; and drying the crystalline form.

The present invention is amorphous mycophenolate sodium, denominated M12, characterized by FTIR peaks at 1735, 1560 and 1133 cm-1 (FIG. 16). Form M12 may be further characterized by FTIR peaks at 1192, 1164, 1074, 1031, 969 and 722 cm-1. In addition, Form M12 may be characterized by DSC peaks as shown in FIG. 53.

The process for preparing amorphous mycophenolate sodium M12 comprises the steps of: preparing a solution of sodium mycophenolate in water; and lyophilizing the solution to obtain the crystalline form.

The invention encompasses a crystalline mycophenolate sodium, denominated Form M15, characterized by data selected from at least one of a powder XRD pattern (FIG. 20) with peaks at 9.9, 13.1, 14.1, 16.1, 17.7, 18.5, 19.6, and 23.8±0.2 degrees 2-theta or an FTIR spectrum (FIG. 31) with peaks at 3434, 1727, 1650, 1609, 1561, 1326, 1277, 1194, 1139, 965, 858, 830, 799, 763, 723, 666 and 1132 cm$^{-1}$. In addition, Form M15 may be characterized by DSC peaks as shown in FIG. 54.

The invention also provides a process for preparing crystalline mycophenolate sodium M15 comprising the steps of: preparing a mixture of sodium mycophenolate in 1,4-dioxane; heating the mixture; cooling the mixture to precipitate the crystalline form; and recovering the crystalline form. Preferably, the ratio of 1,4-dioxane to sodium mycophenolate is less than about 100 ml/g. More preferably, the ratio of 1,4-dioxane to sodium mycophenolate is less than about 50 ml/g.

The invention encompasses a crystalline mycophenolate sodium, denominated Form M16, characterized by data selected from at least one of a powder XRD pattern (FIG. 21) with peaks at 5.2, 5.5, 8.1, 11.0, 16.1, 16.6, 17.3, and 22.0±0.2 degrees 2-theta or an FTIR spectrum (FIG. 32) with peaks at 3436, 1721, 1685, 1654, 1614, 1552, 1320, 1275, 1253, 1219, 1133, 1111, 1080, 1038, 975, 878, 807, 778, and 722 cm$^{-1}$. In addition, Form M16 may be characterized by DSC peaks as shown in FIG. 55.

The invention also provides a process for preparing crystalline mycophenolate sodium M16 comprising the steps of: preparing a mixture of sodium mycophenolate in 4-methyl-2-pentanone; heating the mixture; cooling the mixture to precipitate the crystalline form; and recovering the crystalline form.

The invention encompasses a crystalline mycophenolate sodium, denominated Form M17, characterized by data selected from at least one of a powder XRD pattern (FIG. 22) with peaks at 5.5, 7.7, 8.1, 9.8, 10.7, 11.0, 16.5, 22.0, and 26.0±0.2 degrees 2-theta or an FTIR spectrum (FIG. 56) with peaks at 3470, 1722, 1650, 1608, 1560, 1254, 1083, 1040, 974, and 772 cm$^{-1}$. In addition, Form M17 may be characterized by DSC peaks as shown in FIG. 56.

The invention also provides a process for preparing crystalline mycophenolate sodium M17 comprising the steps of: preparing a mixture of sodium mycophenolate in dimethylcarbonate; heating the mixture; cooling the mixture to precipitate the crystalline form; and recovering the crystalline form.

The invention encompasses a crystalline mycophenolate sodium, denominated Form M18, characterized by data selected from at least one of a powder XRD pattern (FIG. 23) with peaks at 5.6, 8.1, 9.9, 10.8, 13.7, 16.6, 19.1, and 22.1±0.2 degrees 2-theta or an FTIR spectrum (FIG. 34) with peaks at 3449, 1723, 1686, 1614, 1552, 1320, 1253, 1134, 1110, 1078, 1036, 974, 879, 856, 831, 808, 764, and 722 cm$^{-1}$. In addition, Form M18 may be characterized by DSC peaks as shown in FIG. 57.

The invention also provides a process for preparing crystalline mycophenolate sodium M18 comprising the steps of: preparing a mixture of sodium mycophenolate in 2-methyl-2-propanol; heating the mixture; cooling the mixture to precipitate the crystalline form; and recovering the crystalline form.

One embodiment of the invention encompasses a crystalline mycophenolate sodium, denominated Form M19, characterized by data selected from at least one of a powder XRD pattern (FIG. 24) with peaks at 7.6, 8.3, 10.7, 11.7, 15.9, 18.2, 21.0, and 21.6±0.2 degrees 2-theta or an FTIR spectrum (FIG. 35) with peaks at 3422, 1710, 1569, 1264, 1190, 1133, 1111, 1074, 1032, 971, 943, 918, 864, 829, 796, and 722 cm$^{-1}$. In addition, Form M19 may be characterized by DSC peaks as shown in FIG. 58.

The invention also provides a process for preparing crystalline mycophenolate sodium M19 comprising the steps of: preparing a solution of sodium mycophenolate in a $C_1$ to $C_4$ alcohol, preferably methanol; combining carbon tetrachloride with the solution to precipitate the crystalline form; and recovering the crystalline form.

The invention encompasses a crystalline mycophenolate sodium, denominated Form M20, characterized by data selected from at least one of a powder XRD pattern (FIG. 25) with peaks at 5.1, 5.5, 6.7, 10.0, 10.9, 13.1, 14.6, 17.3, and 24.8±0.2 degrees 2-theta or an FTIR spectrum (FIG. 36) with peaks at 1731, 1694, 1618, 1588, 1568, 1405, 1262, 1204, 1164, 1136, 1111, 1081, 1033, 974, 948, 922, 870, 790, 764, and 722 cm$^{-1}$. In addition, Form M20 may be characterized by DSC peaks as shown in FIG. 59.

The invention also provides a process for preparing crystalline mycophenolate sodium M20 comprising the steps of: preparing a solution of sodium mycophenolate in N,N-dimethyl-acetamide; combining acetonitrile with the solution to precipitate the crystalline form; and recovering the crystalline form.

The invention encompasses a crystalline mycophenolate sodium, denominated Form M21, characterized by data selected from at least one of a powder XRD pattern (FIG. 26) with peaks at 5.4, 6.2, 7.9, 8.7, 8.9, 16.8, 20.0, and 25.2±0.2 degrees 2-theta or an FTIR spectrum (FIG. 37) with peaks at 3488, 1720, 1615, 1550, 1403, 1323, 1288, 1260, 1208, 1137, 1114, 1084, 979, 927, 869, 812, and 722 cm$^{-1}$. In addition, Form M21 may be characterized by DSC peaks as shown in FIG. 60.

The invention also provides a process for preparing crystalline mycophenolate sodium M21 comprising the steps of: preparing a mixture of sodium mycophenolate in a mixture of 1,4-dioxane and water to obtain a solution; combining 1,4-dioxane with the solution to precipitate the crystalline form; and recovering the crystalline form.

The invention encompasses a crystalline mycophenolate sodium, denominated Form M22, characterized by data selected from at least one of a powder XRD pattern (FIG. 27) with peaks at 3.8, 4.7, 5.3, 6.6, 8.1, 9.8, 10.6, 11.1, 15.5, and 23.3±0.2 degrees 2-theta or an FTIR spectrum (FIG. 38) with peaks at 3432, 1748, 1720, 1618, 1564, 1414, 1268, 1192, 1134, 1107, 1077, 1031, 971, 949, 875, 824, 794, and 723 cm$^{-1}$. In addition, Form M22 may be characterized by DSC peaks as shown in FIG. 61.

The invention also provides a process for preparing crystalline mycophenolate sodium M22 comprising the steps of: preparing a solution of mycophenolic acid in dichloromethane; combining a base and a source of sodium with the solution to precipitate the crystalline form; and recovering the crystalline form. A second portion of dichloromethane may be added after addition of the base.

The base and the source of sodium as used in this invention can be different, or they can be the same. For example, sodium methoxide, sodium ethoxide, or sodium hydroxide can be used as both the base and the source of sodium.

One embodiment of the invention encompasses a crystalline mycophenolate sodium, denominated Form M26, characterized by data selected from at least one of a powder XRD pattern (FIG. 28) with peaks at 5.8, 9.2, 9.5, 10.0, 13.4, 13.7, 15.8, 17.6, 23.6, and 24.1±0.2 degrees 2-theta or an FTIR spectrum (FIG. 39) with peaks at 1741, 1612, 1584, 1316, 1272, 1256, 1219, 1195, 1134, 1122, 1104, 1083, 1032, 966, 874, 794, 722, and 679 cm$^{-1}$. In addition, Form M26 may be characterized by DSC peaks as shown in FIG. 62.

The invention also provides a process for preparing crystalline mycophenolate sodium M26 comprising the steps of: preparing a solution of mycophenolic acid in 1,4-dioxane; combining a base and a source of sodium with the solution to form a mixture to precipitate the crystalline form; and recovering the crystalline form.

The invention encompasses a crystalline mycophenolate sodium, denominated Form M27, characterized by data selected from at least one of a powder XRD pattern (FIG. 29) with peaks at 6.2, 9.4, 12.6, 13.1, 13.7, 14.0, 15.9, 17.5, and 24.1±0.2 degrees 2-theta or an FTIR spectrum (FIG. 40) with peaks at 1727, 1593, 1327, 1275, 1221, 1195, 1139, 1114, 1082, 1031, 965, 874, 798, 763, 723, and 666 cm$^{-1}$. In addition, Form M27 may be characterized by DSC peaks as shown in FIG. 63.

The invention also provides a process for preparing crystalline mycophenolate sodium M27 comprising the steps of: preparing a solution of mycophenolic acid in 1,4-dioxane; combining a base and a source of sodium with the solution to precipitate the crystalline form; recovering the precipitate; and drying the precipitate to obtain the crystalline form.

The invention encompasses a crystalline mycophenolate sodium, denominated Form M28, characterized by data selected from at least one of a powder XRD pattern (FIG. 30) with peaks at 7.7, 8.5, 9.9, 12.3, 16.0, 21.4, 23.2, and 26.0±0.2 degrees 2-theta or an FTIR spectrum (FIG. 41) with peaks at 1730, 1696, 1612, 1588, 1570, 1403, 1301, 1263, 1194, 1165, 1135, 1109, 1079, 1033, 973, 948, 869, 832, 791, 763, and 723 cm$^{-1}$. In addition, Form M28 may be characterized by DSC peaks as shown in FIG. 64.

The invention also provides a process for preparing crystalline mycophenolate sodium M28 comprising the steps of: preparing a solution of mycophenolic acid in carbon-tetrachloride; combining a base and a source of sodium with the solution to preciptiate the crystalline form; and recovering the crystalline form.

The present invention is a crystalline disodium mycophenolate, denominated Form D1, characterized by a powder XRD pattern with peaks at 5.5, 8.1, 11.0, 16.5, and 26.0±0.2 degrees 2 theta (FIG. 17) and FTIR peaks at 3344 and 1552 cm-1 (FIG. 18). Form D1 may be further characterized by an XRD peak at 22.1±0.2 degrees 2 theta. Form D1 may be even further characterized by FTIR peaks at 1723, 1614, 1254 and 1133 cm-1.

The process for preparing crystalline mycophenolate disodium D1 comprising the steps of: preparing a solution of sodium carbonate in mycophenolic acid and methanol; concentrating the solution; precipitating the crystalline form; and recovering the crystalline form.

The present invention is a crystalline disodium mycophenolate, denominated Form D2, characterized by a powder XRD pattern with peaks at 6.2, 8.0, 18.3, 18.5 and 25.3±0.2 degrees 2 theta (FIG. 19). Form D2 may be further characterized by XRD peaks at 22.6 and 23.3±0.2 degrees 2 theta.

The process for preparing crystalline mycophenolate disodium D2 comprising the steps of: preparing a solution of mycophenolic acid in dichloromethane and toluene; combining a base and a source of sodium with the solution to form a mixture; concentrating the mixture into a residue; combining acetone and water with the residue to form a precipitate; and recovering the crystalline mycophenolate disodium from the precipitate.

The process for preparing crystalline mycophenolate disodium D2 comprising contacting crystalline mycophenolate sodium with water vapor.

The present invention encompasses pharmaceutical compositions comprising therapeutically effective amounts of any one of the mycophenolate sodium Form M1, M3 M4, M5, M6, M7, M8, M9, M10, M11, M12, M15, M16, M17, M18, M19, M20, M21, M22, M26, M27 or M28, or disodium mycophenolate Form D1 or D2, and at least one pharmaceutically acceptable carrier.

DETAILED DESCRIPTION OF THE INVENTION

The present invention provides polymorphic forms of mycophenolate monosodium, including hydrates, anhydrates and solvates. More specifically, the invention encompasses crystalline forms of monosodium mycophenolate denominated forms M1, M3, M4, M5, M6, M7, M8, M9, M10, M11, M15, M16, M17, M18, M19, M20, M21, M22, M26, M27 and M28, amorphous mycophenolate monosodium M12, crystalline disodium mycophenolate forms D1 and D2, and preparations thereof. The invention also encompasses pharmaceutical compositions comprising any one of the mycophenolate forms of the invention.

The mycophenolate sodium monohydrates of this invention may be characterized by water content of about 3.5% to about 5% by weight. Mycophenolate sodium Forms M1 and M9 discussed below are mycophenolate sodium monohydrates. Mycophenolate sodium M16, M17, M18 and M22 discussed below are mycophenolate sodium hydrates.

The anhydrous mycophenolate sodium of this invention may be characterized by having not more than 1% weight loss. Mycophenolate sodium Forms M3 and M5 discussed below are anhydrous mycophenolate sodium.

The mycophenolate sodium solvates of this invention may be mycophenolate sodium monosolvates. Mycophenolate sodium Forms M4, M6, M7, M10, M11, M8, M15, M19, M20, M21, M26, M27 and M28 discussed below are mycophenolate sodium solvates.

The mycophenolate sodium of this invention may be mycophenolate sodium acetone solvate of 1:1 ratio. The mycophenolate sodium acetone solvate of this invention may be further characterized by acetone content of about 14% to about 18%. Mycophenolate sodium Form M6 discussed below is a acetone solvated form of 1:1 ratio.

The mycophenolate sodium of this invention may be mycophenolate sodium acetonitrile solvate of 1:1 ratio. The mycophenolate sodium acetonitrile solvate of this invention may be further characterized by acetonitrile content of about 9.5% to about 11.5%. Mycophenolate sodium Form M10 discussed below is a acetonitrile solvated form of 1:1 ratio.

Form M1

Figure 1:
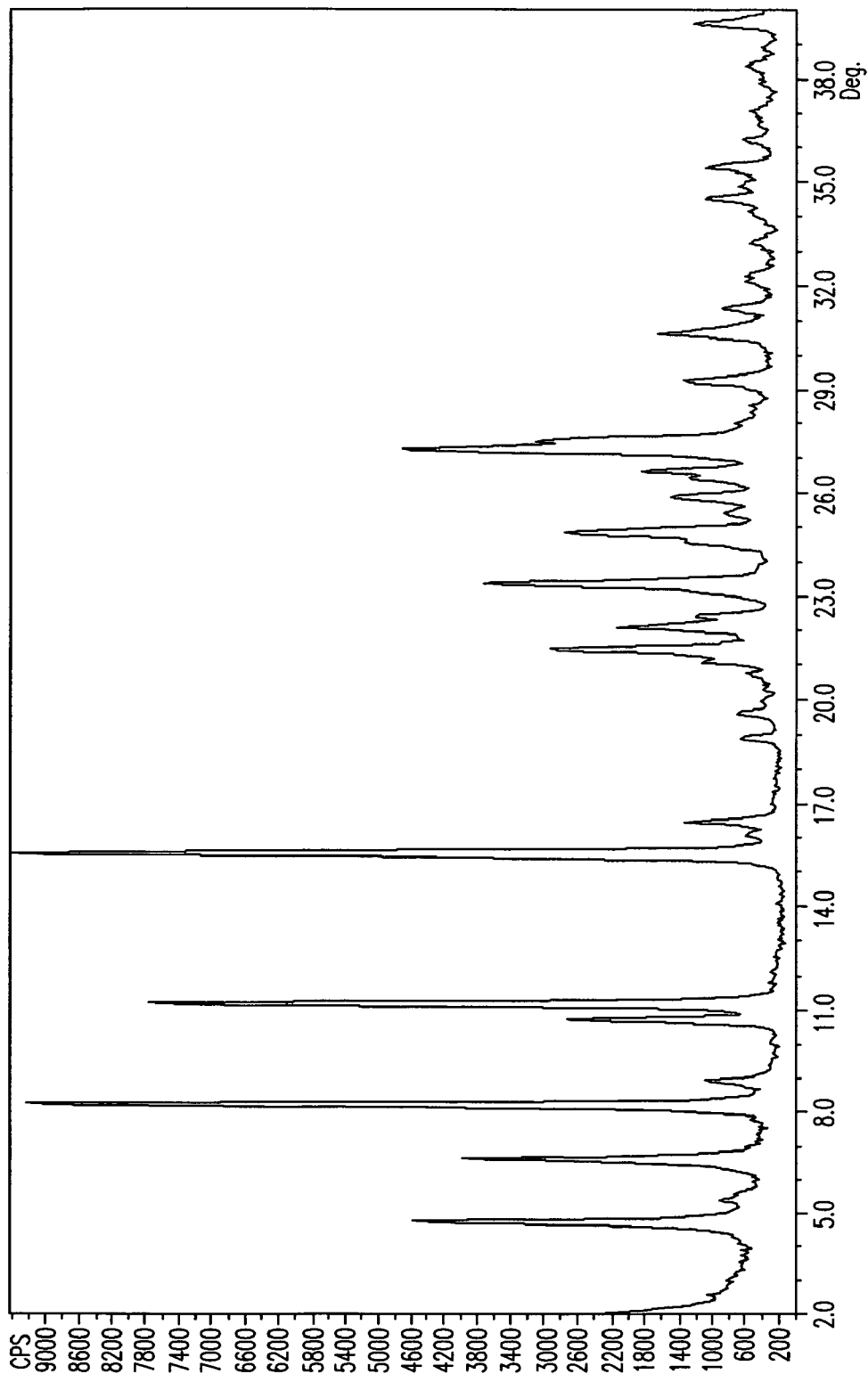
FIG. 1 is a characteristic X-ray powder diffraction pattern for monosodium mycophenolate form M1.
Figure 2:
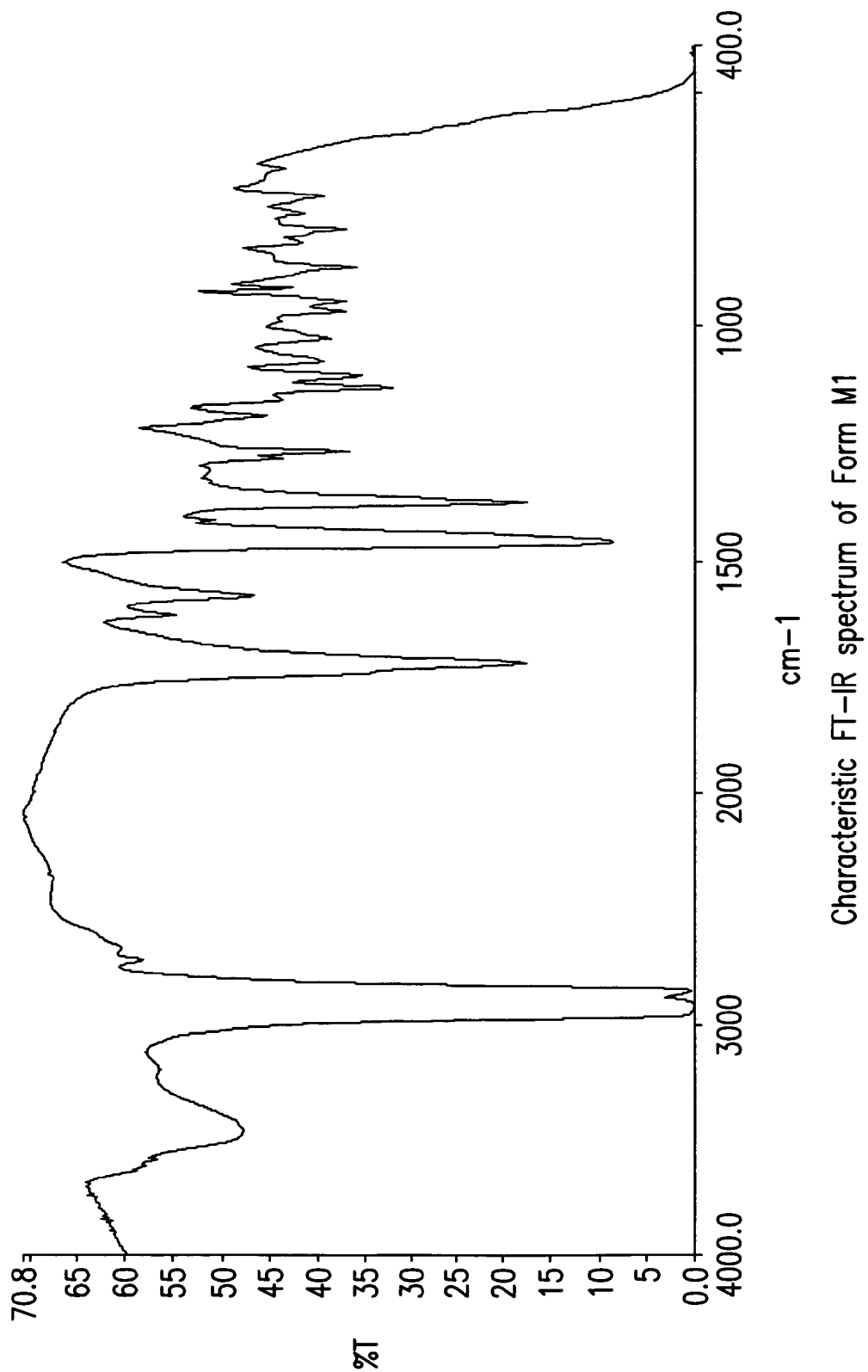
FIG. 2 is a characteristic FT-IR spectrum of Monosodium Mycophenolate form M1.
Figure 3:
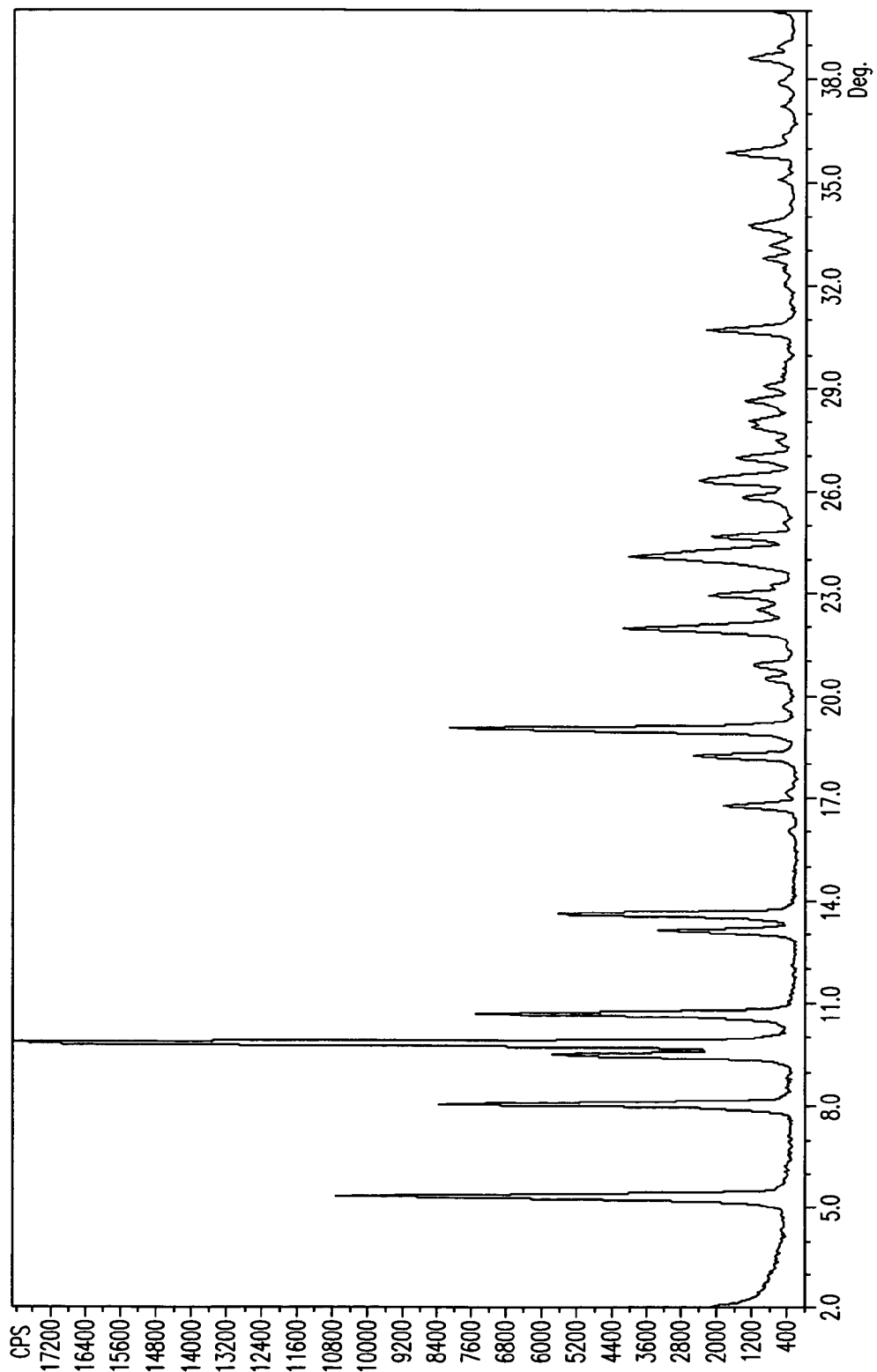
FIG. 3 is a characteristic X-ray powder diffraction pattern for monosodium mycophenolate form M2.
Figure 4:
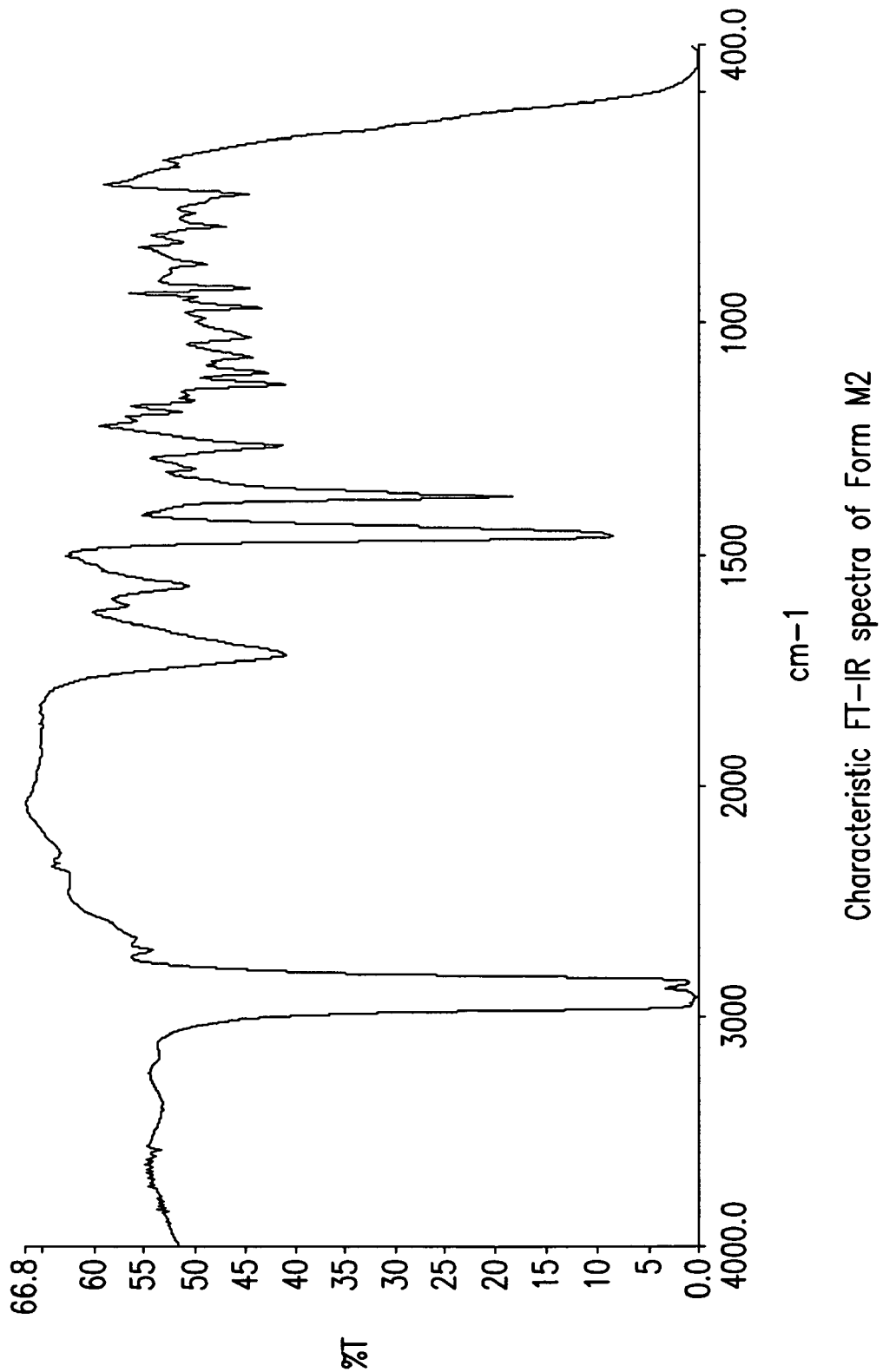
FIG. 4 is a characteristic FT-IR spectrum of Monosodium Mycophenolate form M2.
Figure 42:
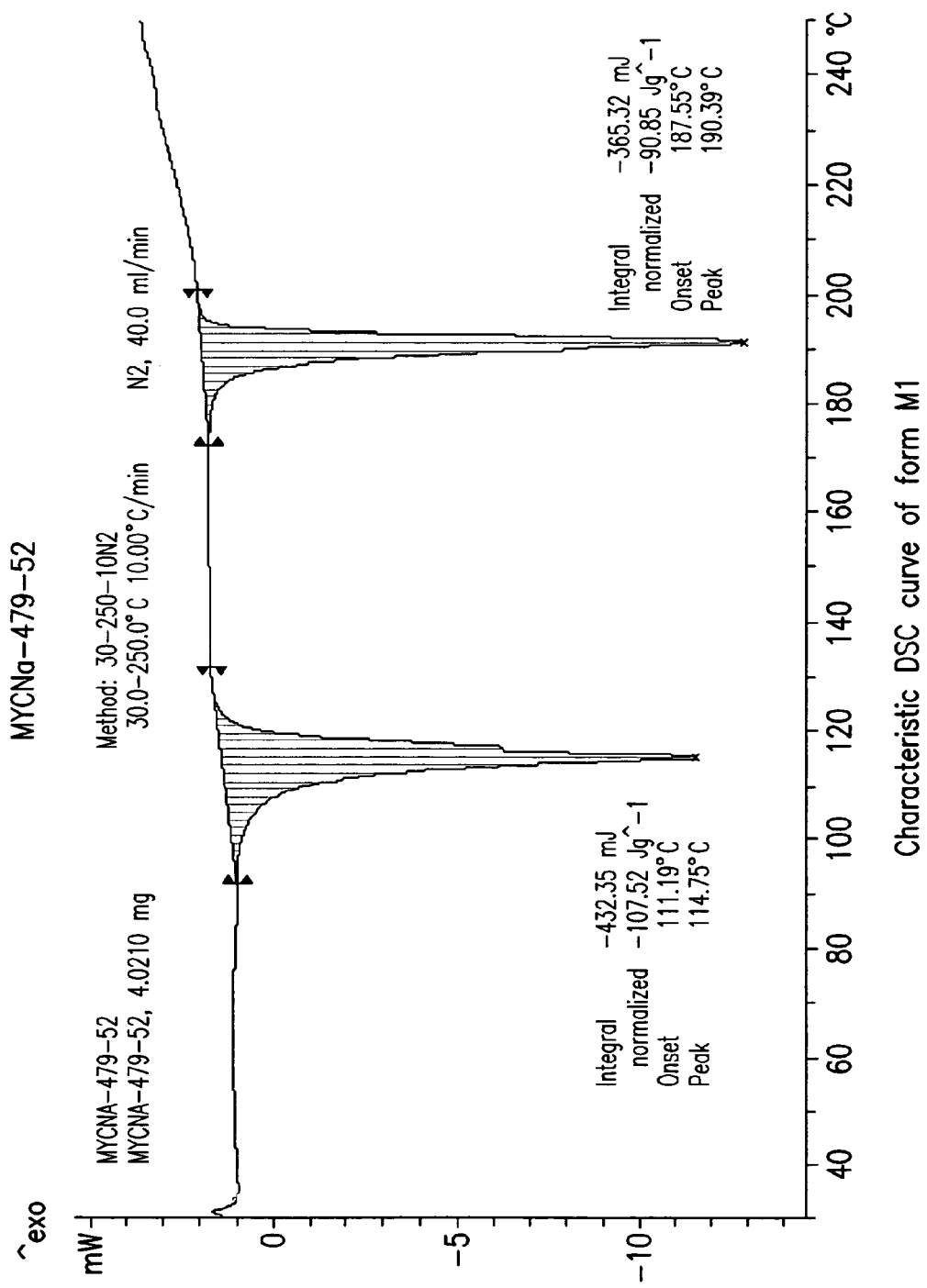
FIG. 42 is a characteristic DSC curve for monosodium mycophenolate form M1.
Figure 43:
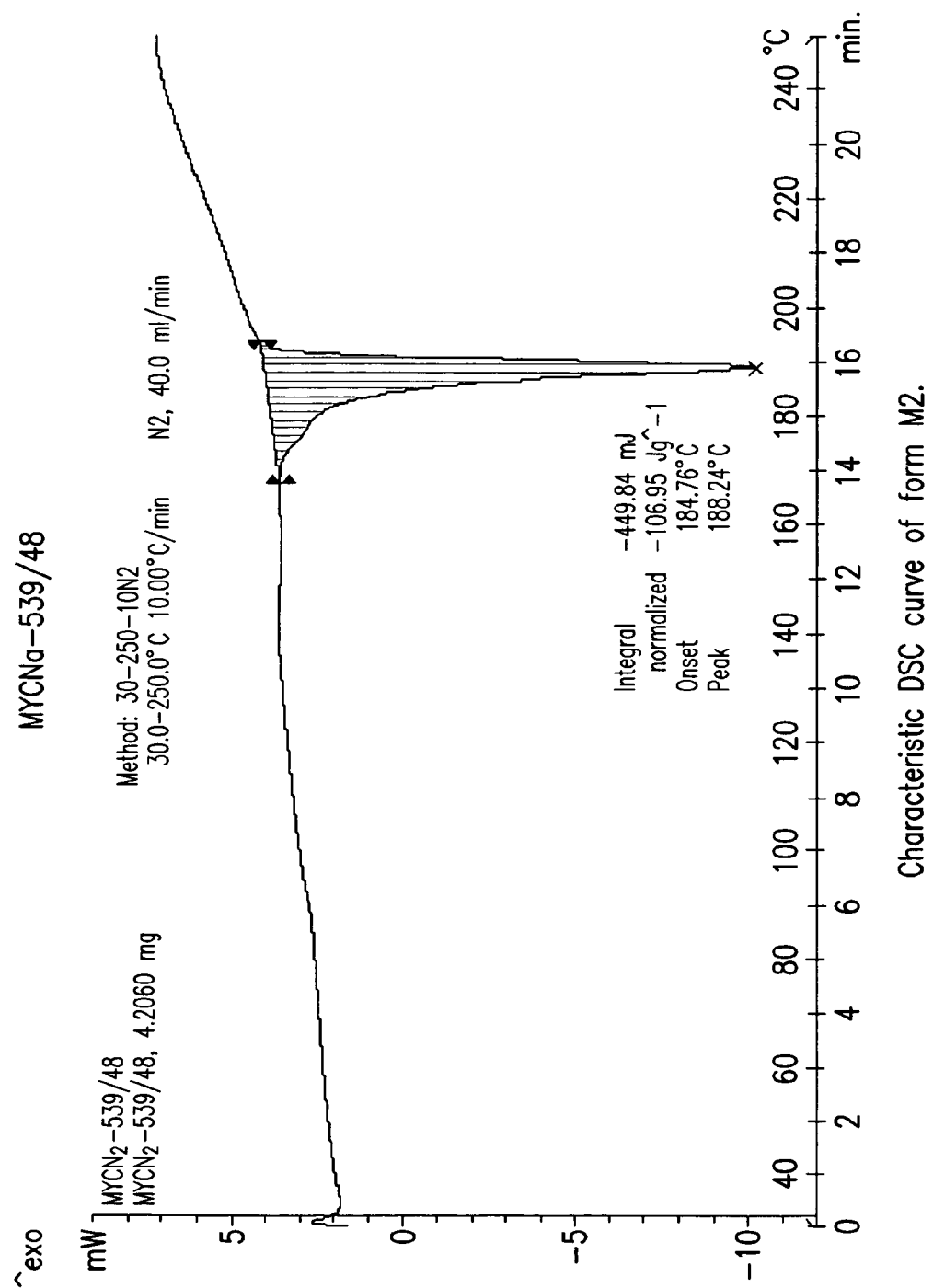
FIG. 43 is a characteristic DSC curve for monosodium mycophenolate form M2.

In one aspect, the present invention is a crystalline mycophenolate sodium, denominated Form M1, characterized by at least one of a powder XRD pattern with peaks at 4.7, 6.6, 11.2 and 15.6±0.2 degrees 2 theta (FIG. 1) or FTIR peaks at 3450, 1723, 1619, 1578, 1268 and 1132 cm-1 (FIG. 2). Form M1 may be further characterized by XRD peaks at 8.2, 21.5 and 23.4±0.2 degrees 2 theta. Form M1 may be further characterized by IR peaks at 1192, 1106, 1077, 1030, 971, 950, 921, 875, 794, 761, 723, and 666 cm-1. Form M1 is a hydrate having about 3.5 to about 5.0% water measured by TGA and Karl-Fischer. The DSC melting peak of form M1 is at about 190-191° C. (FIG. 42). Form M1 may be substantially free of other crystalline forms of mycophenolate sodium. The phrase "substantially free of other crystalline forms", as used herein, means that other crystalline forms make up less than or equal to about 10% by weight of the sample. Form M1 is a monohydrate.

One process for preparing crystalline mycophenolate sodium M1 includes preparing a solution of mycophenolic acid in a $C_1$-$C_4$ alcohol; combining a base and a source of sodium with the solution; cooling the mixture; and recovering the crystalline form. Recovery is preferably carried out within about 1 to 5 hours in that additional time may cause a transformation to another form. In one embodiment, the process for preparing mycophenolate sodium Form M1 includes dissolving MPA in an alcohol, preferably methanol, preferably with stirring; adding a base and a source of sodium to the stirred reaction mixture dropwise at about room temperature; cooling the reaction mixture to about −15° C.; letting the reaction mixture stand at about −15° C., preferably for about 3 hours; and drying the isolated product, preferably at about 40-45° C. in a vacuum oven.

As exemplified, to a stirred solution of MPA in methanol, preferably at a concentration of about 5 to about 10 ml/g, a source of sodium is added. Preferably, a 30% solution of sodium methoxide in methanol is added, more preferably dropwise at room temperature. The reaction mixture is then preferably cooled, more preferably to a temperature below about 0° C., most preferably to about −15° C. In one embodiment, the cooling is carried out rapidly, within about 1 hour and then stirred for about 1-3 hours or until complete precipitation. The precipitated product is recovered and may be dried at about 40 to about 45° C. in a vacuum oven.

Form M1 may also be prepared by drying a solution of mycophenolate sodium in water. In a preferred embodiment, the process for preparing mycophenolate sodium Form M1 includes dissolving sodium mycophenolate in water at elevated temperature, preferably about 60° C., preferably with stirring; allowing the solution to cool to about room temperature; and evaporating the solution to dryness. Drying may be carried out under ambient or reduced pressure.

Another process for preparing crystalline mycophenolate sodium Form M1 comprises preparing a solution of mycophenolic acid if a C3-C8 ketone; combining a base and a source of sodium with the solution to form a mixture; crystallizing the crystalline form from the mixture; and recovering the crystalline form. In one embodiment, Form M1 is prepared by crystallization from acetone, in presence of sodium ions, by addition of methanol.

Another process for preparing crystalline mycophenolate sodium M1 comprises preparing a solution of sodium mycophenolate in ethanol, preferably absolute ethanol; crystallizing the crystalline form from the solution; and recovering the crystalline form. In a preferred embodiment, the solution of step is heated, preferably to a temperature of at least about 60° C., and more preferably at to about reflux temperature. The solution is preferably cooled, more preferably at about room temperature, and allowed to crystallize over night.

Another process for preparing crystalline mycophenolate sodium M1 comprises contacting crystalline mycophenolate sodium with water vapor. The crystalline mycophenolate sodium forms is preferably Form M3. In a preferred embodiment, the crystalline mycophenolate sodium is placed in a hygroscopic chamber at about 100% relative humidity, preferably at about room temperature, and preferably for about one week or until Form M1 is obtained.

Form M3

Figure 5:
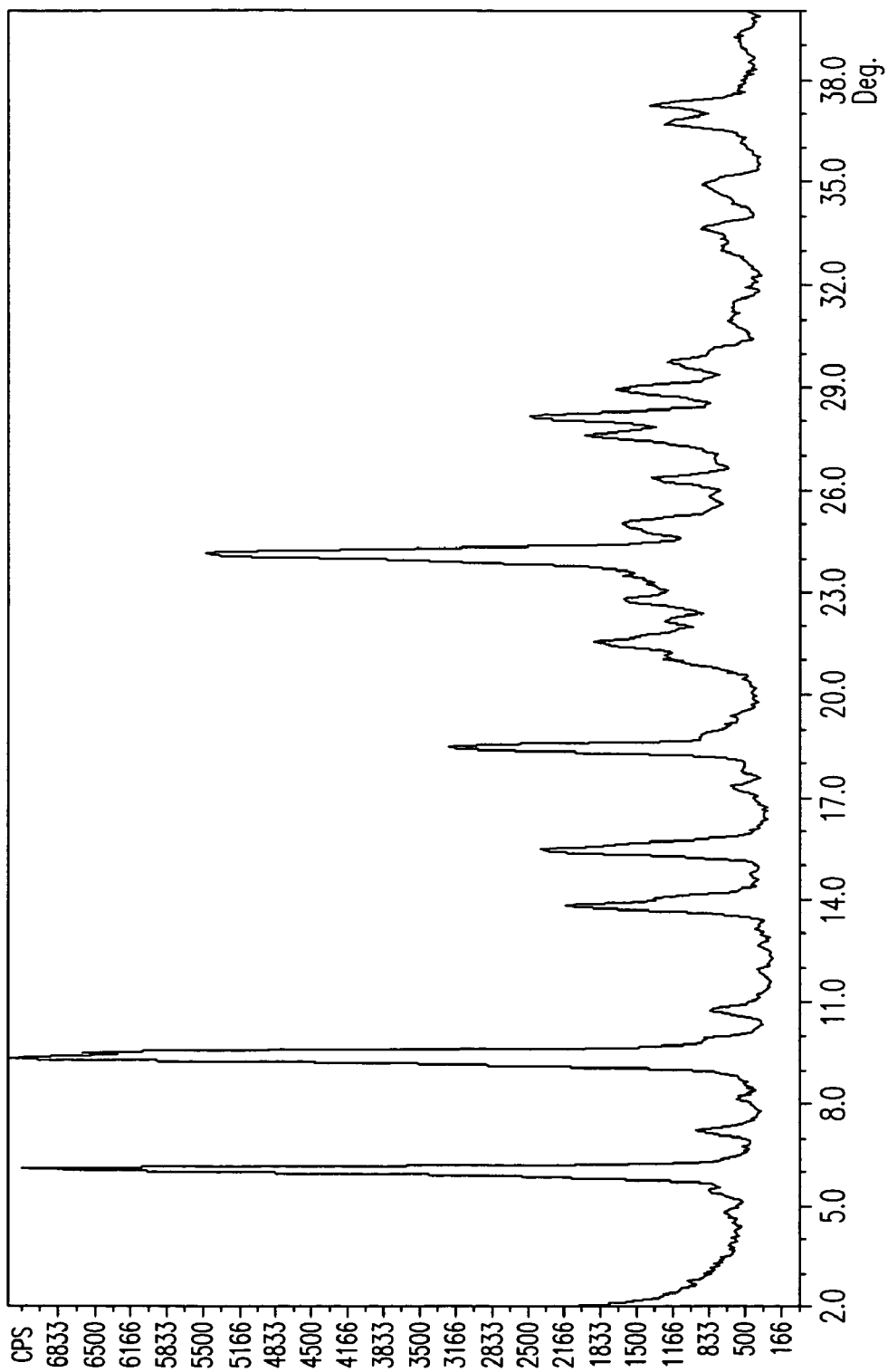
FIG. 5 is a characteristic X-ray powder diffraction pattern for monosodium mycophenolate form M3.
Figure 6:
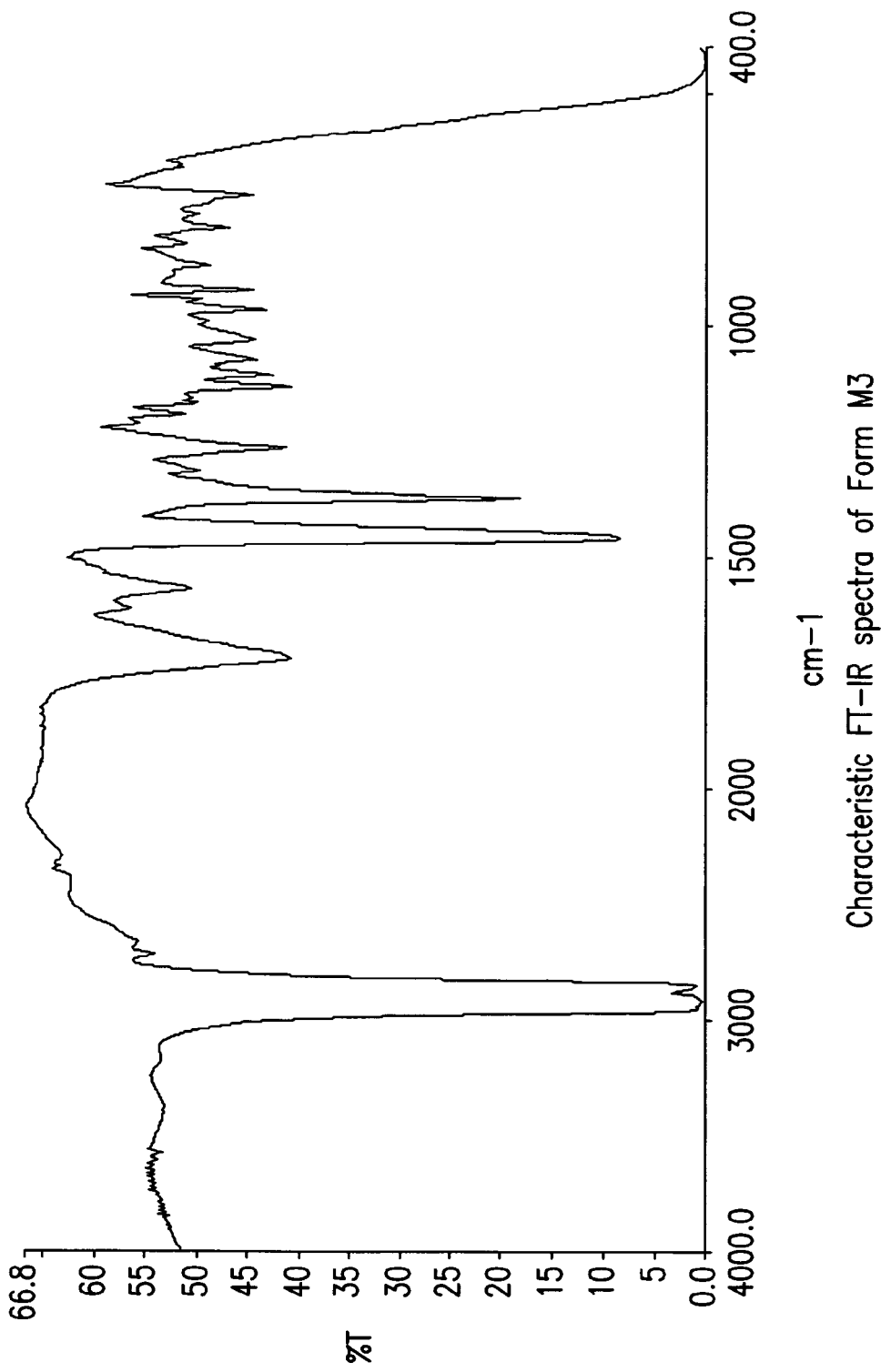
FIG. 6 is a characteristic FT-IR spectrum of Monosodium Mycophenolate form M3.
Figure 44:
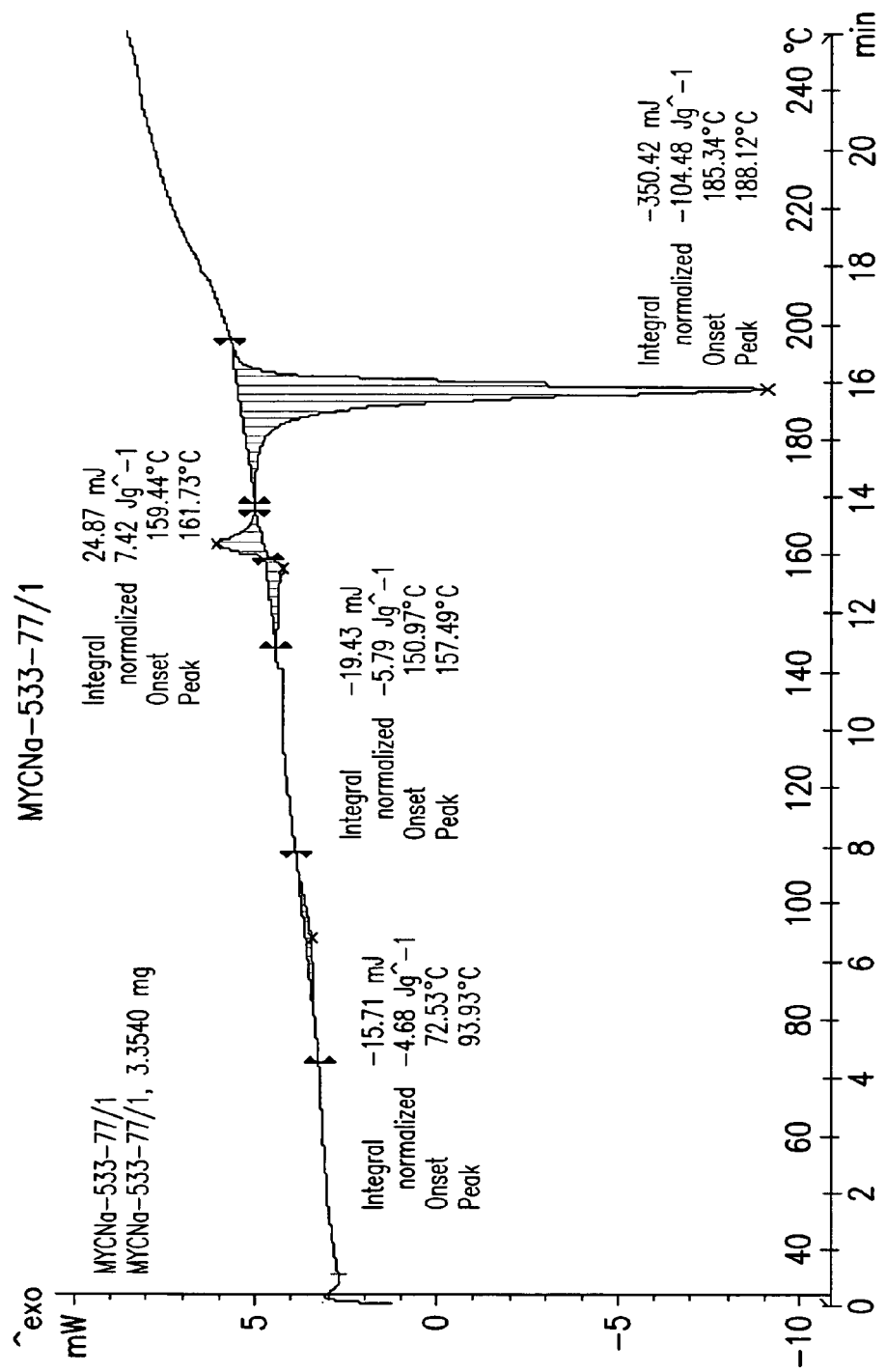
FIG. 44 is a characteristic DSC curve for monosodium mycophenolate form M3.

In another aspect, the present invention is a crystalline mycophenolate sodium, denominated Form M3, characterized by a powder XRD pattern with peaks at 6.0, 9.3, 15.5, and 18.4±0.2 degrees 2 theta (FIG. 5) and FTIR peaks at 3414, 1713, 1618, 1567, 1264 and 1134 cm-1 (FIG. 6). Form M3 may be further characterized by XRD peaks at 7.2, 10.8, 13.8, and 24.0±0.2 degrees 2 theta. Form M3 may be further characterized by IR peaks at 1415, 1312, 1202, 1108, 1078, 1034, 972, 947, 922, 877, 827, 809, 793, and 722 cm$^{-1}$. Form M3 may be substantially free of other crystalline forms of Mycophenolate sodium. Form M3 has a melting point at about 157 to about 158° C. followed by an exothermic solid-solid transition, caused by the transformation of form M3 to form M2, which shows a DSC melting peak at about 188 to about 190° C. (FIG. 44). Weight loss of mass of heating up to melting is 0.7% as measured by TGA. (0.8% by KF). Form M3 is anhydrous.

Form M3 is generally obtained by crystallization from a $C_1$ to $C_4$ alcohol, preferably methanol, followed by extended stirring. Form M3 has been obtained after leaving the crystals for extended, more than about 15 hours, more preferably about 20 to about 25 hours in the reaction mixture without stirring, or with presence of sodium hydroxide or sodium ethoxide in the absence of cooling. The extended stirring in the reaction mixture points to a transition of other forms to Form M3 in methanol overtime. As exemplified, the process includes (a) dissolving MPA in methanol with stirring, (b) adding a base and a source of sodium to the stirred reaction mixture dropwise at room temperature, (c) cooling the reaction mixture to −15° C. over a period of 1 hour, (d) stirring the reaction mixture at −15° C. for an additional 20-24 hours, (e) filtering off the precipitated product, (f) washing the isolated product with methanol, and (g) drying the isolated product at 40-45° C. in a vacuum oven.

Form M4

Figure 7:
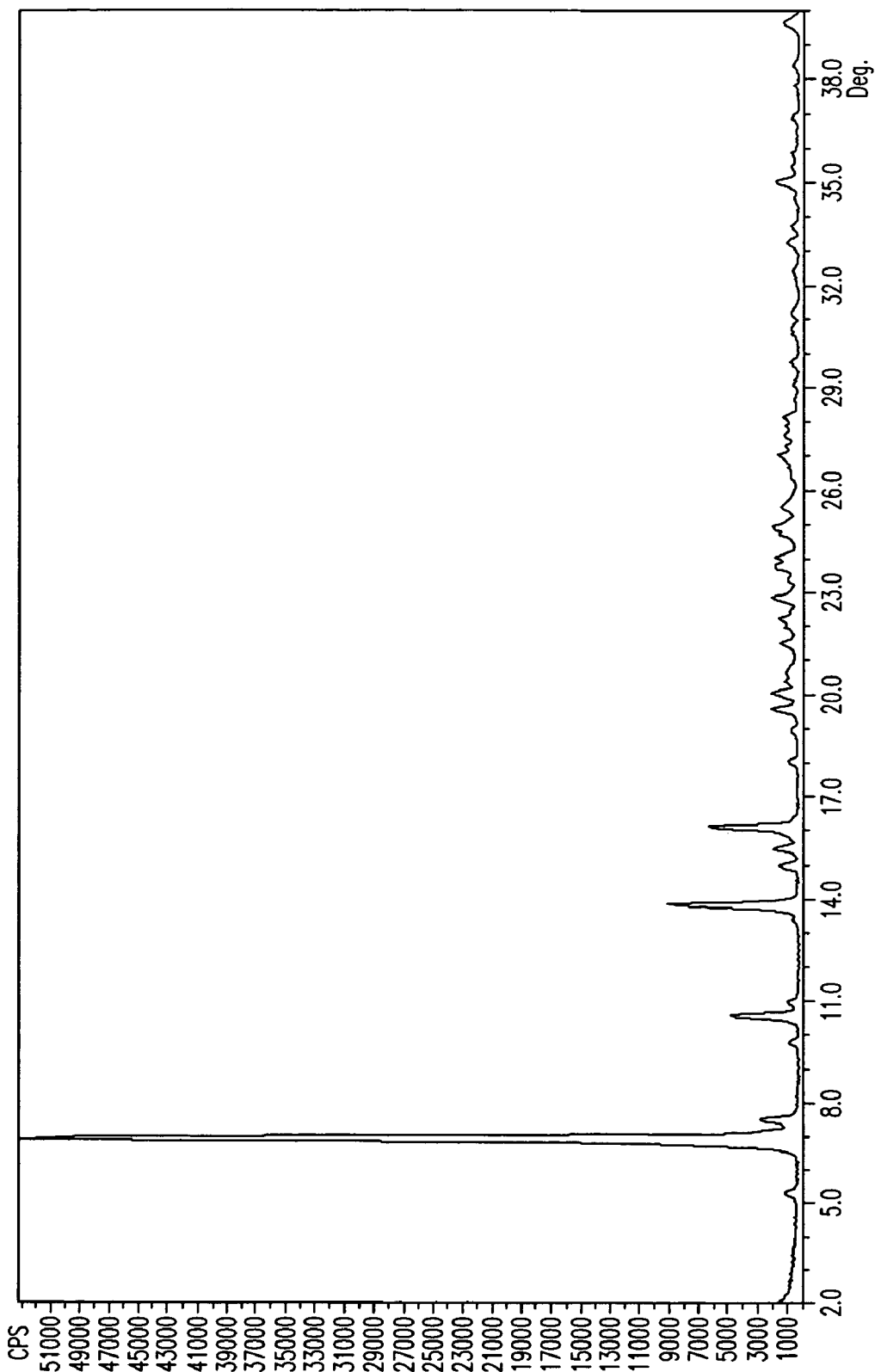
FIG. 7 is a characteristic X-ray powder diffraction pattern for monosodium mycophenolate form M4.
Figure 45:
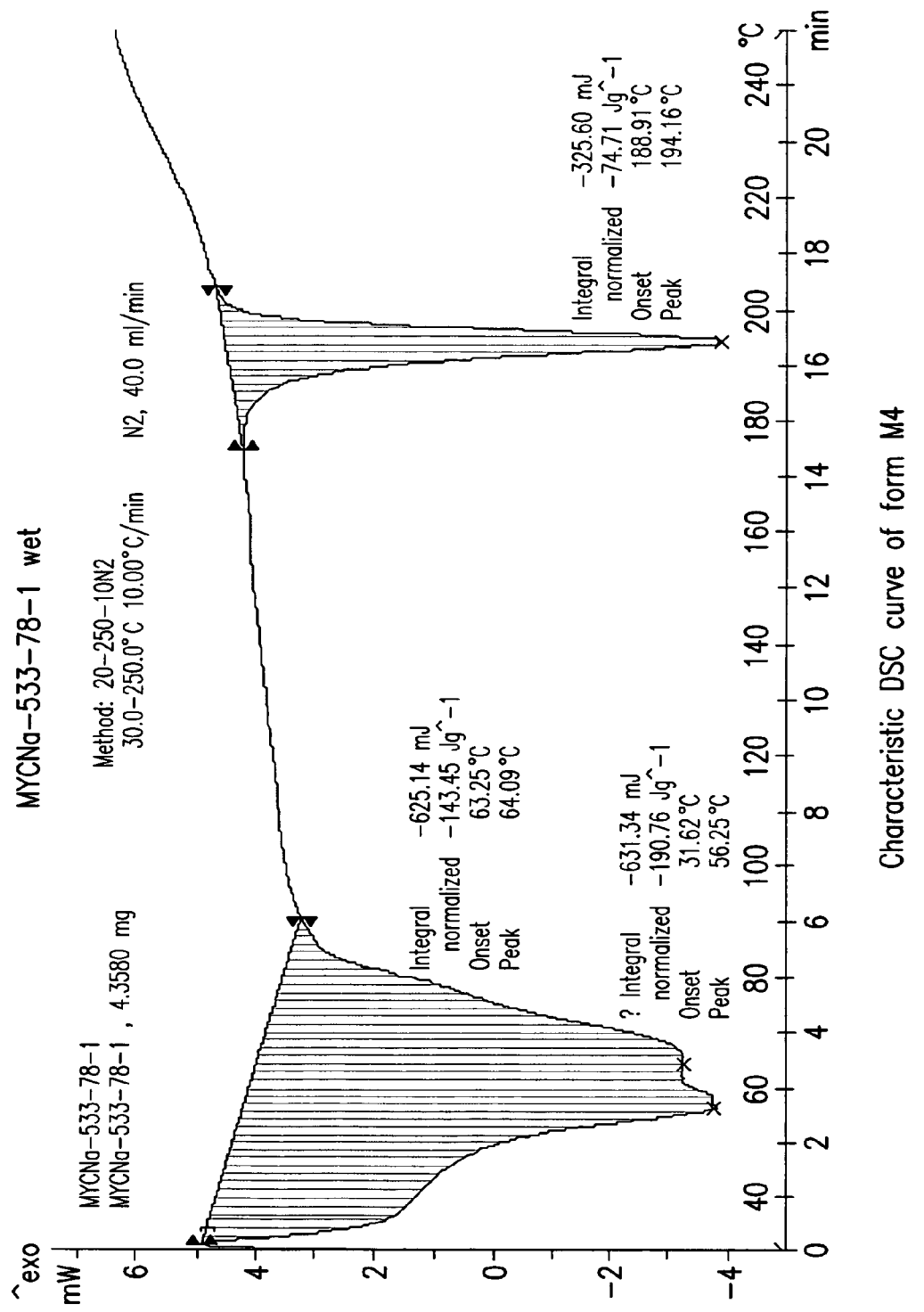
FIG. 45 is a characteristic DSC curve for monosodium mycophenolate form M4.
Figure 46:
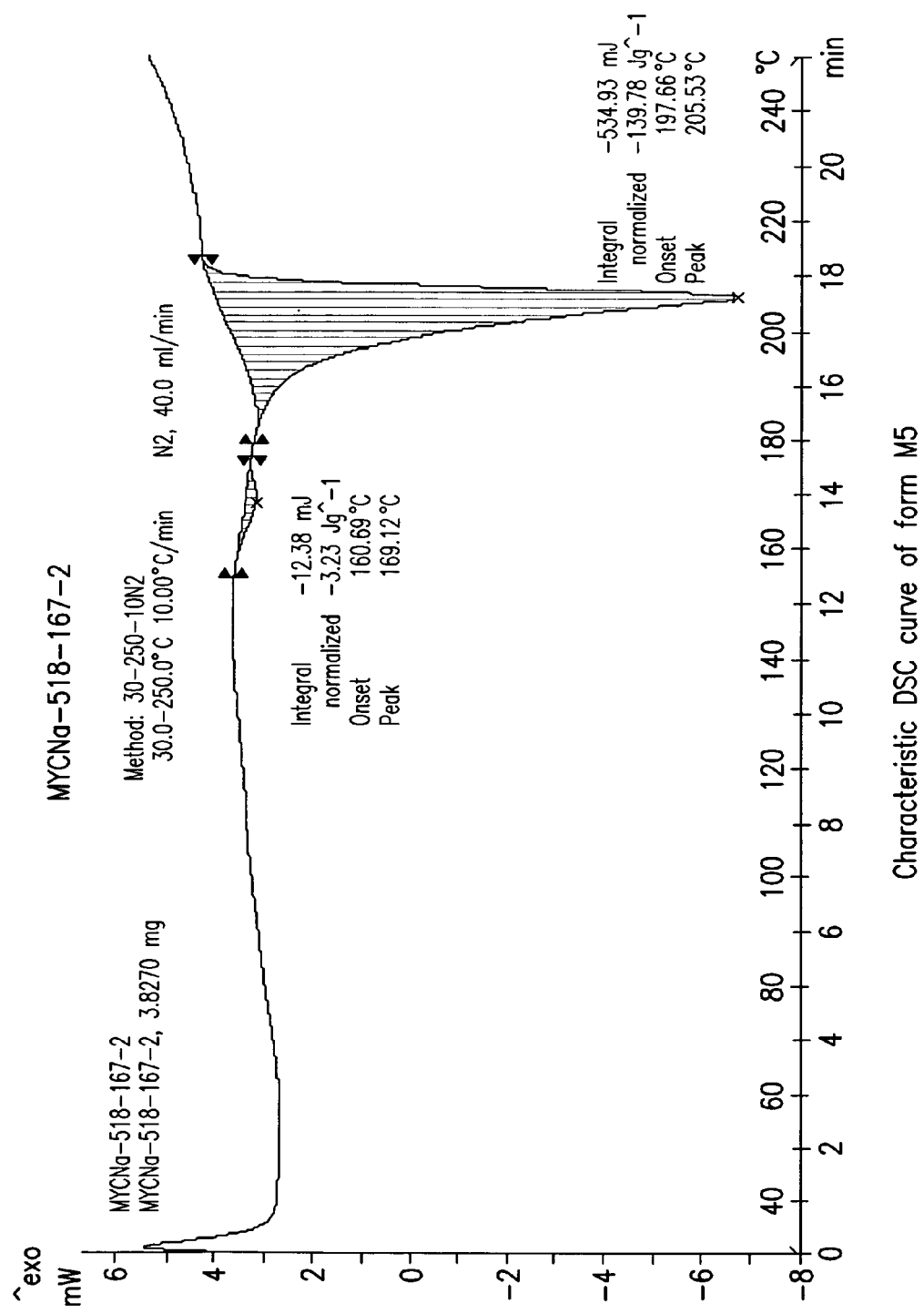
FIG. 46 is a characteristic DSC curve for monosodium mycophenolate form M5.

In another aspect, the present invention is a crystalline mycophenolate sodium, denominated Form M4, characterized by a powder XRD pattern with peaks at 7.1, 7.6, 10.7, 14.0 and 16.3±0.2 degrees 2 theta (FIG. 7). Form M4 may be further characterized by XRD peaks at 5.4, 19.7 and 20.2±0.2 degrees 2 theta. Form M4 may be substantially free of other crystalline forms of mycophenolate sodium. The DSC curve of Form M4 has three endothermic peaks, two due to desolvation in a low temperature range and one due to melting at about 194° C. (FIG. 45). Weight loss is about 32.1% as measured by TGA. Form M4 is a solvated form.

The invention provides a process for preparing mycophenolate sodium Form M4. The process involves dissolving MPA in methanol, then adding a base and a source of sodium. The resulting reaction mixture is then cooled, preferably to about −20° C. and about −10° C., more preferably about −15° C. Preferably the cooling is carried out over a period of more than 3 hours. Afterwards, the resulting reaction mixture is stirred, preferably in this temperature range, preferably for more than 3 hours, more preferably at least about 15 hours. This delay in recovery causes a transition to Form M4. Finally, the crystalline form is recovered from the mixture.

Form M5

Figure 8:
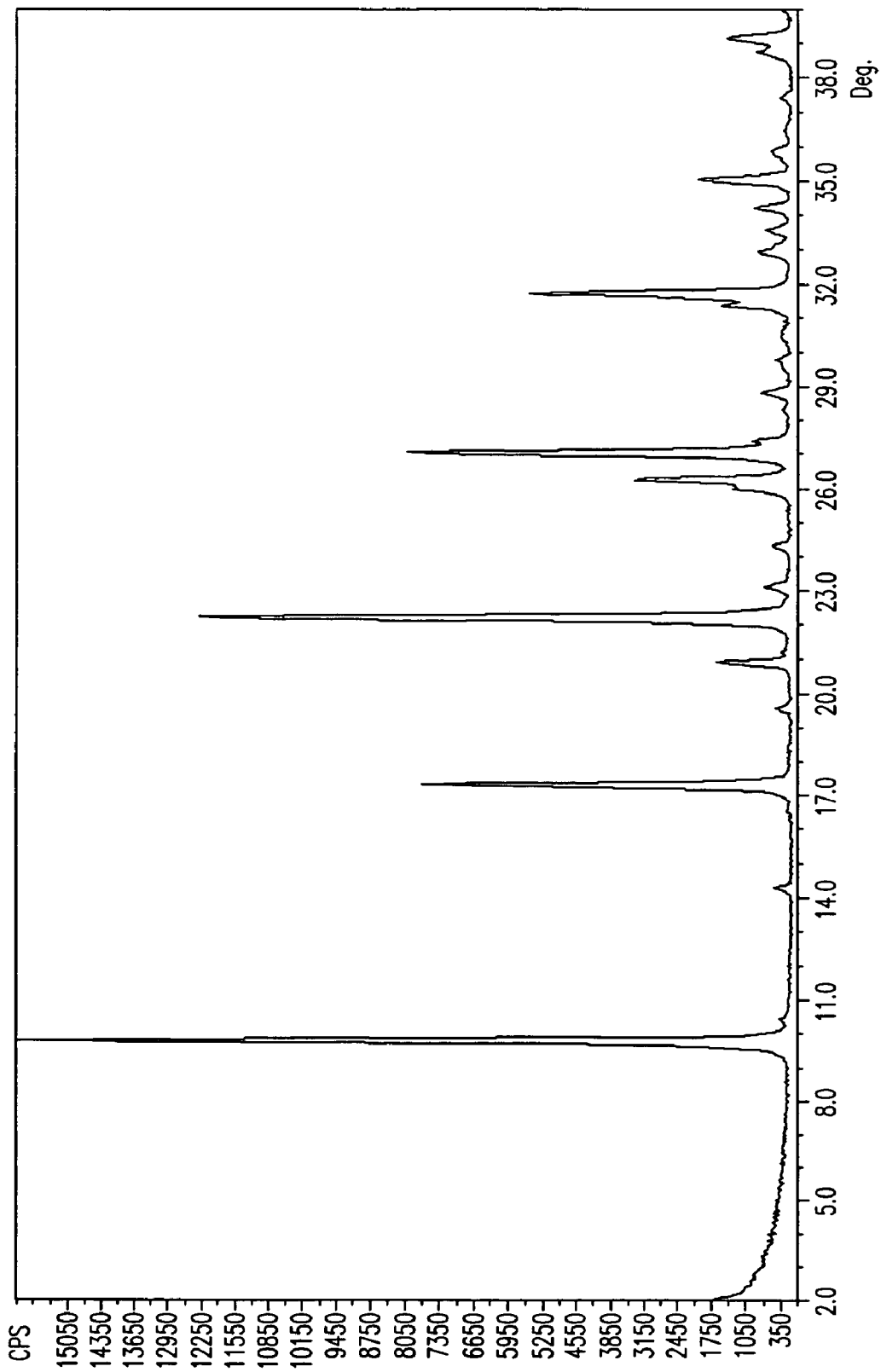
FIG. 8 is a characteristic X-ray powder diffraction pattern for monosodium mycophenolate form M5.
Figure 49:
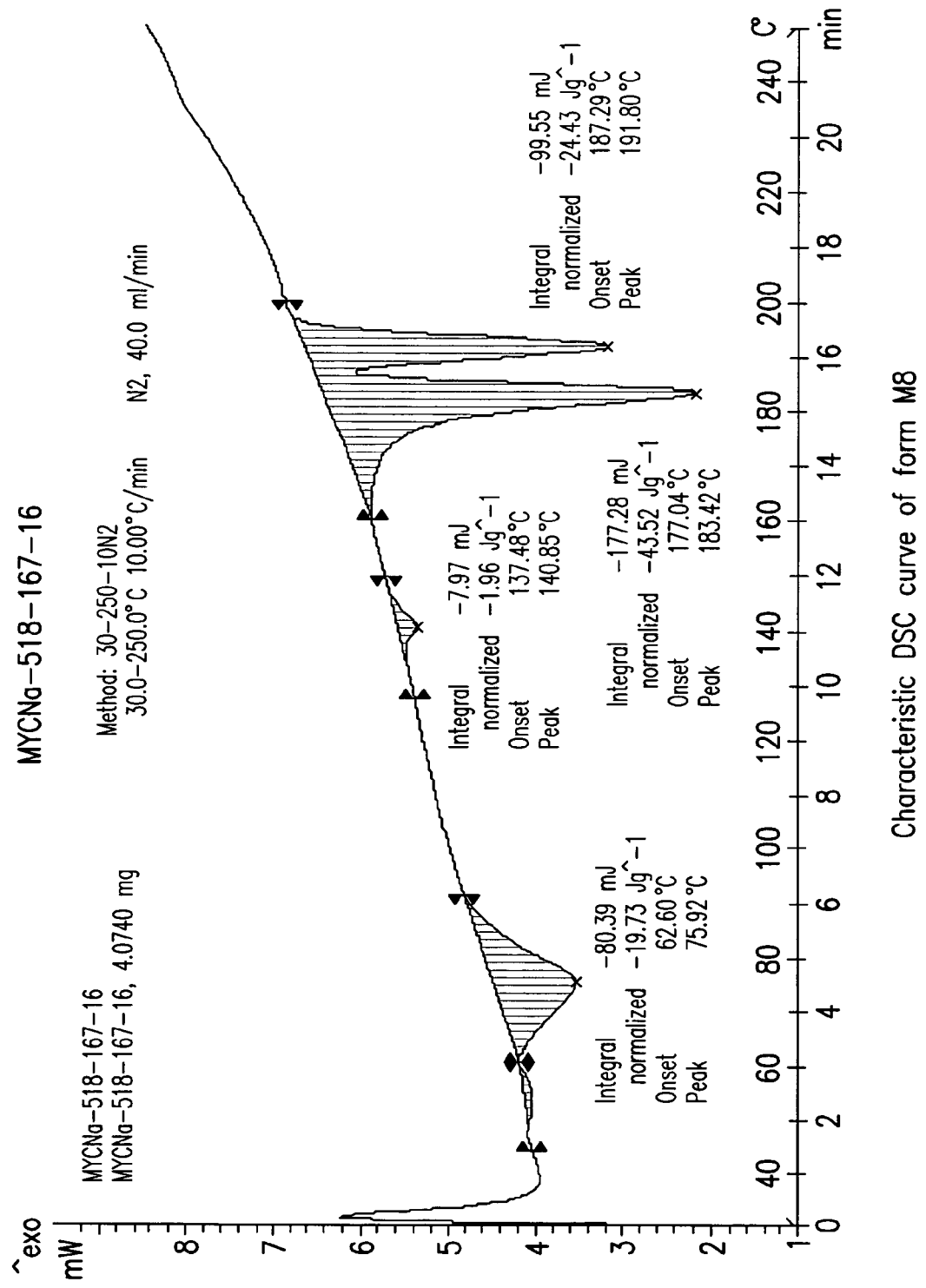
FIG. 49 is a characteristic DSC curve for monosodium mycophenolate form M8.

In another aspect, the present invention is a crystalline mycophenolate sodium, denominated Form M5, characterized by a powder XRD pattern with peaks at 9.8, 17.4, 22.2, 27.1, and 31.7±0.2 degrees 2 theta (FIG. 8). Form M5 may be further characterized by XRD peaks at 21.0, 26.3 and 31.4±0.2 degrees 2 theta. Form M5 may be substantially free of other crystalline forms of Mycophenolate sodium. Form M5 is an anhydrous form showing one DSC small endothermic peak in the range of 169-171° C. and a DSC melting peak in the temperature range of about 205 to about 221° C. (FIG. 49). Weight loss is 0.8% as measured by TGA. Form M5 is anhydrous.

The invention provides a process for preparing mycophenolate sodium Form M5. Form M5 may be obtained by from 1,4-dioxane. The process involves heating a mixture of sodium mycophenolate and 1,4-dioxane to obtain a solution, preferably to about 80° C. or at reflux temperature, followed by crystallization of the crystalline form from the mixture, preferably by cooling the solution to room temperature. Finally, the crystalline form is recovered.

Preferably, the ratio of 1,4-dioxane to sodium mycophenolate is more than about 100 ml/g.

Form M6

Figure 9:
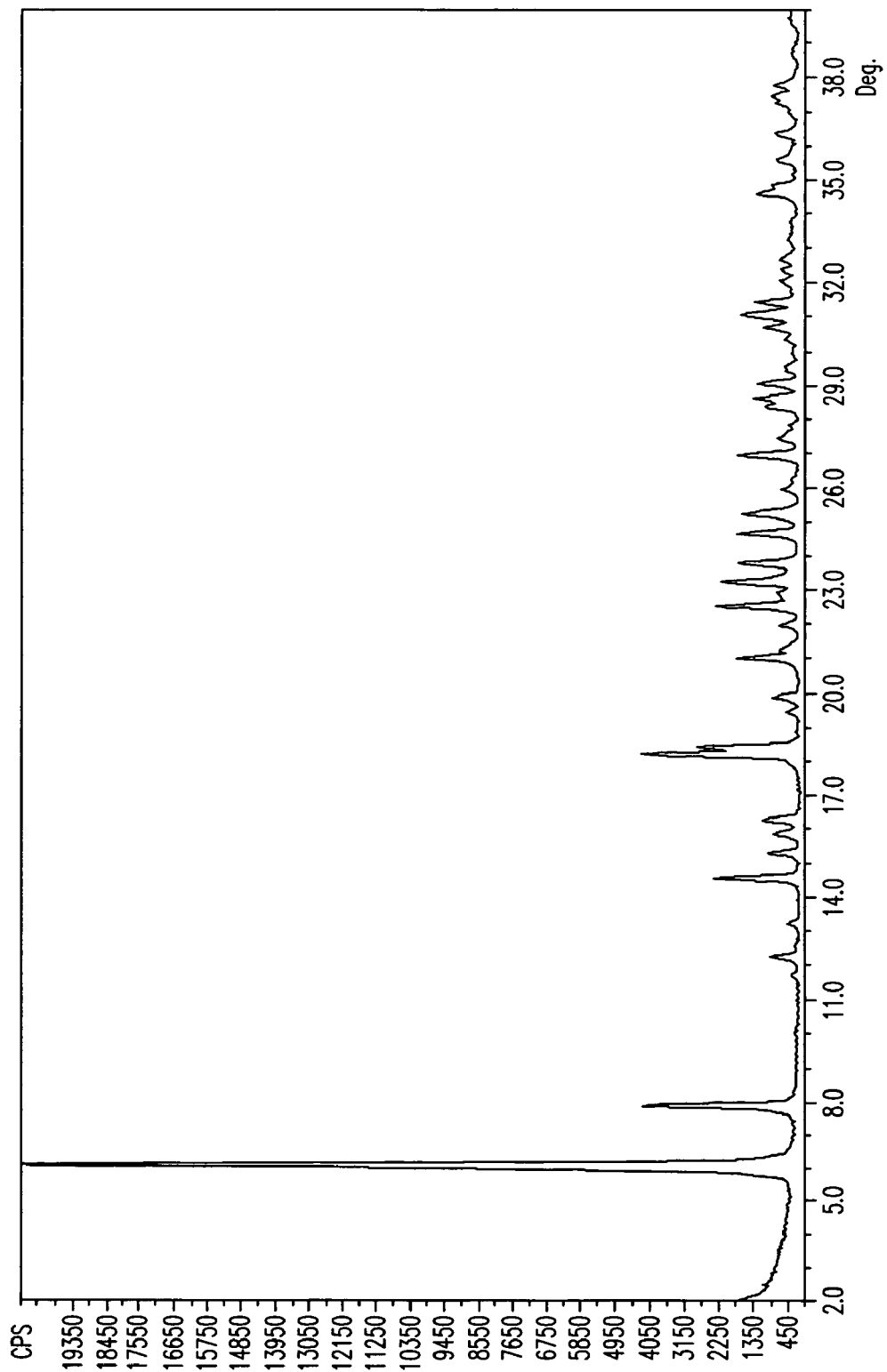
FIG. 9 is a characteristic X-ray powder diffraction pattern for monosodium mycophenolate form M6.
Figure 47:
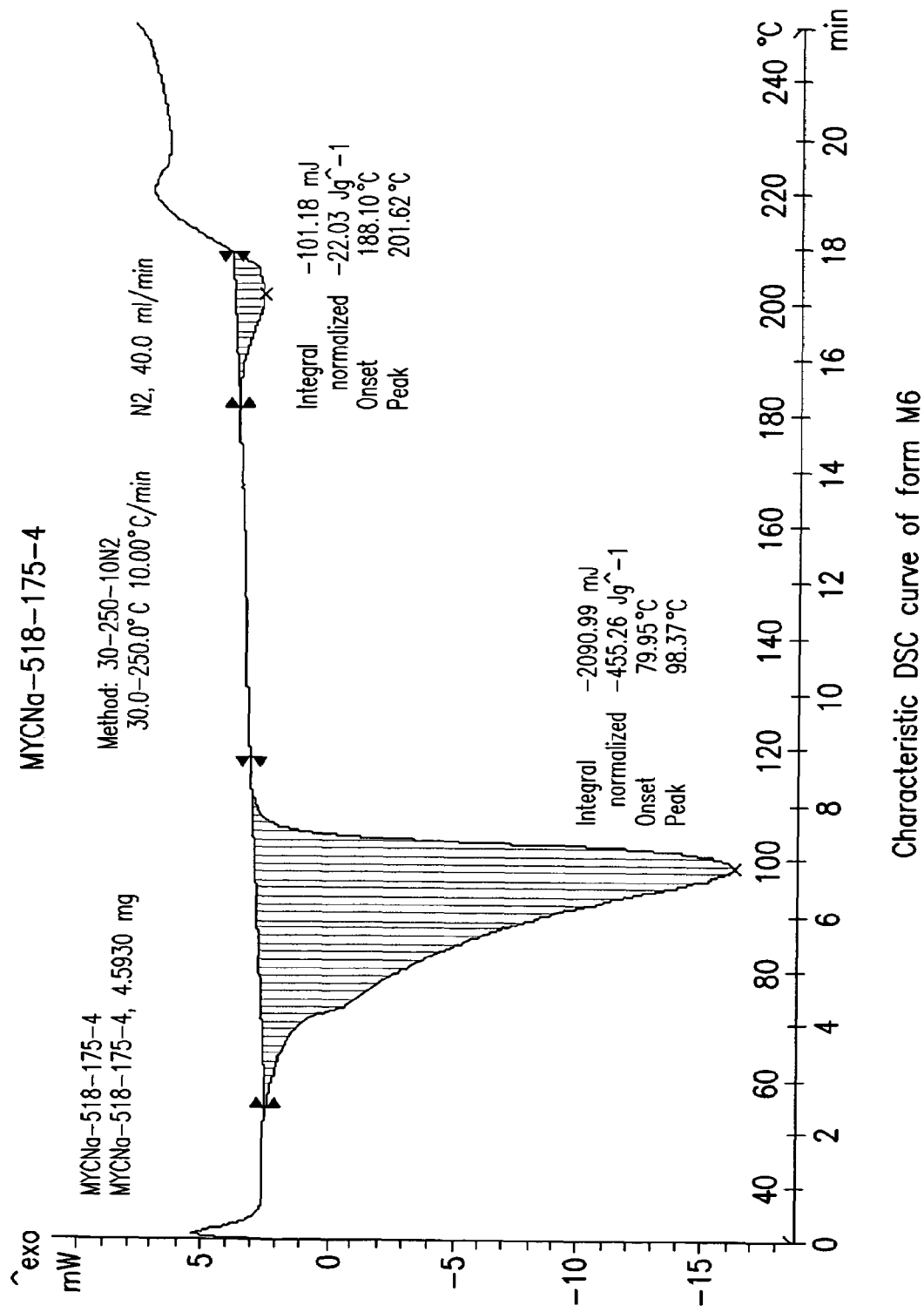
FIG. 47 is a characteristic DSC curve for monosodium mycophenolate form M6.

In another aspect, the present invention is a crystalline mycophenolate sodium, denominated Form M6, characterized by a powder XRD pattern with peaks at 6.1, 7.9, 14.6, 18.2 and 18.5±0.2 degrees 2 theta (FIG. 9). Form M6 may be further characterized by XRD peaks at 21.0 and 22.5±0.2 degrees 2 theta. Form M6 may be substantially free of other crystalline forms of mycophenolate sodium. Form M6 is a solvated crystal form, an acetonate solvate of 1:1 ratio. The DSC curves of both the wet and dried sample indicate a big endothermic peak due to desolvation (FIG. 47). The weight loss measured by TGA is 17.6%, which value fits to one molecule of acetone. Form M6 has a small DSC endothermic melting peak in the range of 199-202° C.

The invention provides a process for preparing mycophenolate sodium M6 by precipitation from water with use of acetone as an antisolvent. As exemplified, sodium mycophenolate is dissolved in water. This solution is combined with acetone to precipitate the crystalline form. After addition of the acetone, the solution may be allowed to stand for optimal crystallization. Finally, the crystalline form is recovered.

Form M7

Figure 10:
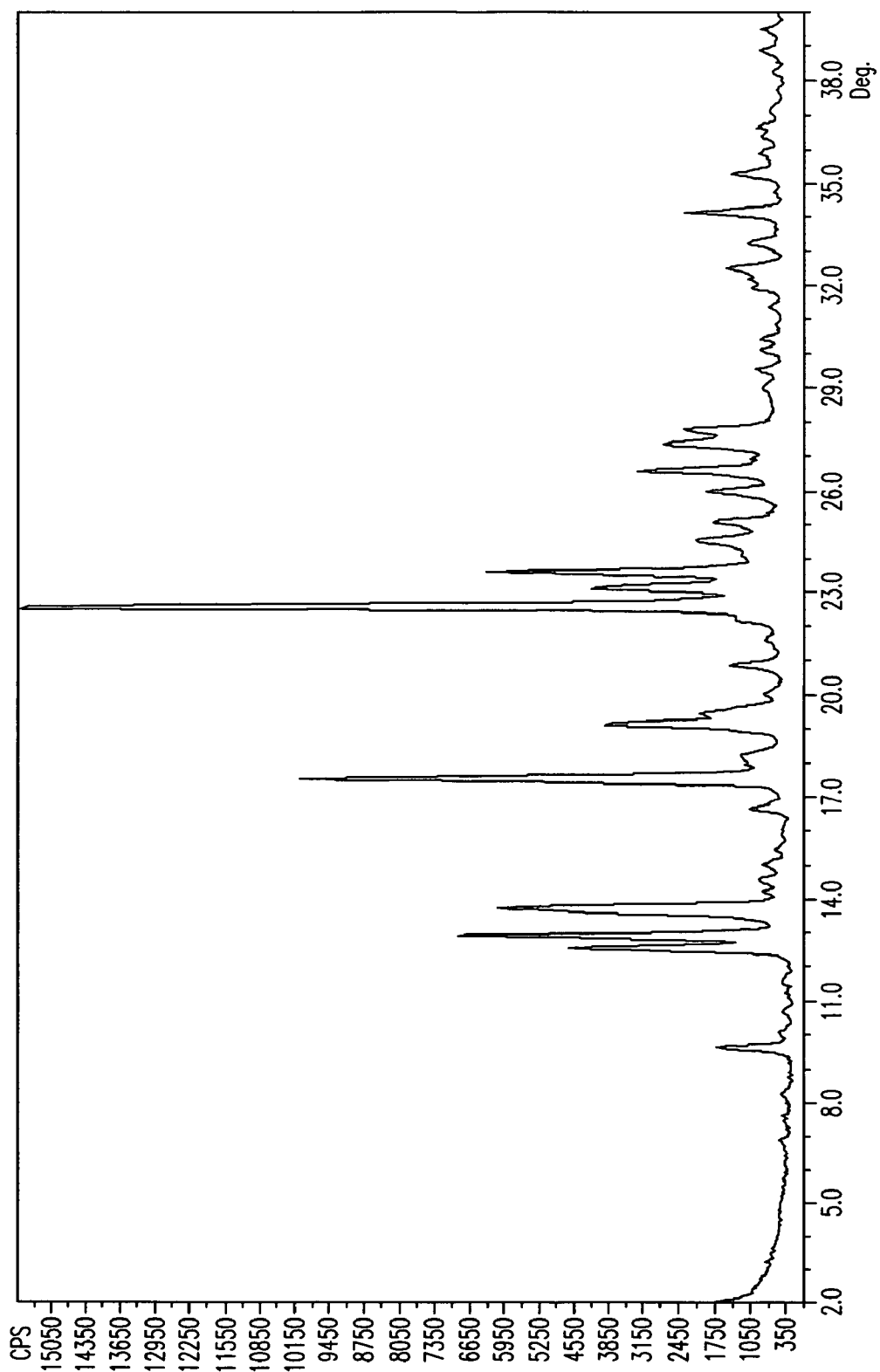
FIG. 10 is a characteristic X-ray powder diffraction pattern for monosodium mycophenolate form M7.
Figure 48:
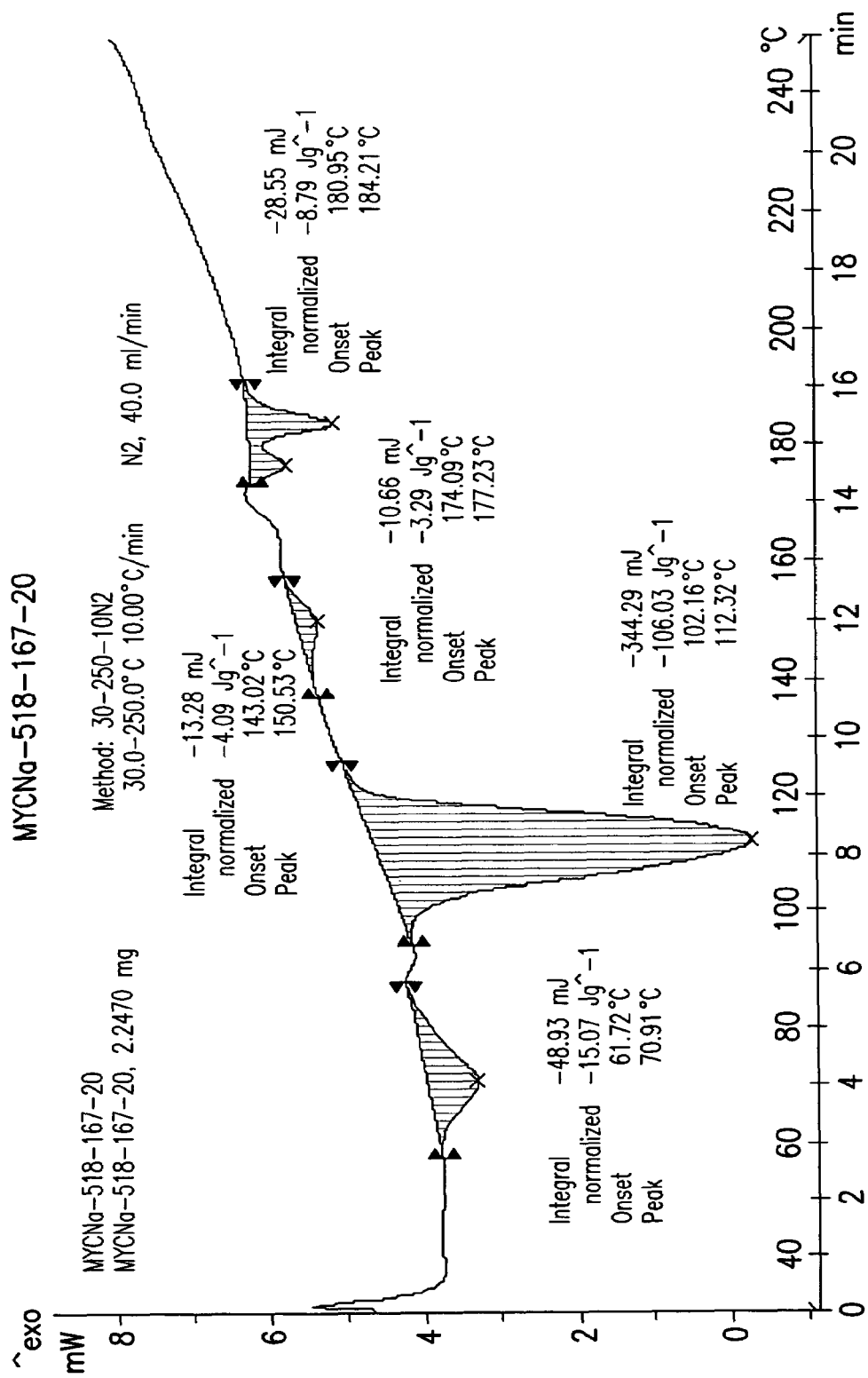
FIG. 48 is a characteristic DSC curve for monosodium mycophenolate form M7.

In another aspect, the present invention is a crystalline mycophenolate sodium, denominated Form M7, characterized by a powder XRD pattern with peaks at 13.0, 13.7, 17.6, 22.6, and 23.6±0.2 degrees 2 theta (FIG. 10). Form M7 may be further characterized by XRD peaks at 9.6, 12.6, 19.2, 23.2 and 27.4±0.2 degrees 2 theta. Form M7 may be substantially free of other crystalline forms of mycophenolate sodium. The DSC curve of M7 shows several endothermic peaks, the first peak due to water loss the second due to desolvation and four other peaks due to melting (FIG. 48). Weight loss is 12.8% as measured by TGA, (results of Karl Fischer: 2.1%). Form M7 is a solvated form.

Form M7 of mycophenolate sodium may be prepared by precipitation from dimethylformamide. As exemplified, sodium mycophenolate is dissolved in dimethylformamide, followed by addition of a $C_3$ to $C_7$ ketone, preferably acetone, and cooling for optimal crystallization. The crystalline form is then recovered by conventional techniques, such as filtration.

Form M8

Figure 11:
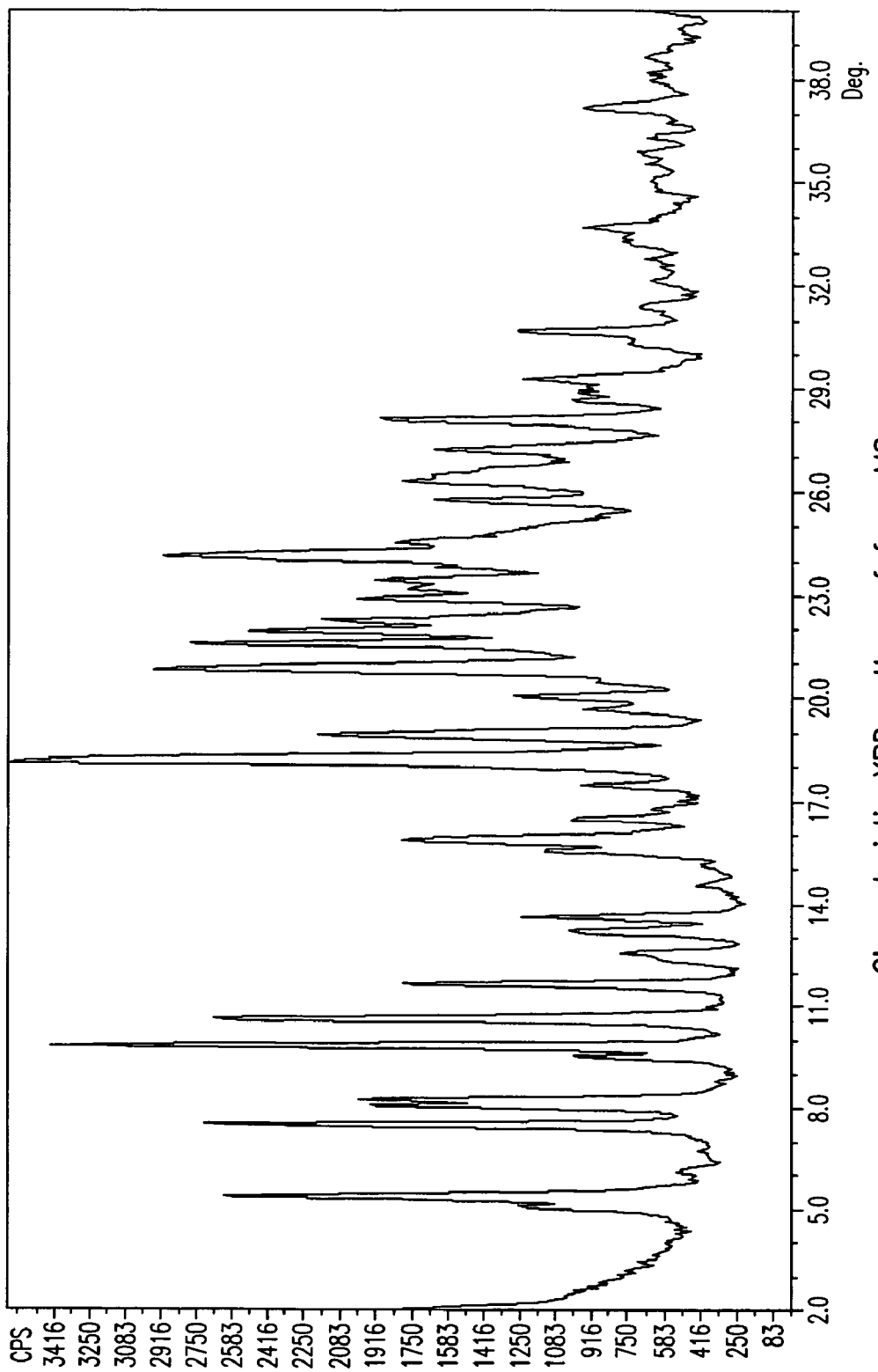
FIG. 11 is a characteristic X-ray powder diffraction pattern for monosodium mycophenolate form M8.

In another aspect, the present invention is a crystalline mycophenolate sodium, denominated Form M8, characterized by a powder XRD pattern with peaks at 5.4, 7.5, 9.8, 10.6, 18.2 and 20.9±0.2 degrees 2 theta (FIG. 11). Form M8 may be further characterized by XRD peaks at 8.1, 11.7 and 15.9±0.2 degrees 2 theta. Form M8 may be substantially free of other crystalline forms of mycophenolate sodium. Form M8 has one or two DSC endothermic peaks due to dehydration depending on the wetness of the sample (FIG. 49). It indicates also one small and two big endothermic peaks due to melting. Weight loss is about 0.4-1.7% as measured by TGA. Form M8 is a solvated form.

The invention provides a process for preparing mycophenolate sodium Form M8. Form M8 may be obtained by dissolving sodium mycophenolate in a mixture of ethyl lactate, and adding ethyl acetate as an antisolvent. In one embodiment, ethyl acetate is added to a solution of sodium mycophenolate in ethyl lactate, followed by cooling for optimal precipitation. The crystalline form may be recovered by conventional techniques.

Form M9

Figure 12:
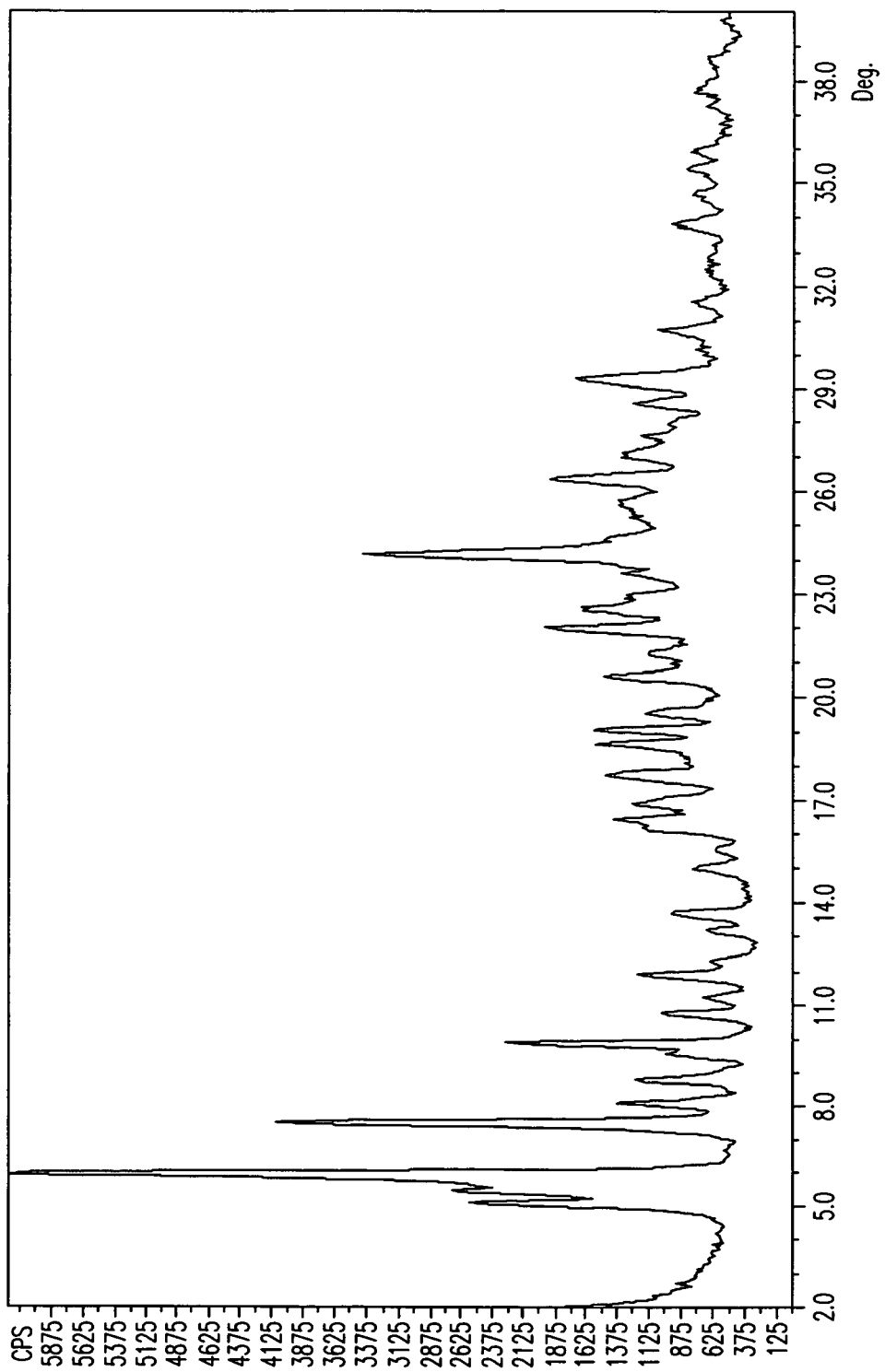
FIG. 12 is a characteristic X-ray powder diffraction pattern for monosodium mycophenolate form M9.
Figure 50:
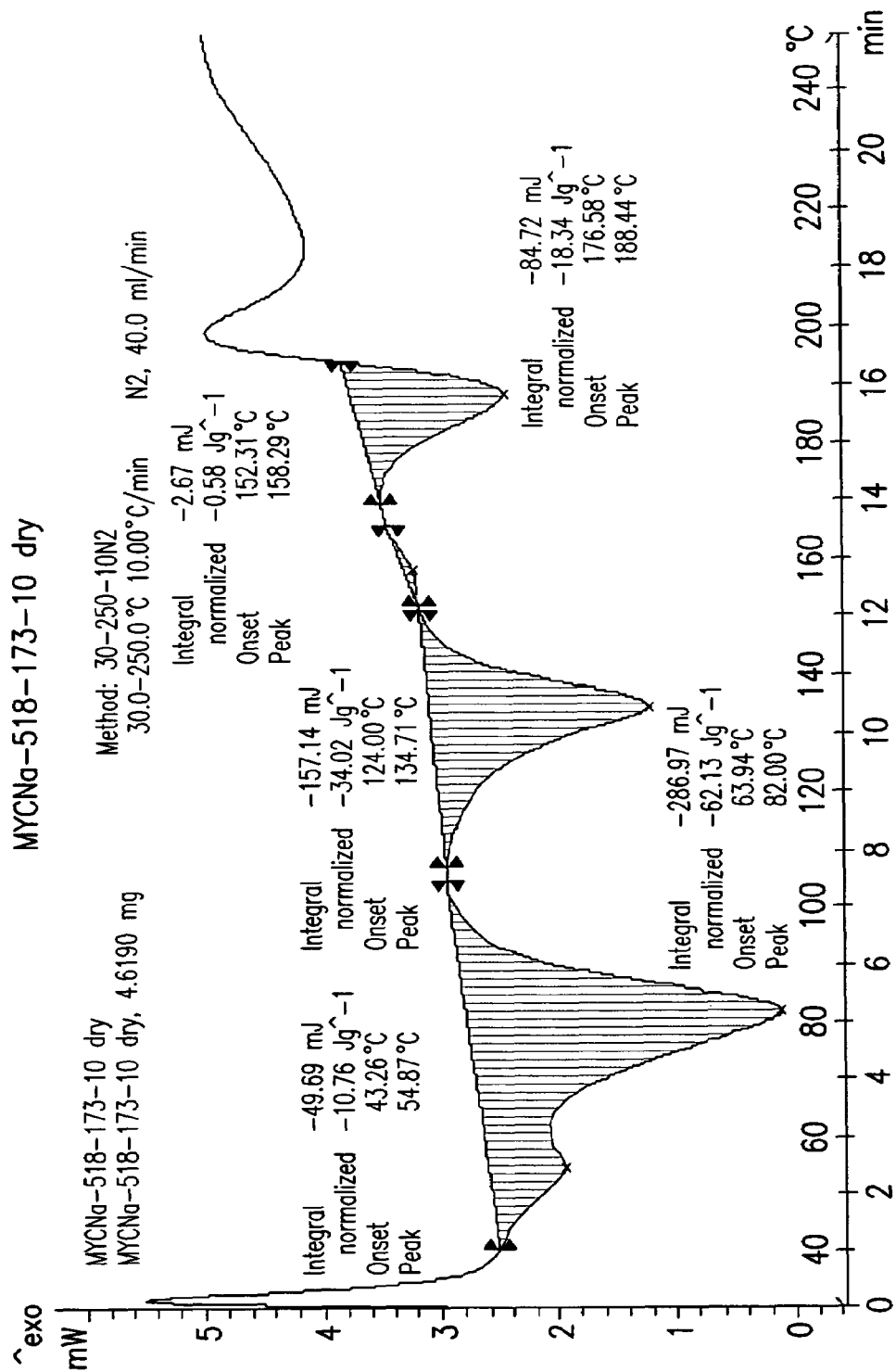
FIG. 50 is a characteristic DSC curve for monosodium mycophenolate form M9.

In another aspect, the present invention is a crystalline mycophenolate sodium, denominated M9, characterized by a powder XRD pattern with peaks at 5.6, 6.0, 7.5 and 9.9±0.2 degrees 2 theta (FIG. 12). Form M9 may be further characterized by XRD peaks at 5.1, 11.9, 13.7, 16.4 and 19.1±0.2 degrees 2 theta. Form M9 may be substantially free of other crystalline forms of Mycophenolate sodium. The DSC curve of form M9 shows several endothermic peaks that are accompanied by weight loss and a last melting peak at 188° C. (FIG. 50). Weight loss is 3.9% as measured by TGA. (KF=4.5%). Form M9 is a monohydrate.

The invention provides a process for preparing mycophenolate sodium Form M9. Sodium mycophenolate Form M9 is obtained by precipitation from a $C_1$ to $C_4$ alcohol, preferably methanol, with use of methylene chloride as an antisolvent. Preferably, methylene chloride is added to a solution of mycophenolate sodium in methanol. The crystalline form may be recovered by conventional techniques.

Form M10

Figure 13:
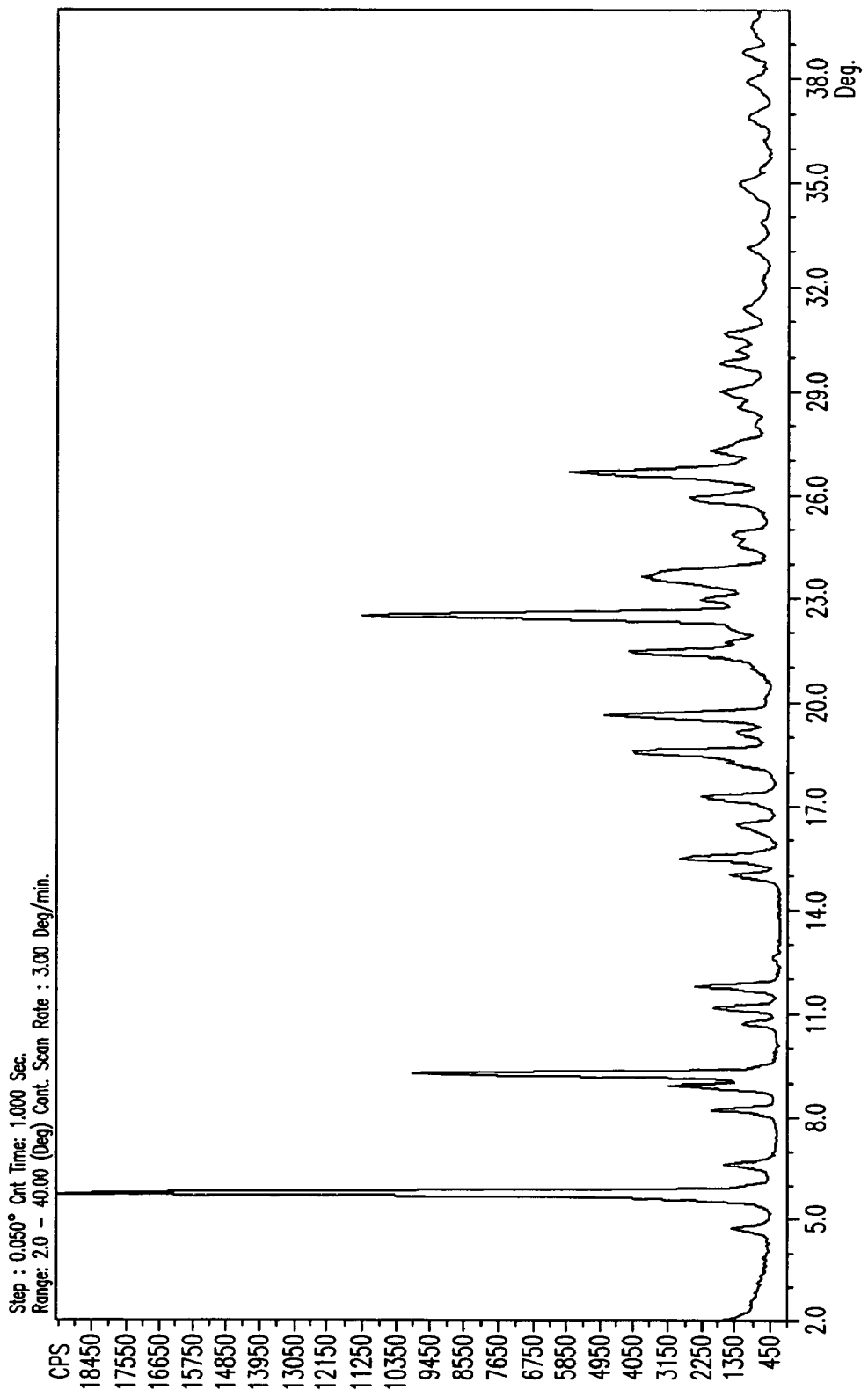
FIG. 13 is a characteristic X-ray powder diffraction pattern for monosodium mycophenolate form M10.
Figure 51:
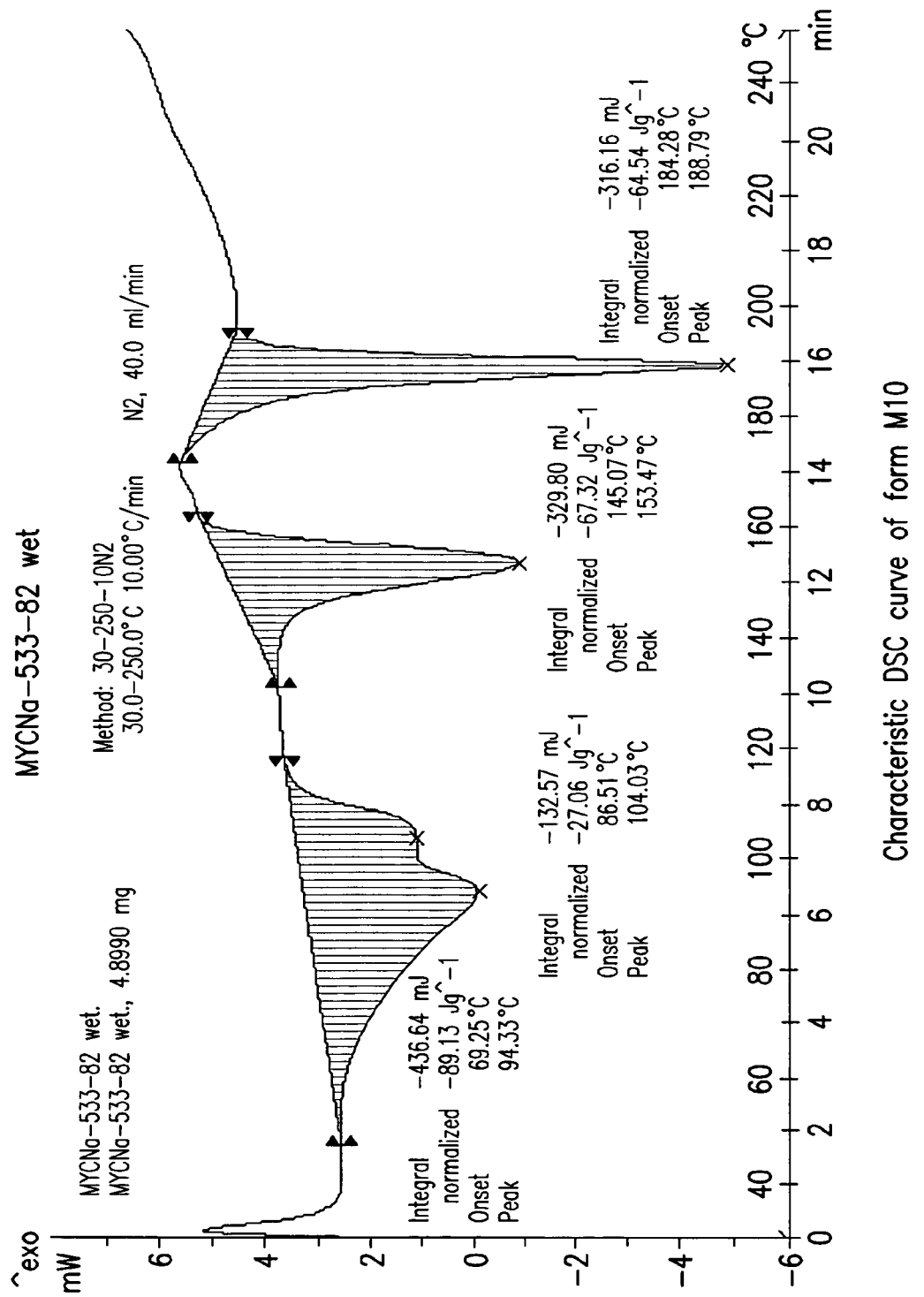
FIG. 51 is a characteristic DSC curve for monosodium mycophenolate form M10.

In another aspect, the present invention is a crystalline mycophenolate sodium, denominated Form M10, characterized by a powder XRD pattern with peaks at 5.8, 9.0, 9.3, and 19.7±0.2 degrees 2 theta (FIG. 13). Form M10 may be further characterized by XRD peaks at 5.1, 11.8, 15.5 17.3, and 18.6±0.2 degrees 2 theta. Form M10 may be substantially free of other crystalline forms of mycophenolate sodium. The DSC curve of Form M10, which is a wet sample, has an endothermic peak caused by the evaporation of the acetonitrile, has an endothermic peak due to water loss, and two melting peaks in the range of about 152-153° C. and about 189-192° C. (FIG. 51). Weight loss is about 9.8% as measured by TGA. (KF=1.6%). Form M10 is an acetonitrile monosolvate.

Mycophenolate sodium Form M10 may be prepared by precipitation from acetonitrile. In one embodiment, mycophenolic acid is dissolved in acetonitrile, and a base and a source of sodium is added to the solution to precipitate the crystalline form. Finally, the crystalline form is recovered.

Form M11

Figure 14:
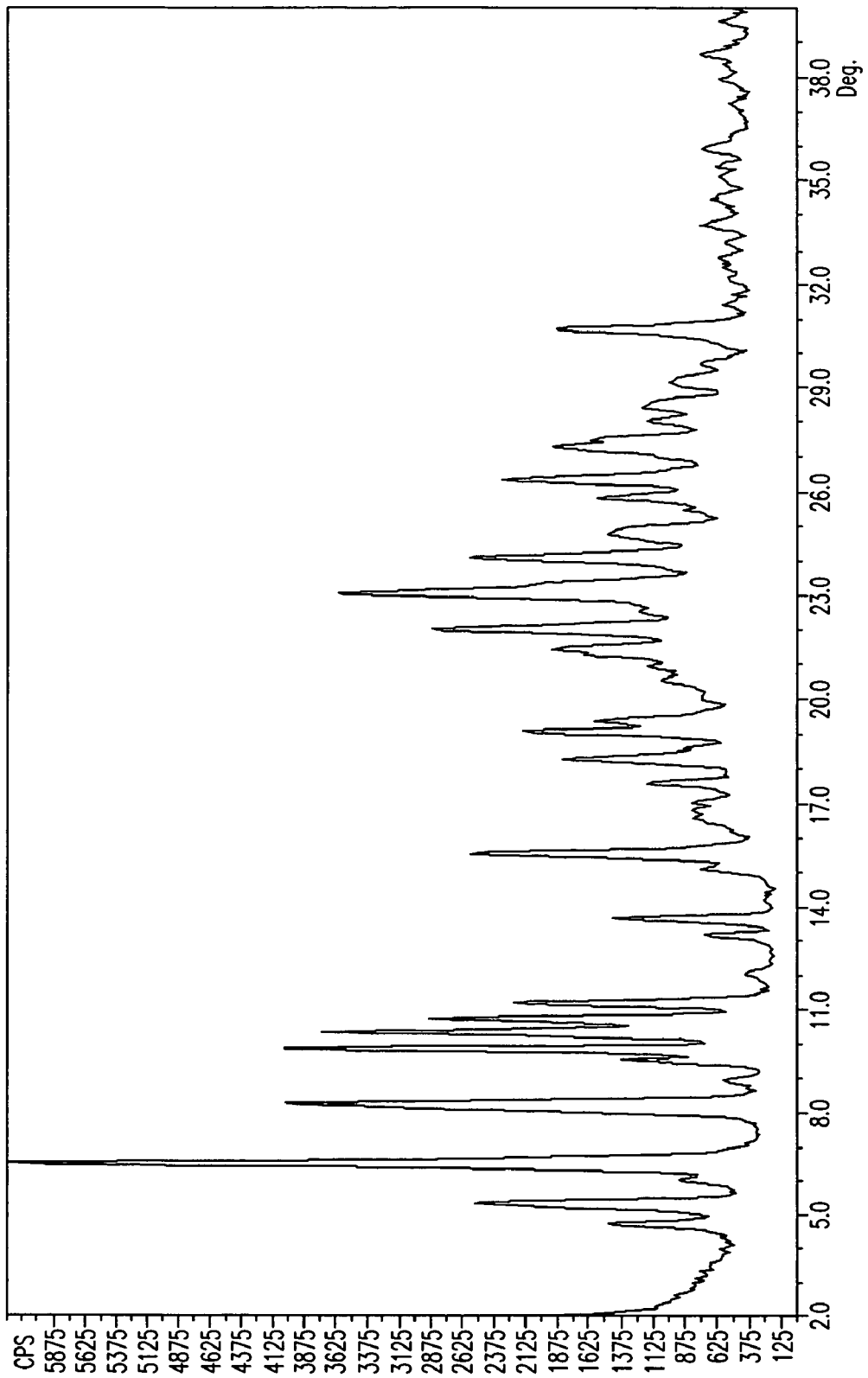
FIG. 14 is a characteristic X-ray powder diffraction pattern for monosodium mycophenolate form M11.
Figure 15:
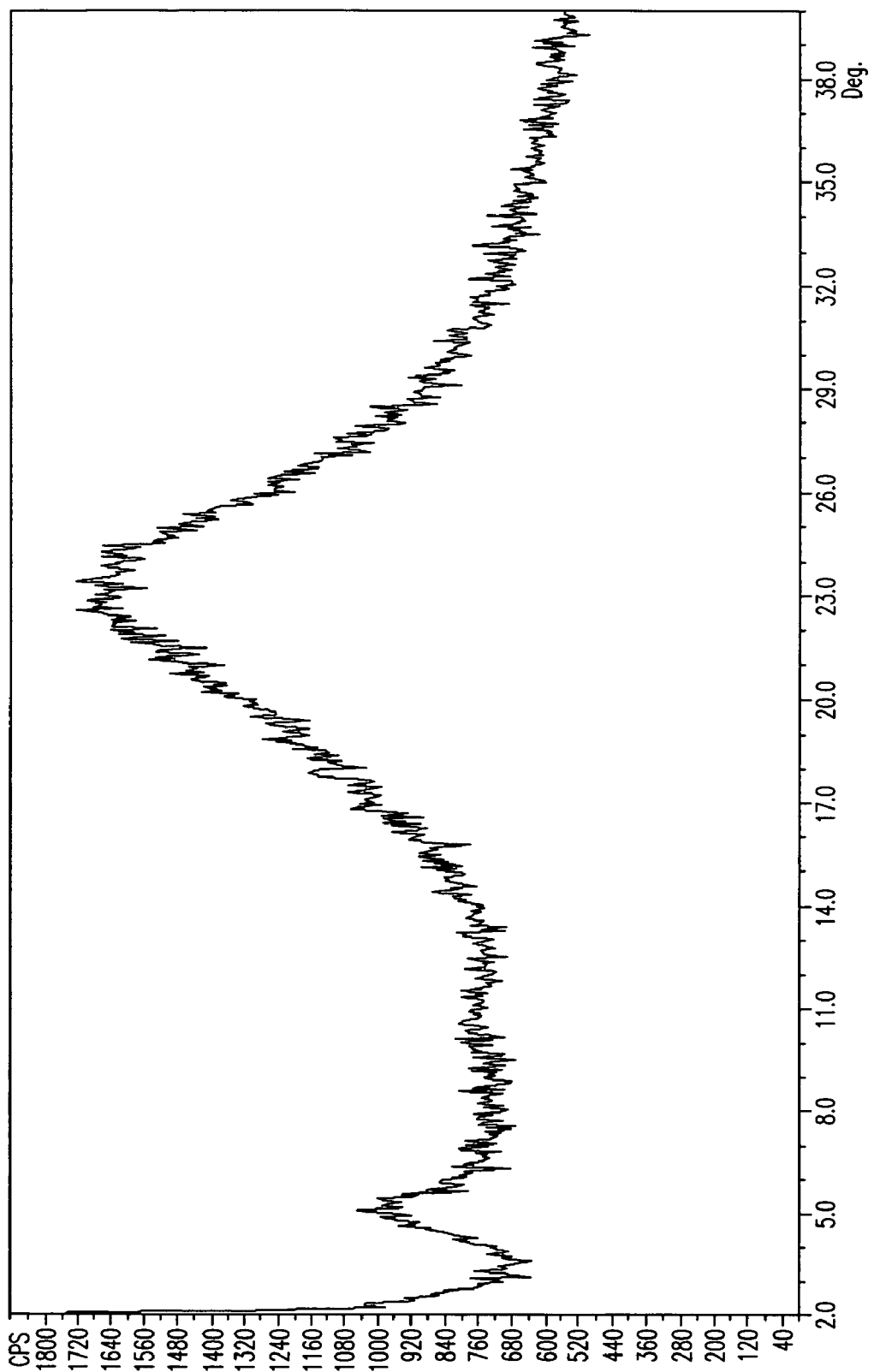
FIG. 15 is a characteristic X-ray powder diffraction pattern for monosodium mycophenolate form M12.
Figure 52:
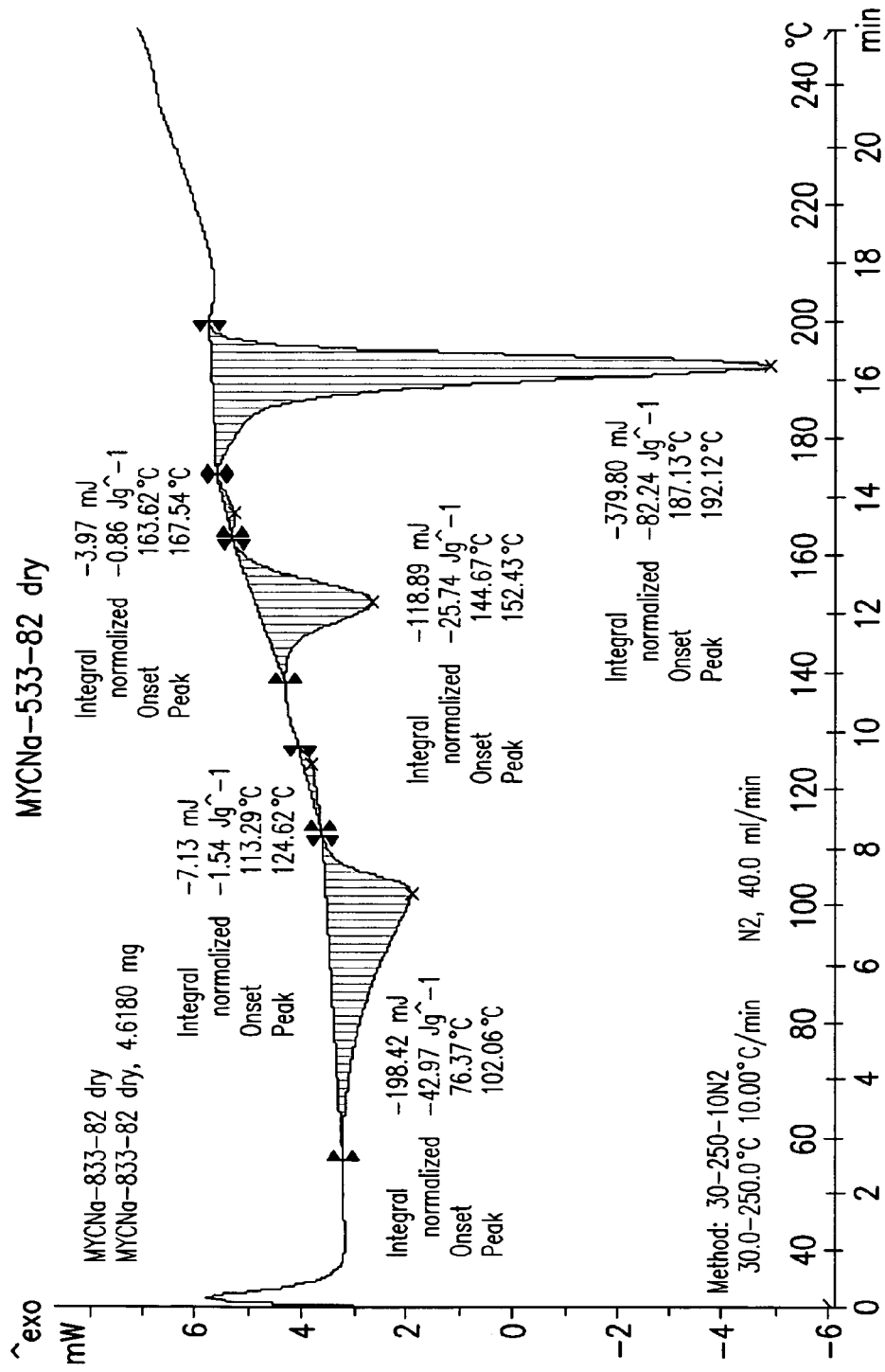
FIG. 52 is a characteristic DSC curve for monosodium mycophenolate form M11.

In another aspect, the present invention is a crystalline mycophenolate sodium, denominated Form M11, characterized by a powder XRD pattern with a peak 10.3±0.2 degrees 2 theta (FIG. 14). Form M11 may be further characterized by XRD peaks at 4.7, 5.3, 6.5, 8.2, 9.9, 15.5 and 19.1±0.2 degrees 2 theta. Form M11 may be substantially free of other crystalline forms of mycophenolate sodium. The DSC curve of Form M11 has an endothermic peak due to water loss, and two melting peaks in the range of 152-153° C. and 189-192° C. (FIG. 52). Weight loss is 1.5% as measured by TGA. Form M11 is a solvated form.

Form M11 may be obtained by drying the precipitate obtained from the process of Form M10. The precipitate may be dried, preferably at 30° C. to about 50° C., more preferably about 40° C. to about 45° C., most preferably at a pressure below about 100 mmHg.

Form M12

Figure 16:
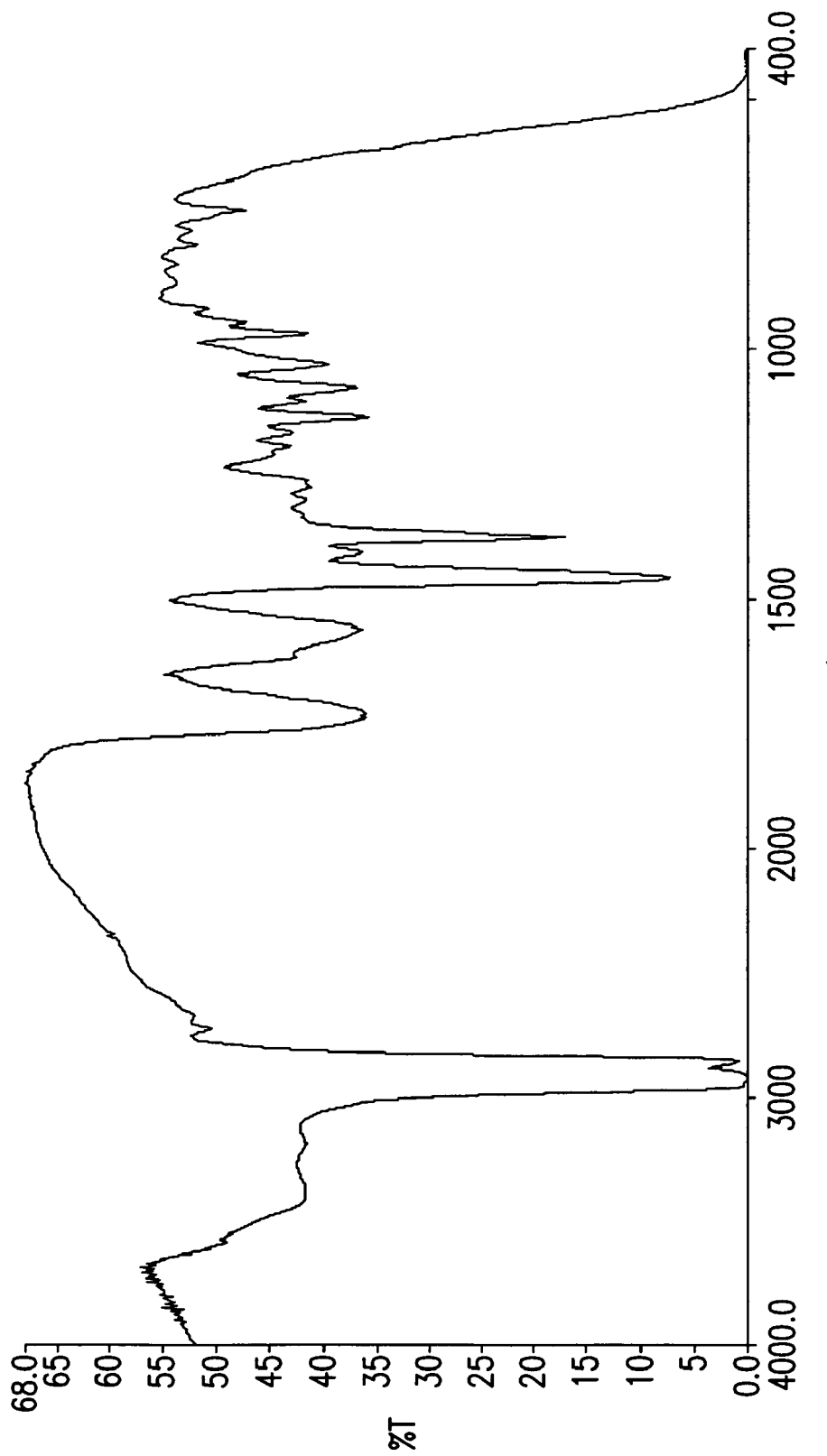
FIG. 16 is a characteristic FT-IR spectrum for monosodium mycophenolate form M12.
Figure 53:
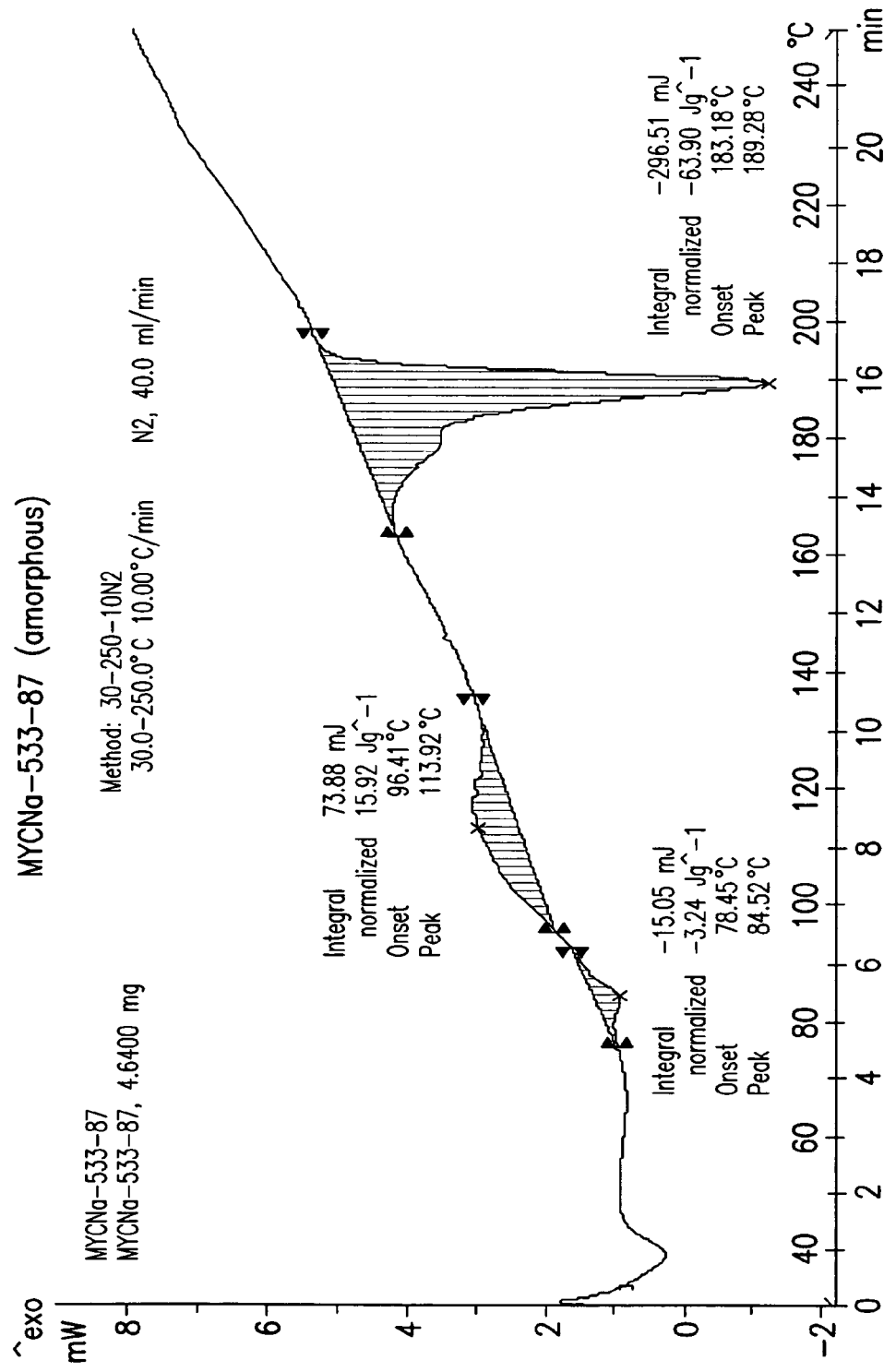
FIG. 53 is a characteristic DSC curve for monosodium mycophenolate amorphous M12.
Figure 54:
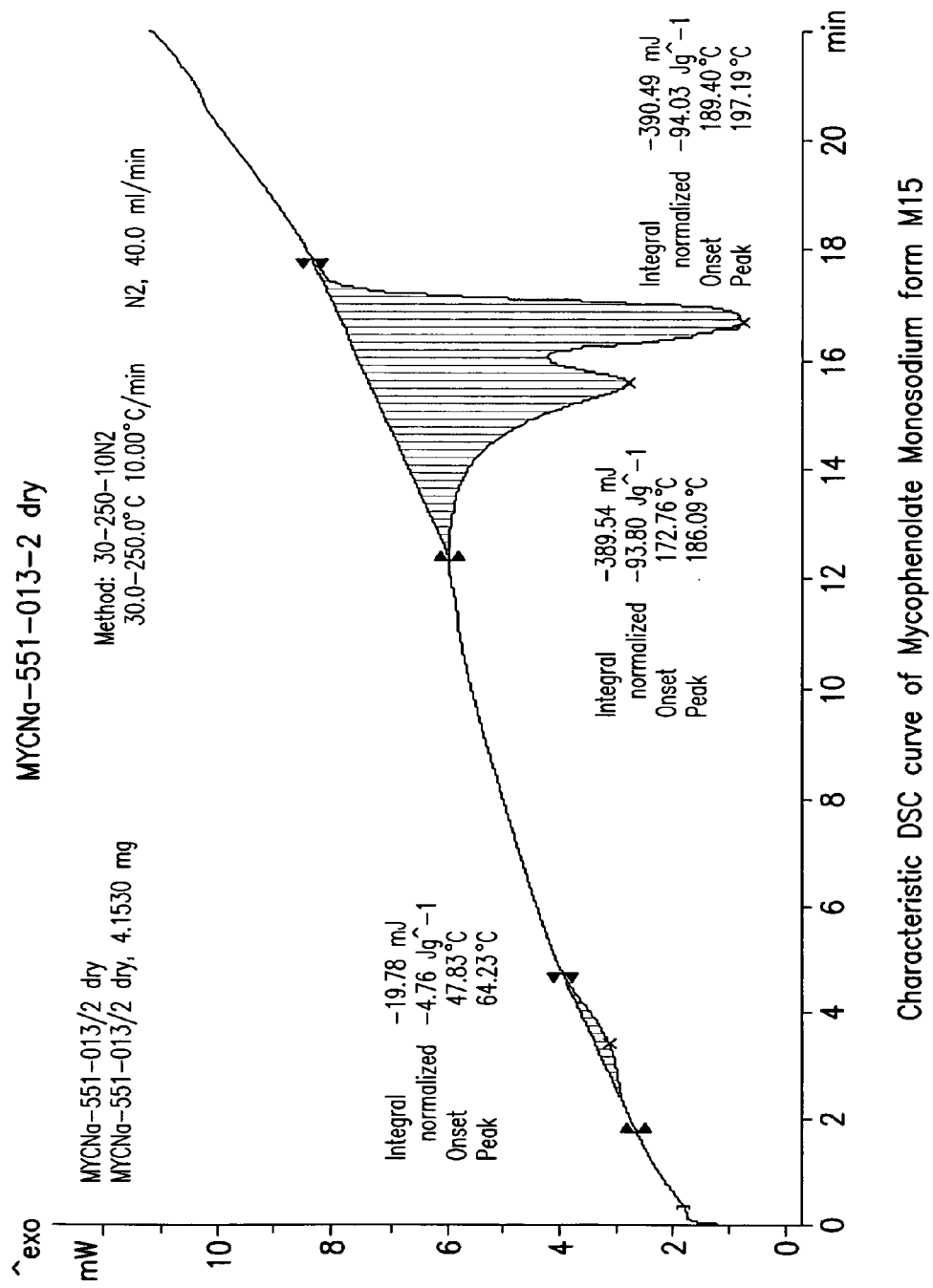
FIG. 54 is a characteristic DSC curve for monosodium mycophenolate form M15.
Figure 55:
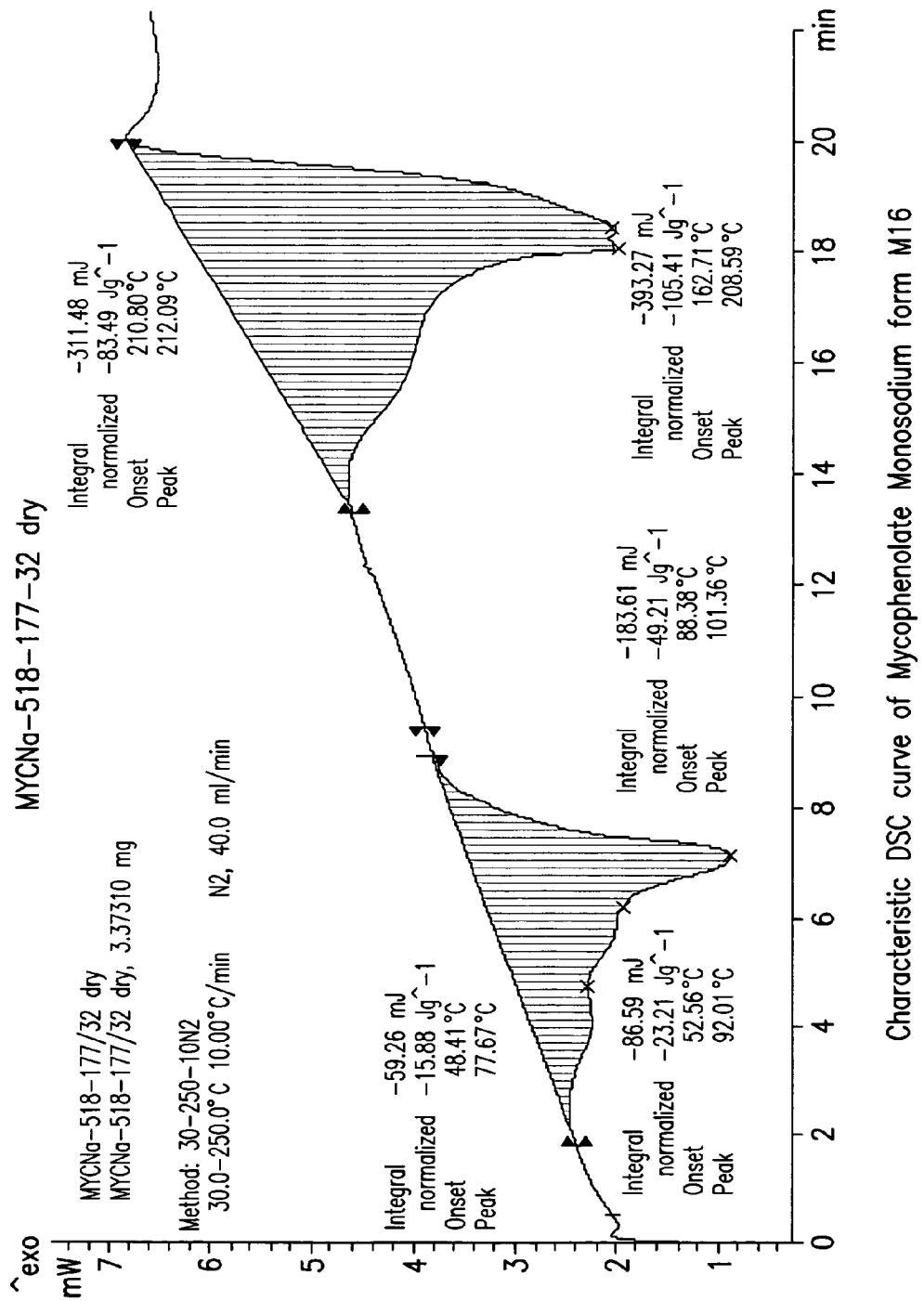
FIG. 55 is a characteristic DSC curve for monosodium mycophenolate form M16.
Figure 56:
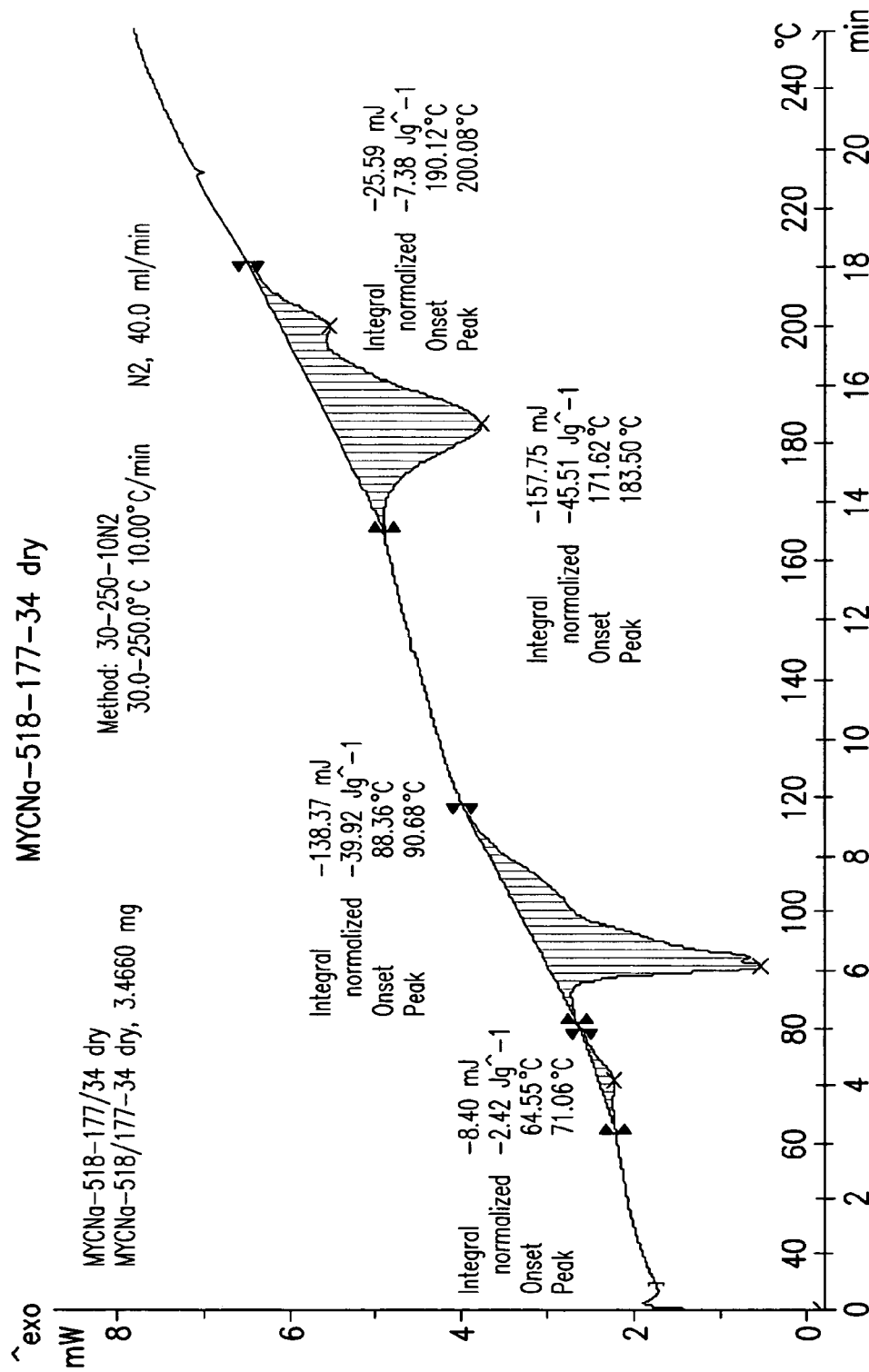
FIG. 56 is a characteristic DSC curve for monosodium mycophenolate form M17.
Figure 57:
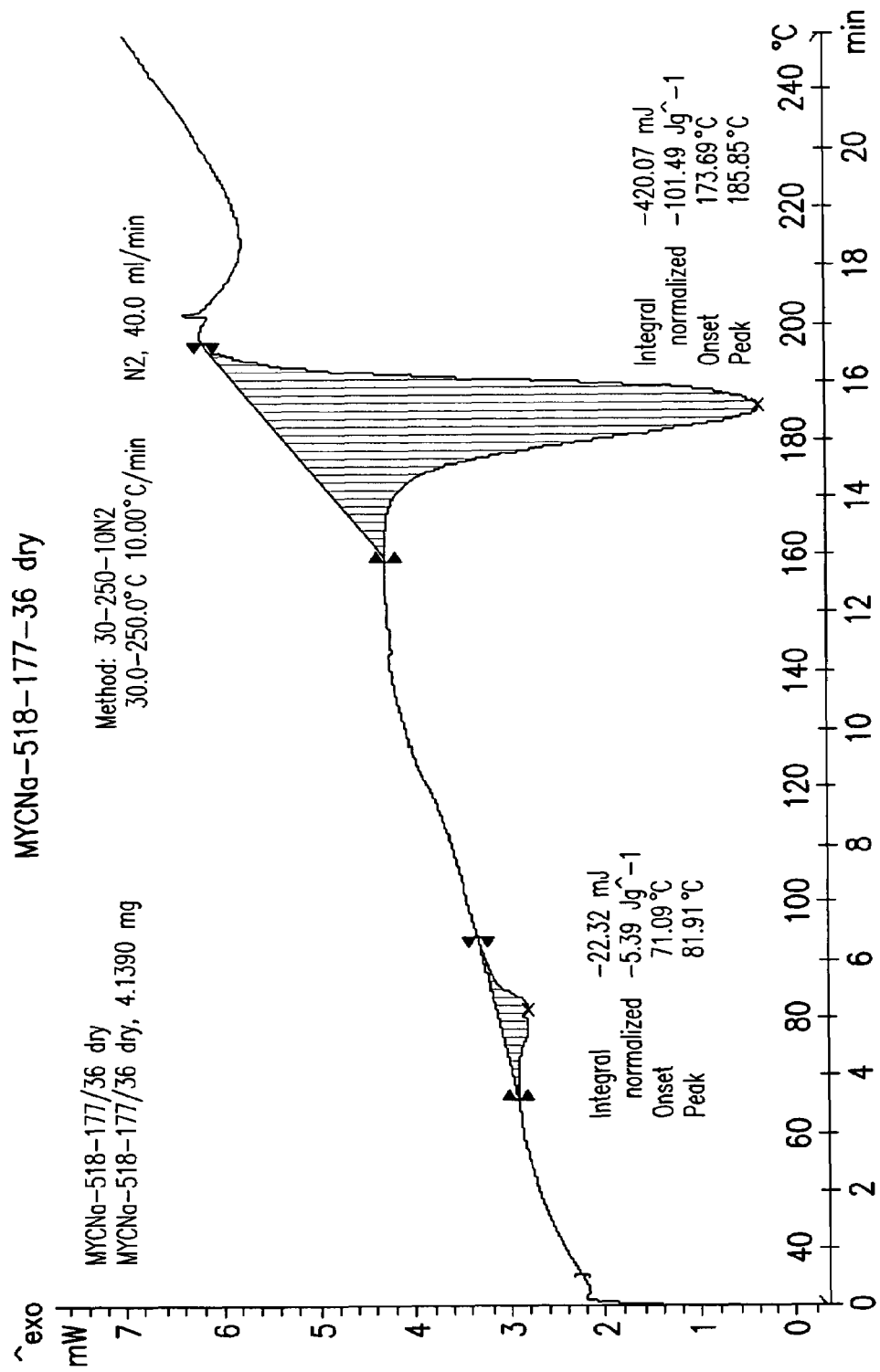
FIG. 57 is a characteristic DSC curve for monosodium mycophenolate form M18.
Figure 58:
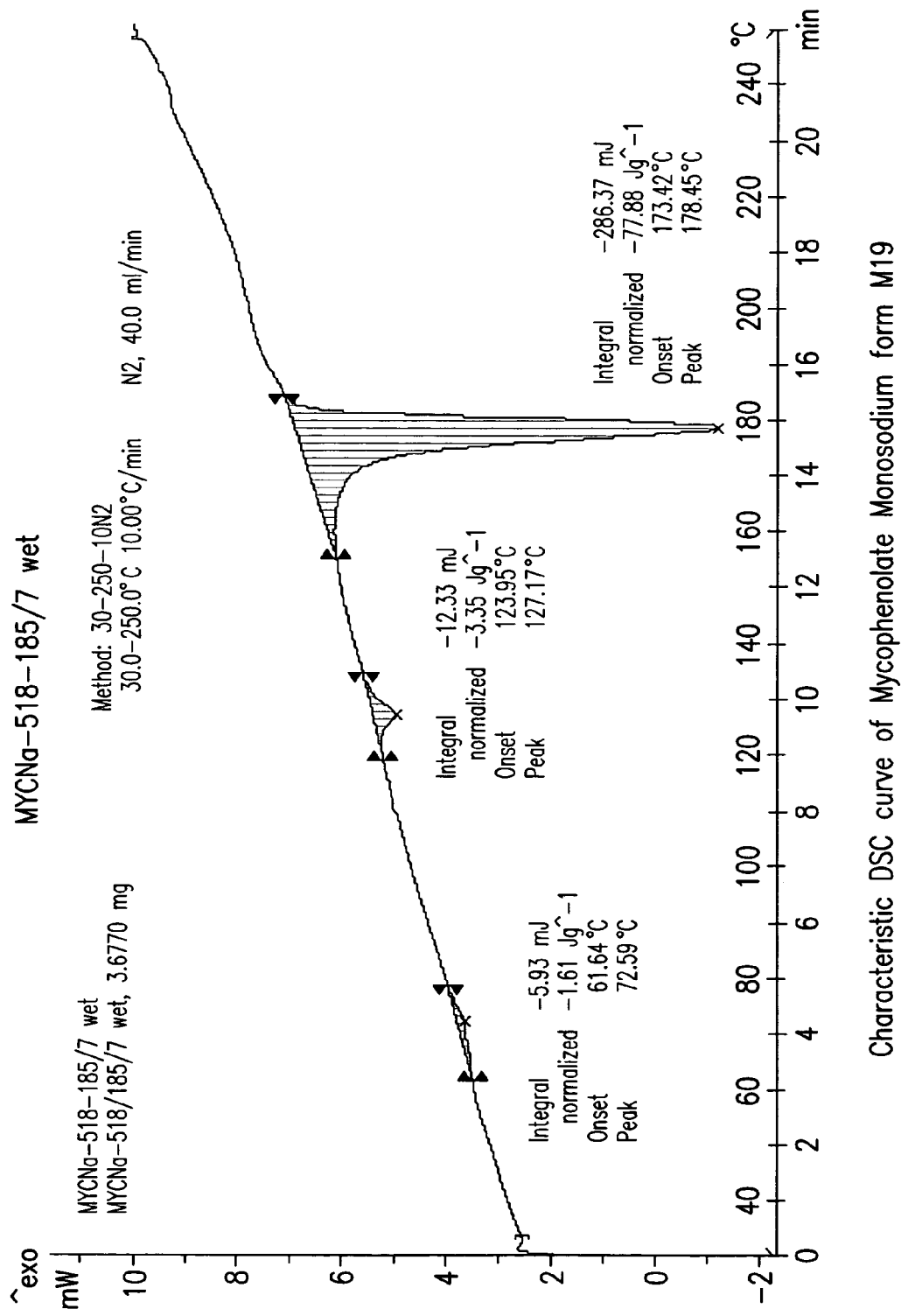
FIG. 58 is a characteristic DSC curve for monosodium mycophenolate form M19.
Figure 59:
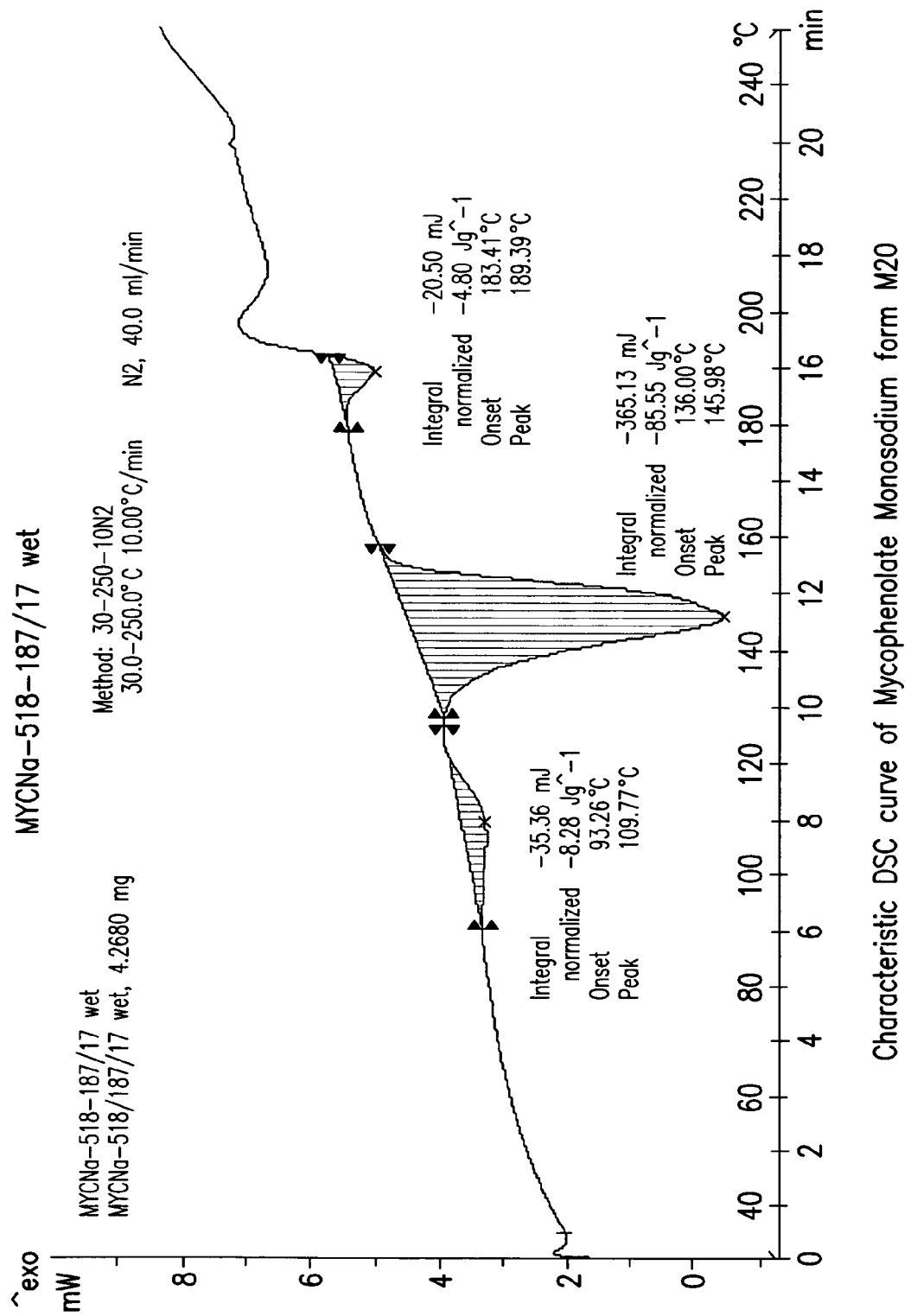
FIG. 59 is a characteristic DSC curve for monosodium mycophenolate form M20.
Figure 60:
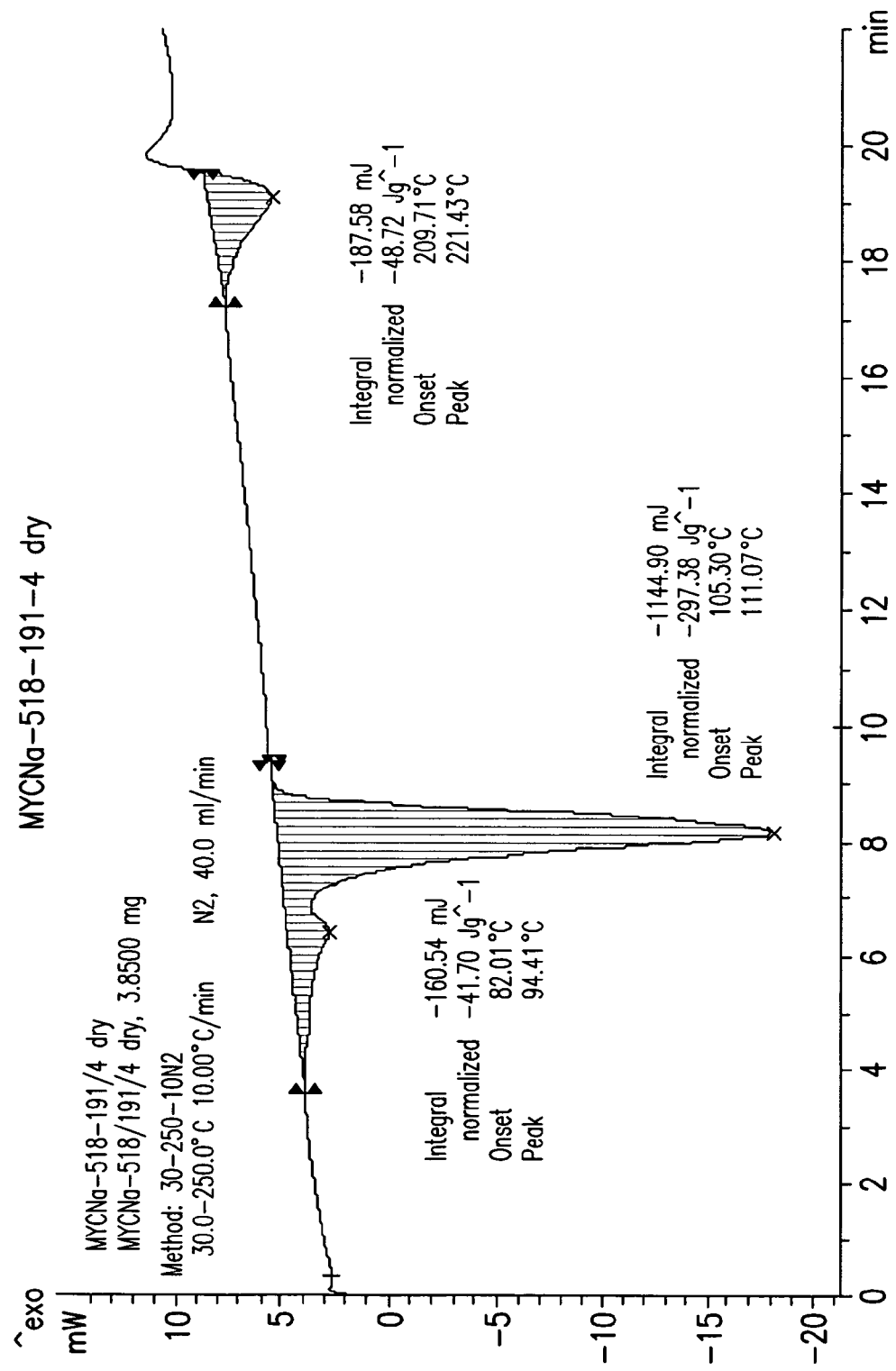
FIG. 60 is a characteristic DSC curve for monosodium mycophenolate form M21.
Figure 61:
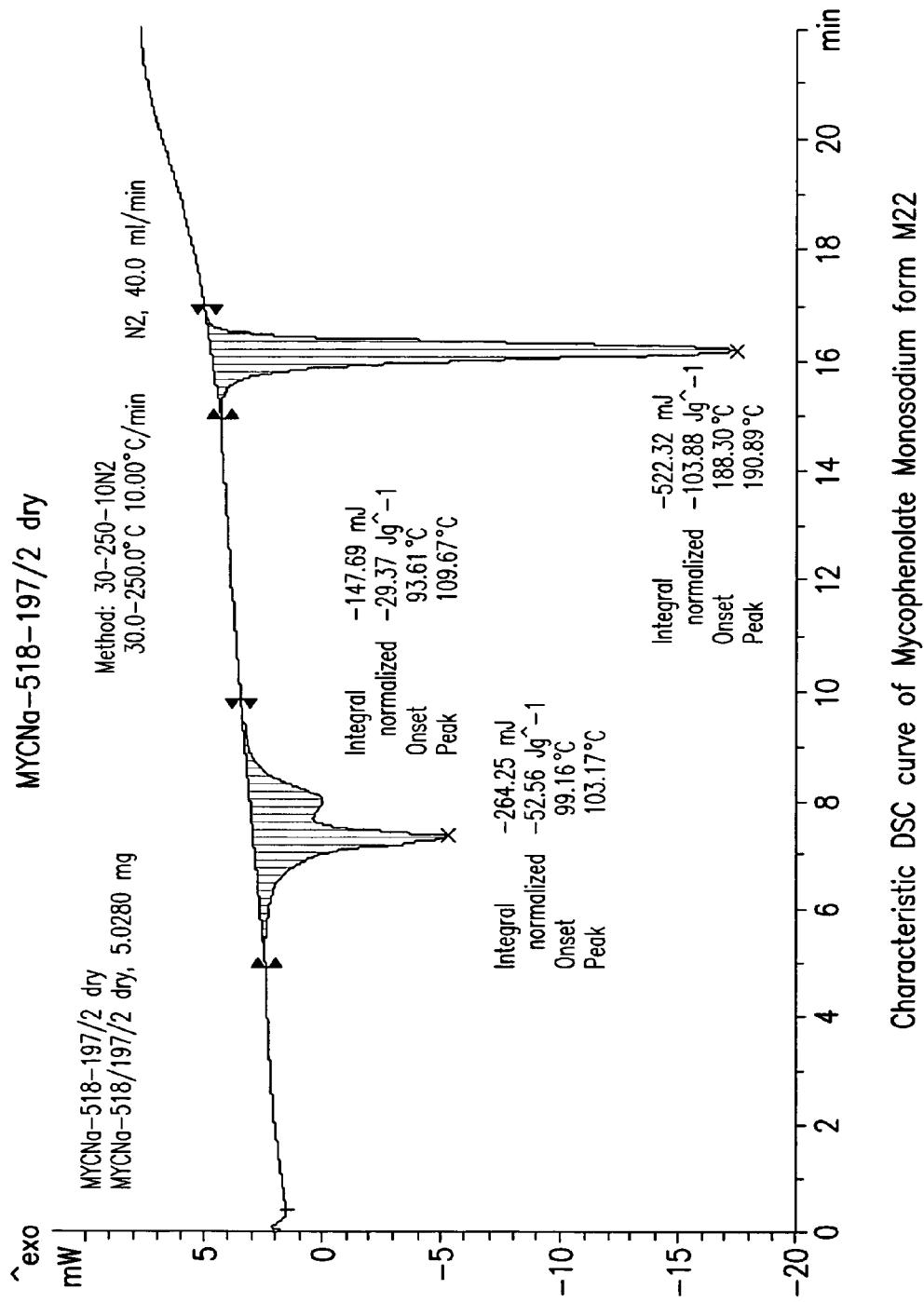
FIG. 61 is a characteristic DSC curve for monosodium mycophenolate form M22.
Figure 62:
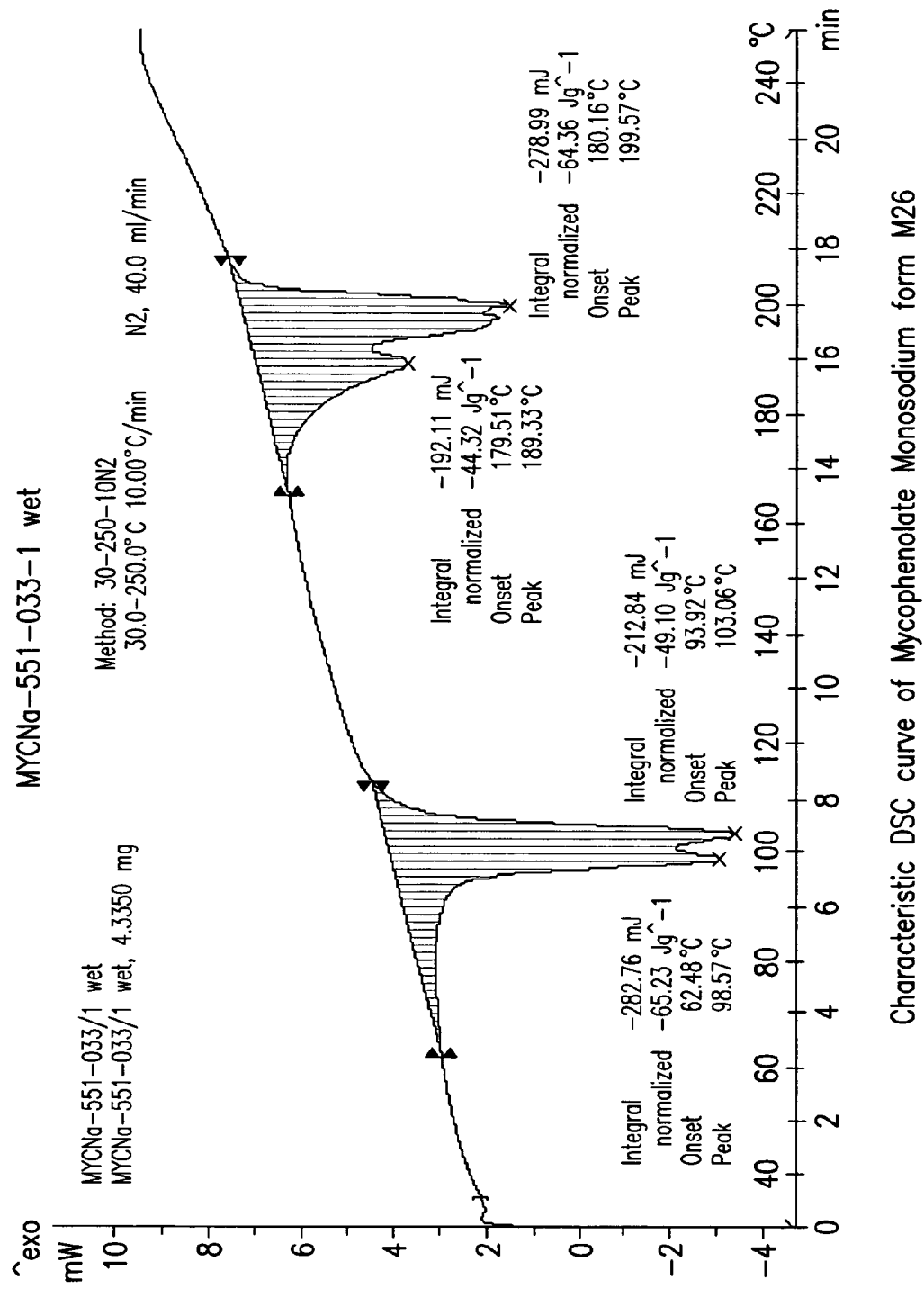
FIG. 62 is a characteristic DSC curve for monosodium mycophenolate form M26.
Figure 63:
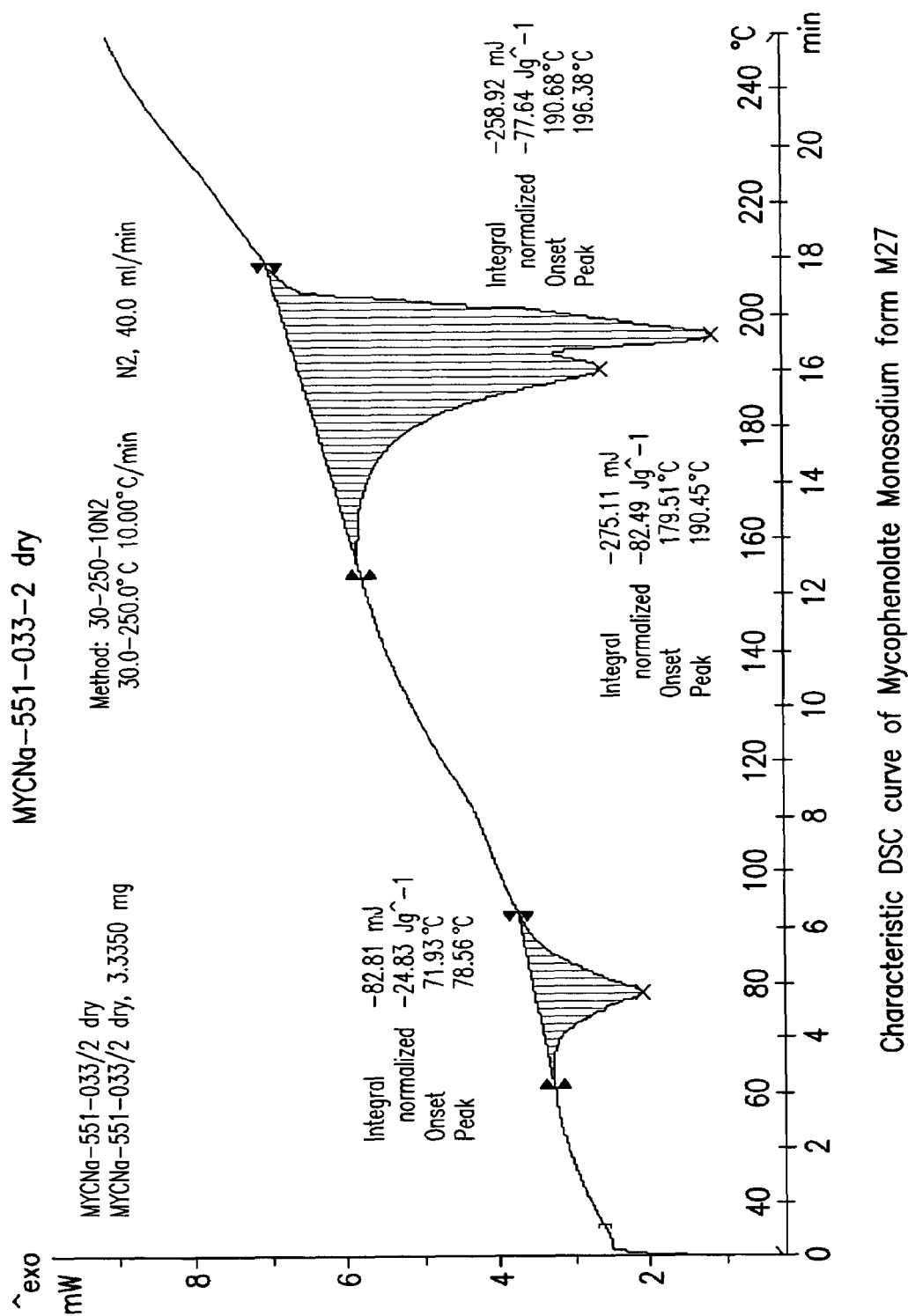
FIG. 63 is a characteristic DSC curve for monosodium mycophenolate form M27.
Figure 64:
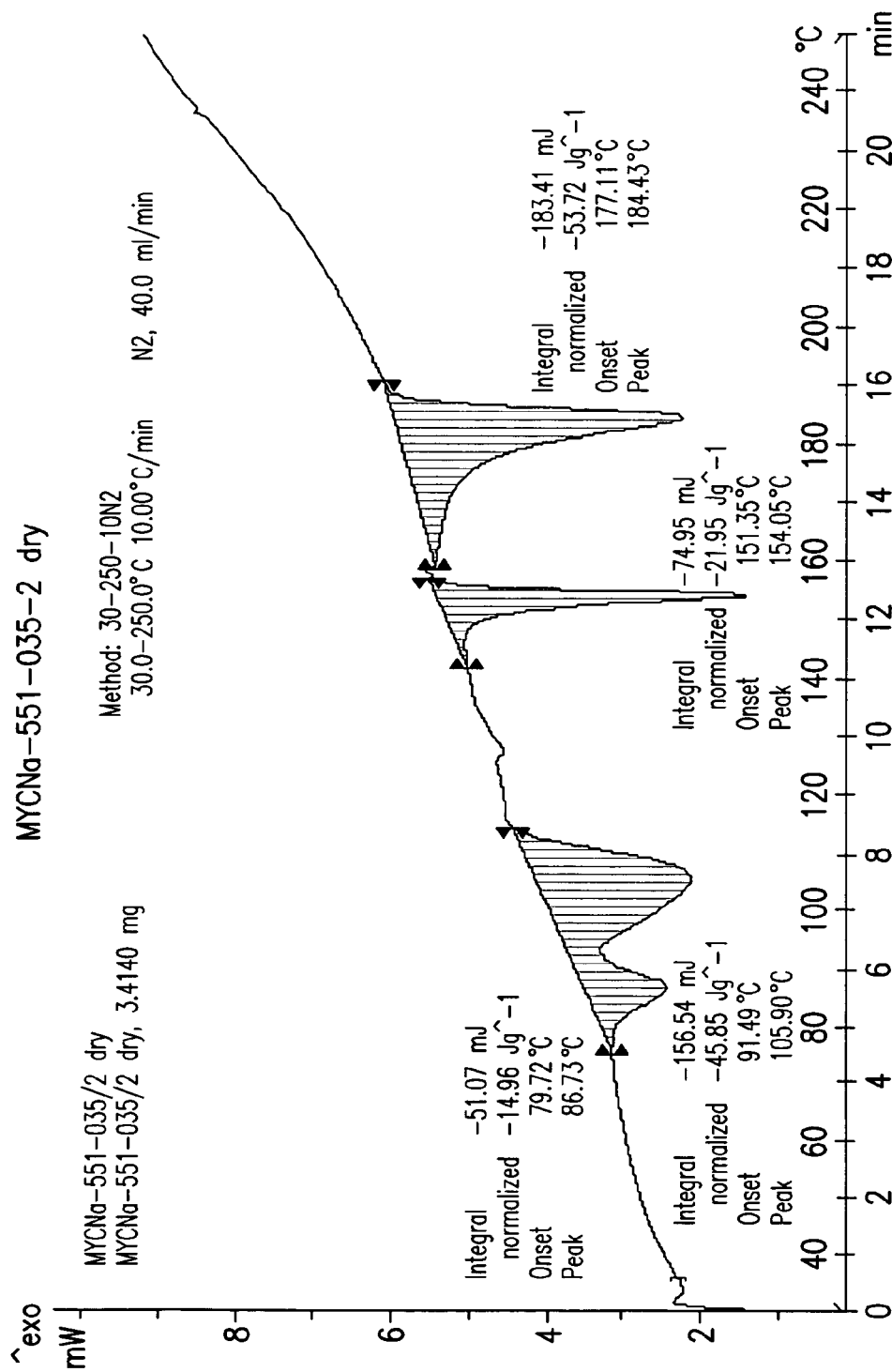
FIG. 64 is a characteristic DSC curve for monosodium mycophenolate form M28.
Figure 65:
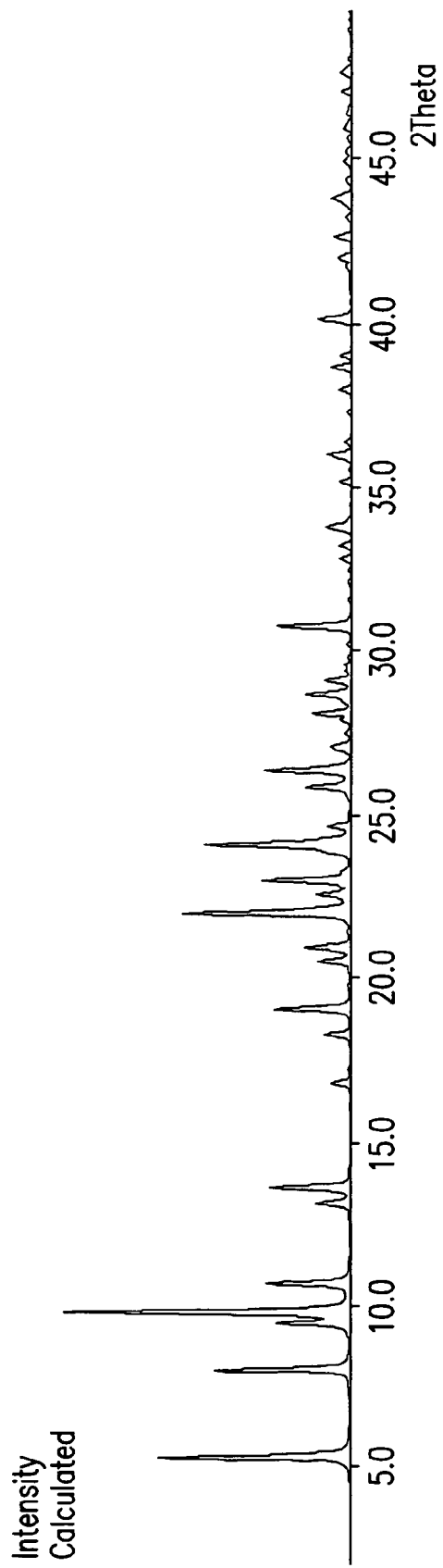
FIG. 65 is a calculated XRD pattern of a single crystal data of Article Acta Crystallographica Sect. C, (2000), C56, 432-434.
Figure 66:
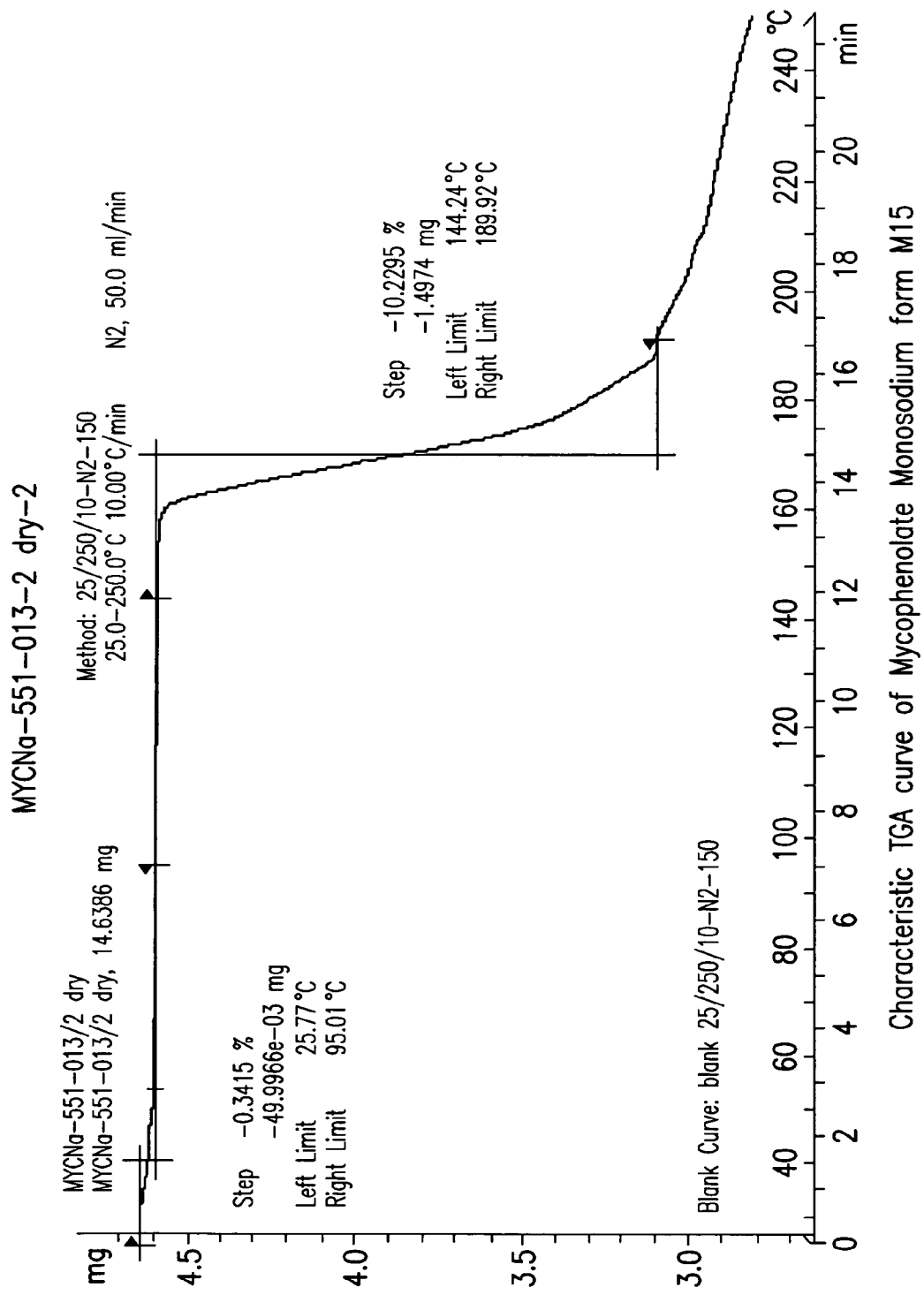
FIG. 66 is a characteristic TGA curve for monosodium mycophenolate form M15.
Figure 67:
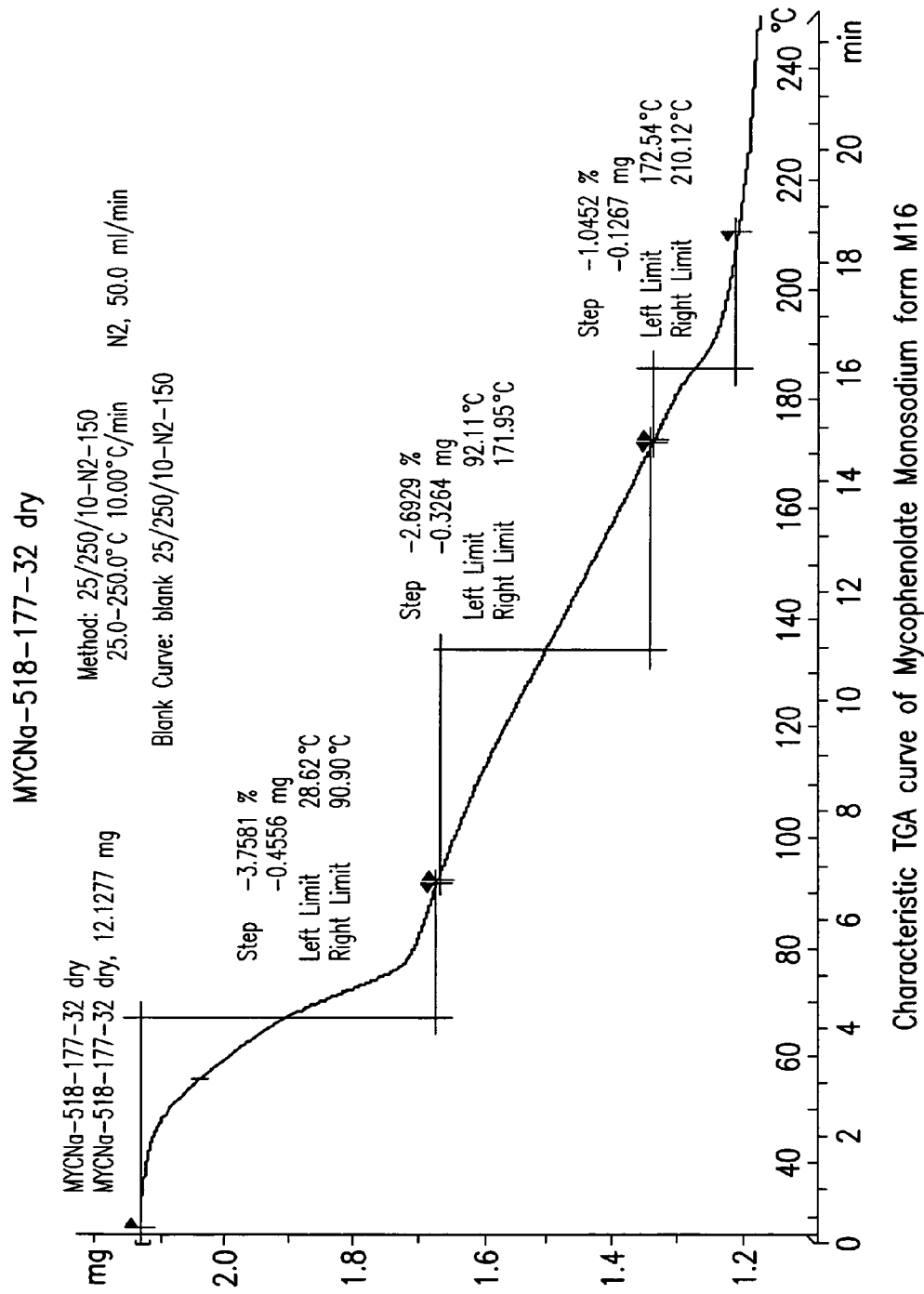
FIG. 67 is a characteristic TGA curve for monosodium mycophenolate form M16.
Figure 68:
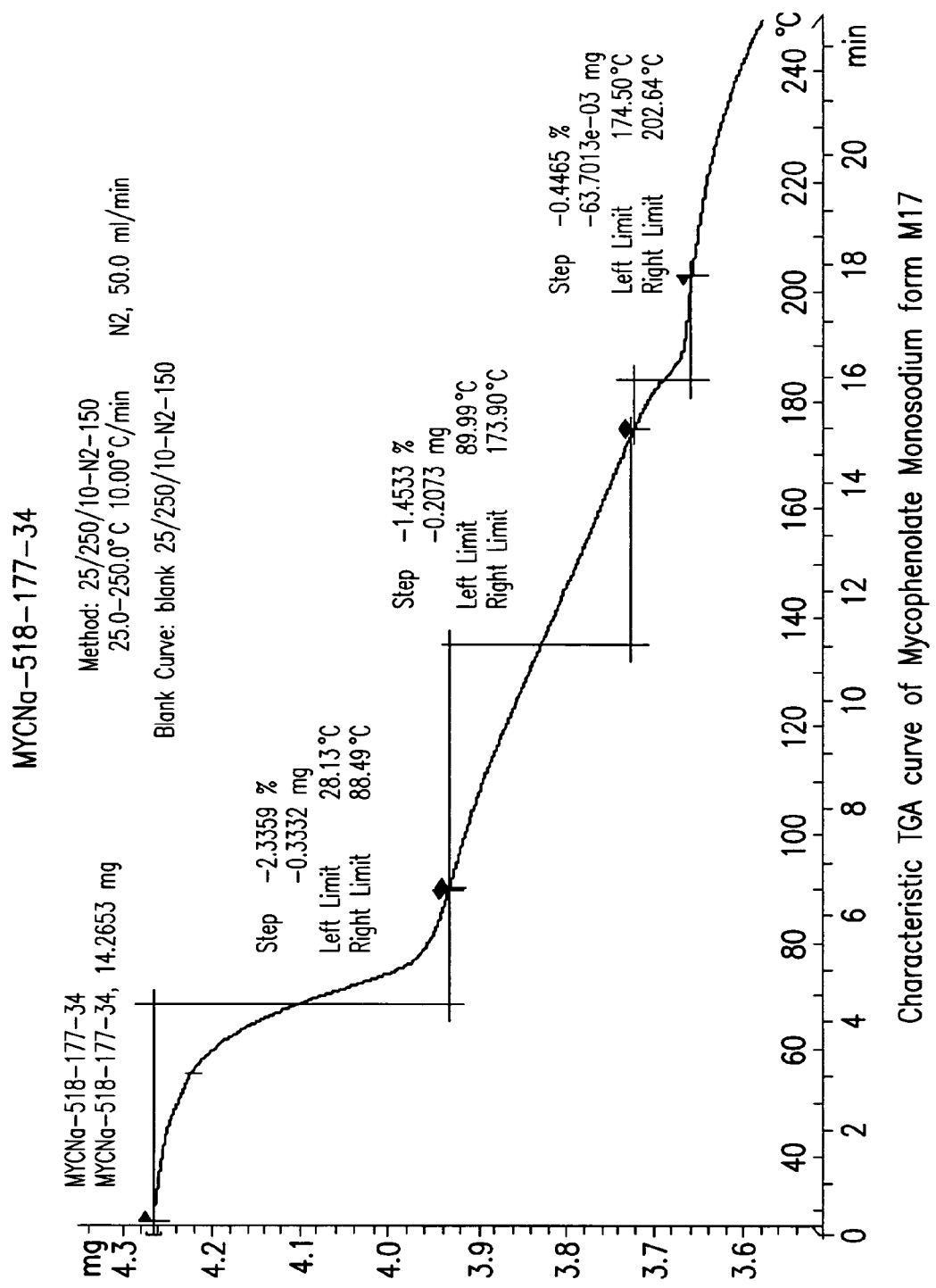
FIG. 68 is a characteristic TGA curve for monosodium mycophenolate form M17.
Figure 69:
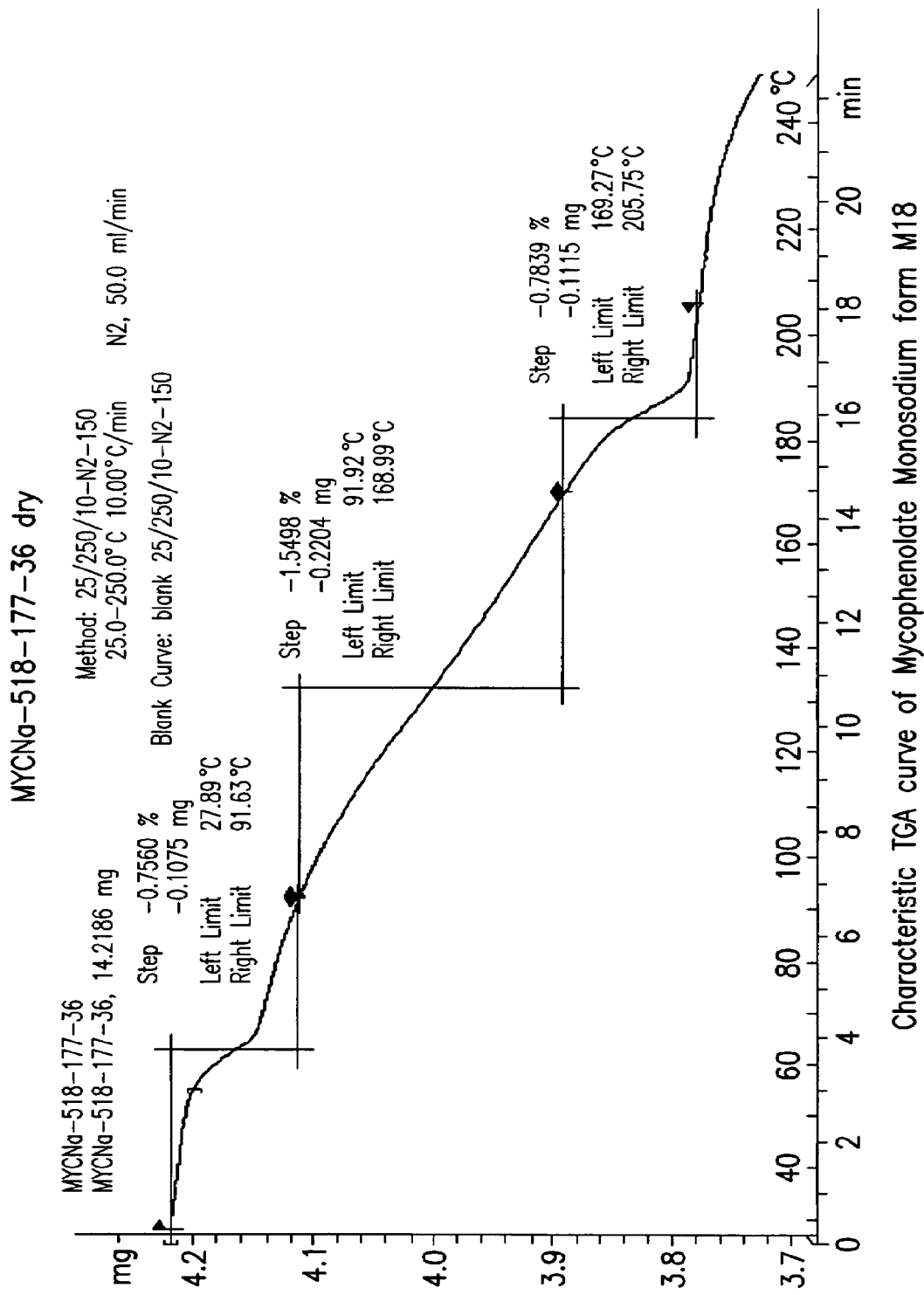
FIG. 69 is a characteristic TGA curve for monosodium mycophenolate form M18.
Figure 70:
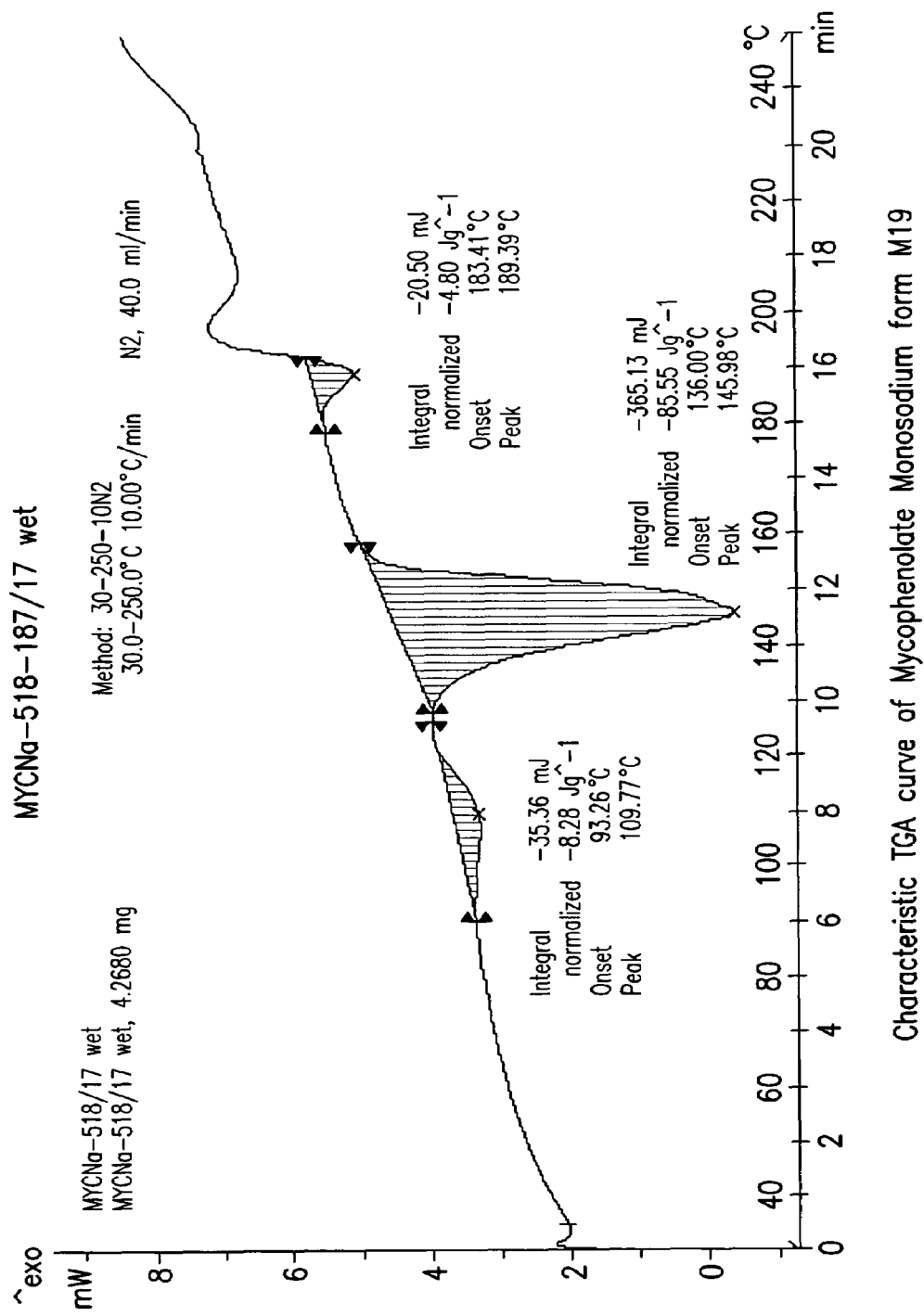
FIG. 70 is a characteristic TGA curve for monosodium mycophenolate form M19.
Figure 71:
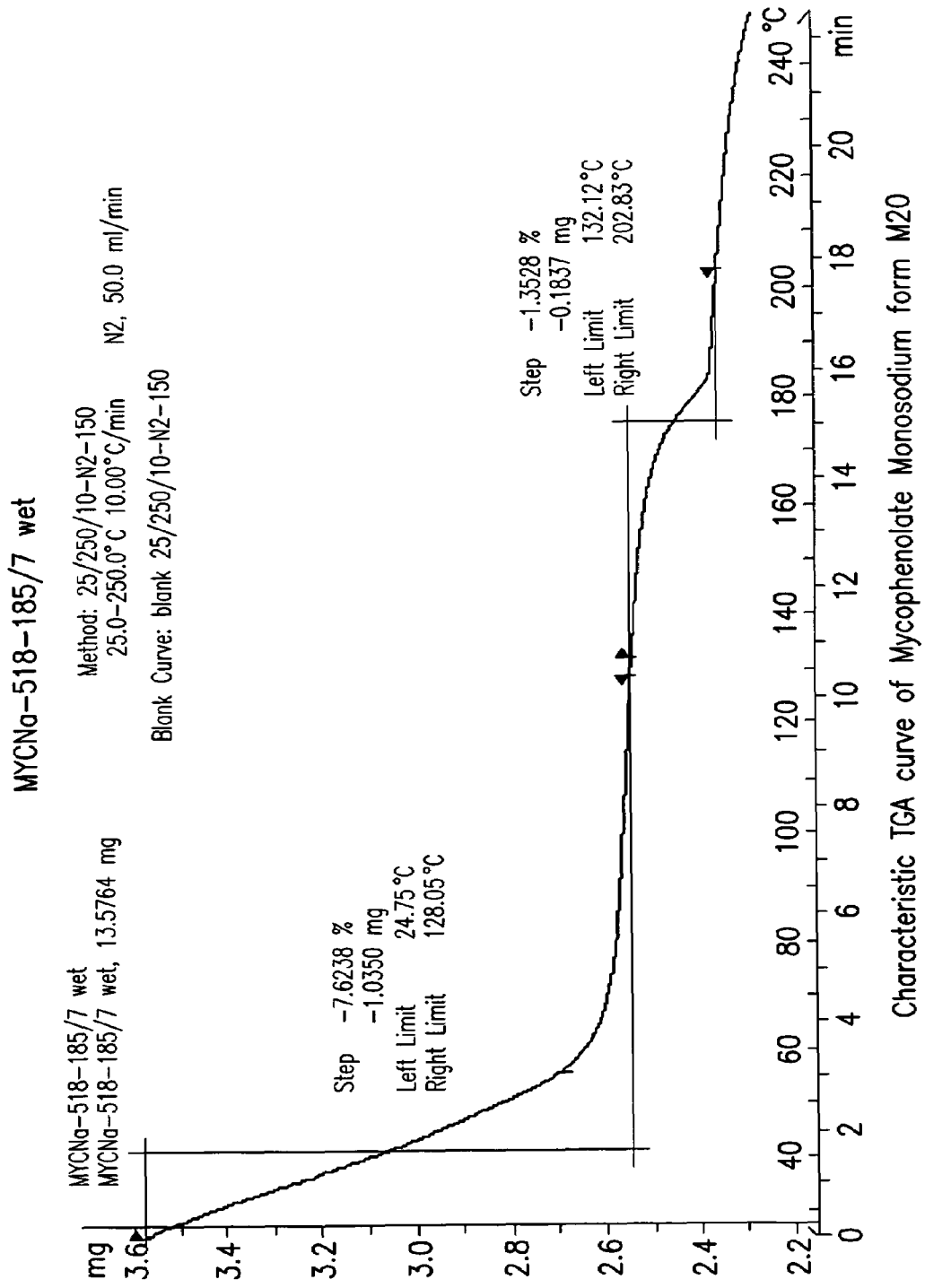
FIG. 71 is a characteristic TGA curve for monosodium mycophenolate form M20.
Figure 72:
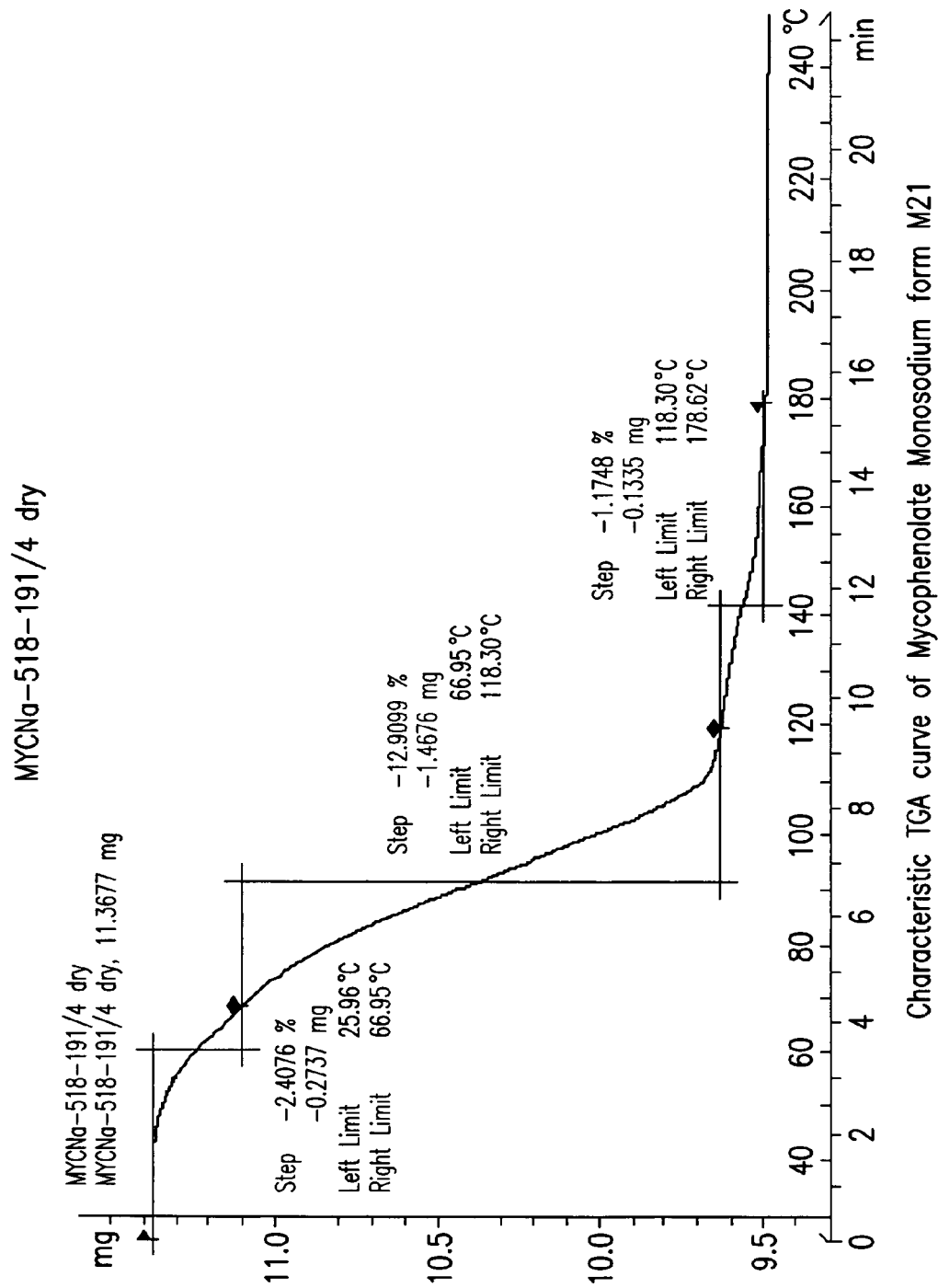
FIG. 72 is a characteristic TGA curve for monosodium mycophenolate form M21.
Figure 73:
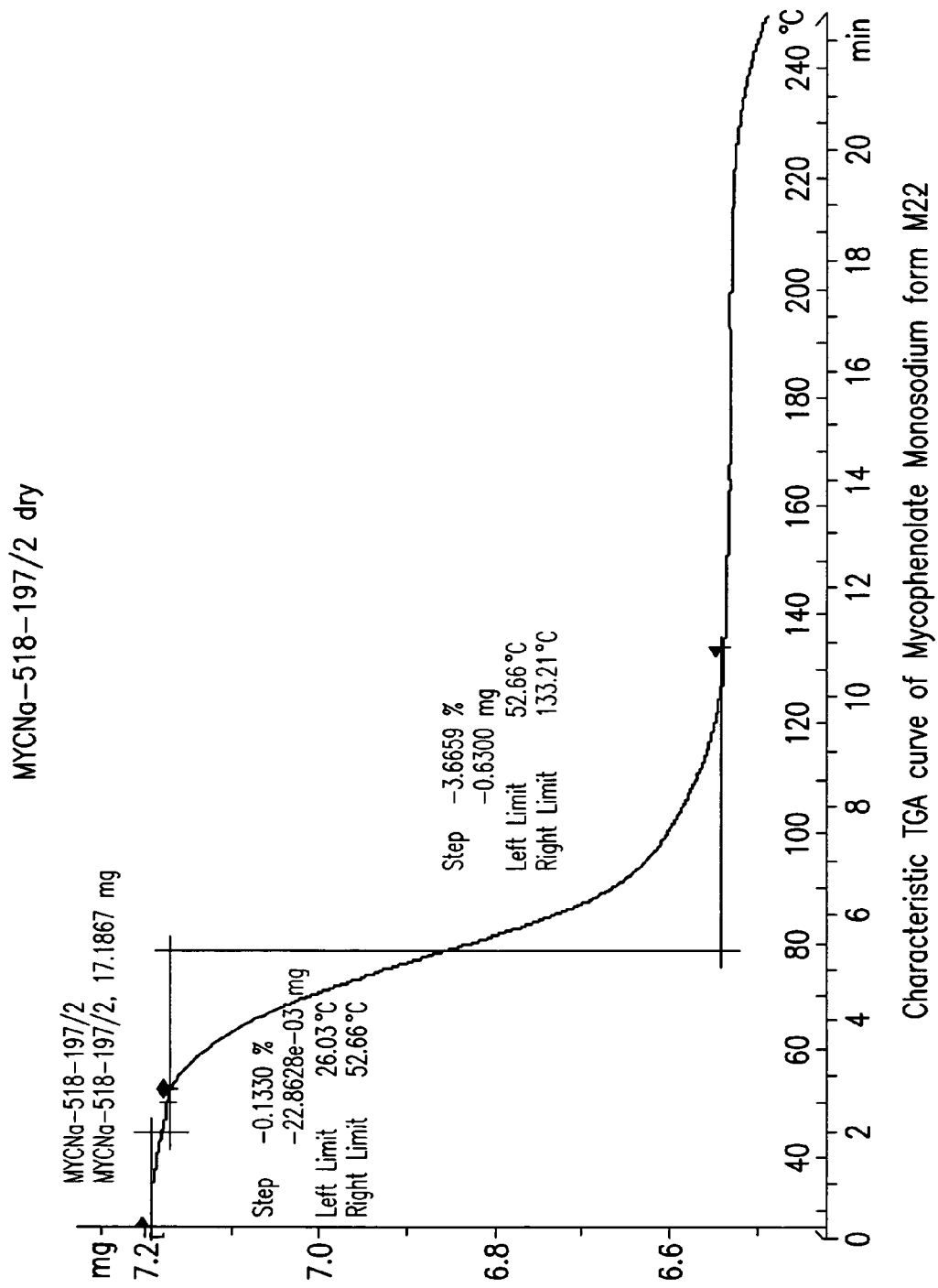
FIG. 73 is a characteristic TGA curve for monosodium mycophenolate form M22.
Figure 74:
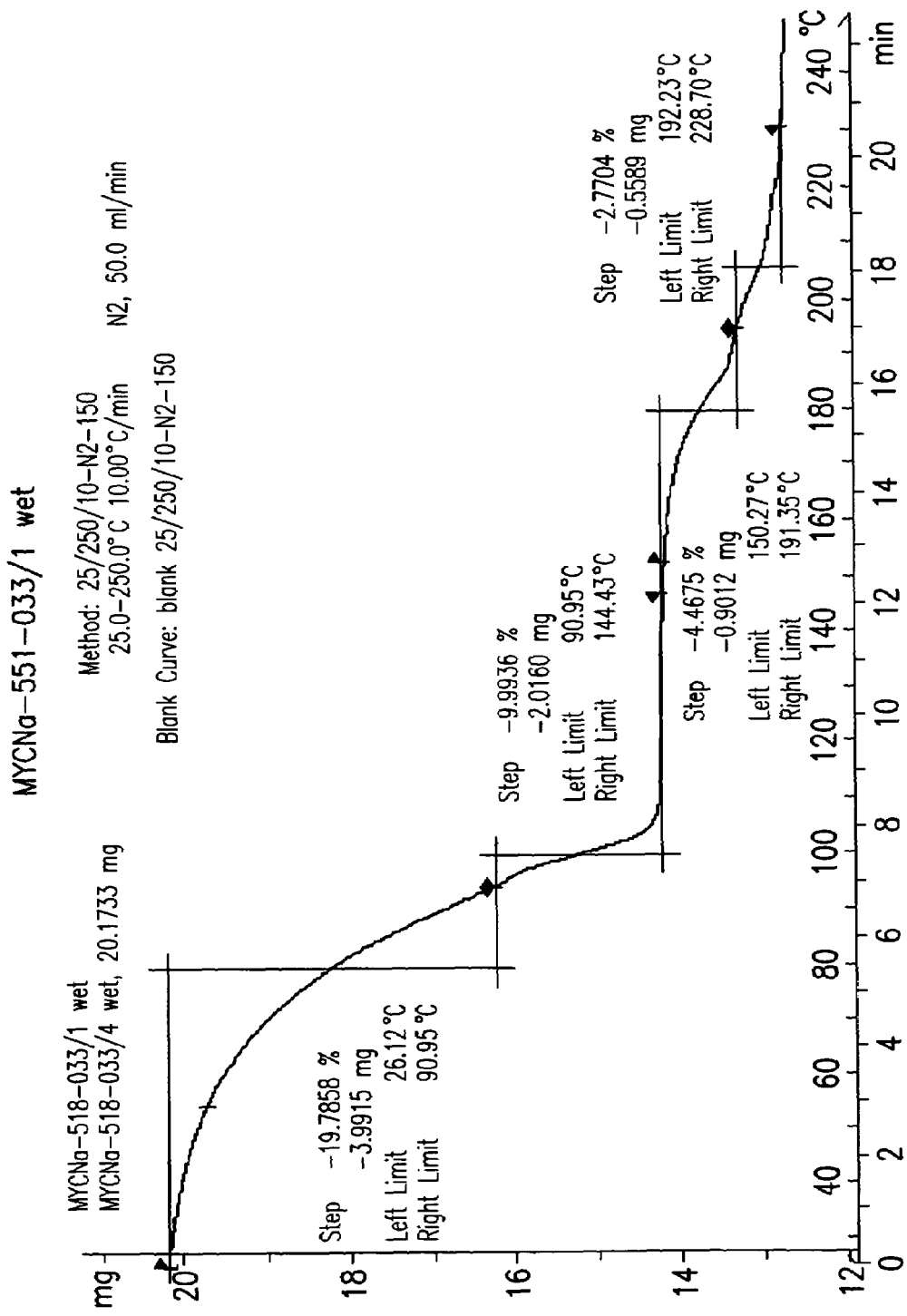
FIG. 74 is a characteristic TGA curve for monosodium mycophenolate form M26.
Figure 75:
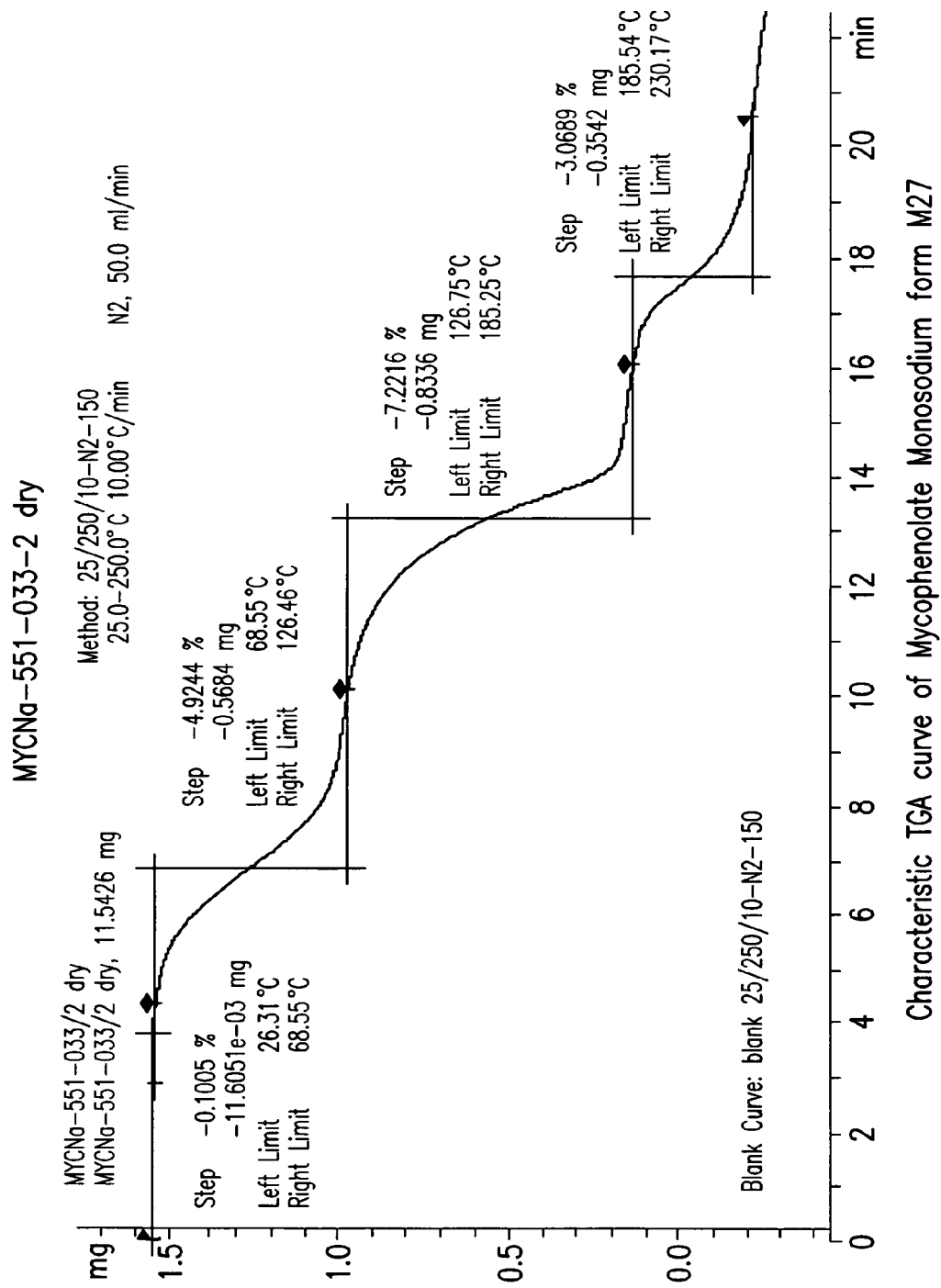
FIG. 75 is a characteristic TGA curve for monosodium mycophenolate form M27.
Figure 76:
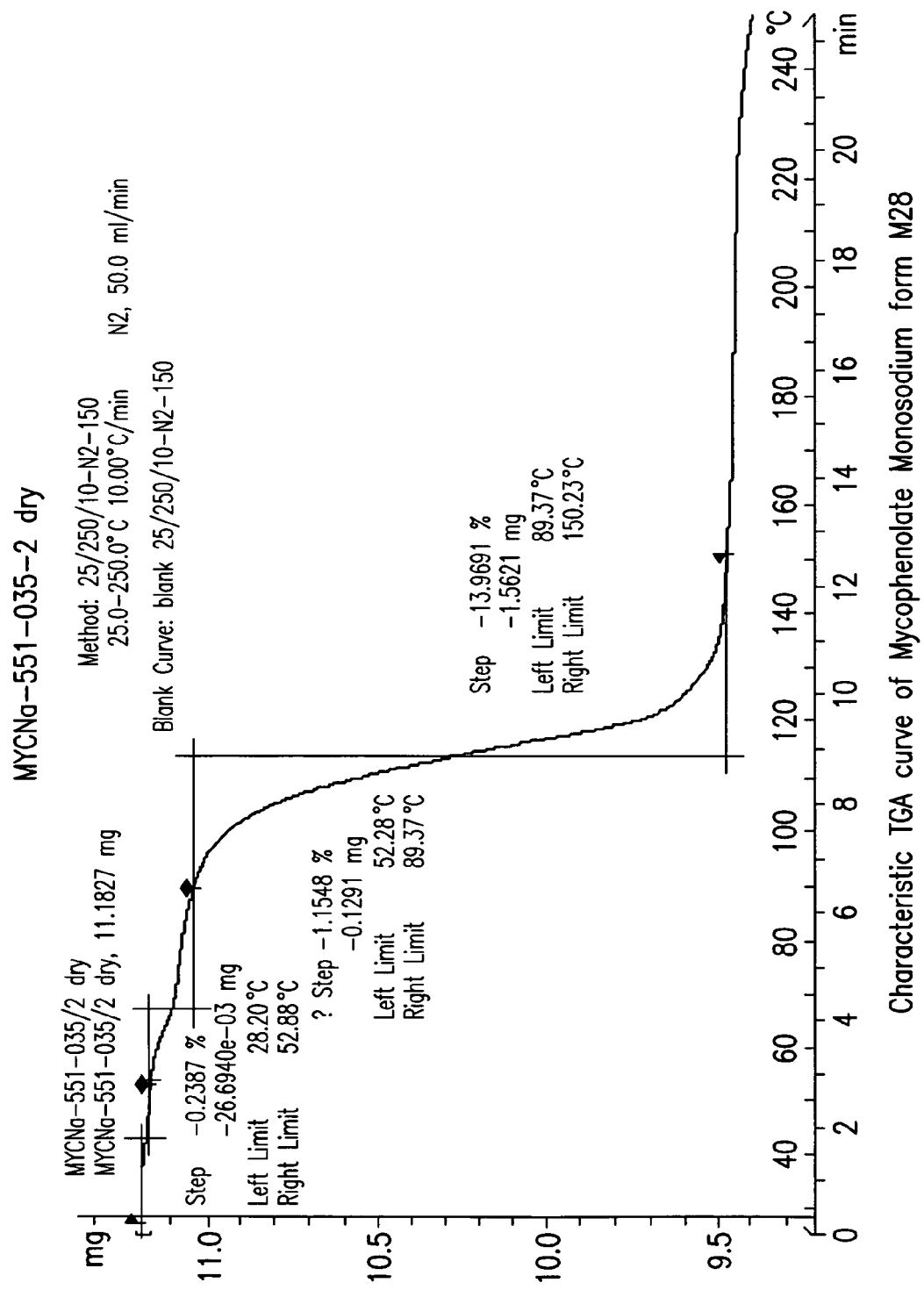
FIG. 76 is a characteristic TGA curve for monosodium mycophenolate form M28.

In another aspect, the present invention is amorphous mycophenolate sodium, denominated M12, characterized by FTIR peaks at 1735, 1560 and 1133 cm-1 (FIG. 16). Form M12 may be further characterized by FTIR peaks at 1192, 1164, 1074, 1031, 969 and 722 cm-1. The XRD of Form M12 is substantially halo-like which is characteristic of amorphous form. Form M12 may be substantially free of other crystalline forms of mycophenolate sodium. Form M12 is an amorphous form of monosodium mycophenolate. Its DSC curve indicates a small endothermic peak caused by evaporation of solvent, a wide exothermic peak due to recrystallization and the melting peak of the crystalline material at 189° C. (FIG. 53).

The invention provides a process for preparing mycophenolate sodium Form M12 by lyophilization (freeze drying) from water. Sodium mycophenolate is dissolved in water and the solution is lyophilized to obtain the amorphous form.

Form M15

One embodiment of the invention encompasses a crystalline mycophenolate sodium, denominated Form M15, characterized by data selected from at least one of a powder XRD pattern with peaks at 9.9, 13.1, 14.1, 16.1, 17.7, 18.5, 19.6, and 23.8±0.2 degrees 2-theta or an FTIR spectrum with peaks at 3434, 1727, 1650, 1609, 1561, 1326, 1277, 1194, 1139, 965, 858, 830, 799, 763, 723, 666 and 1132 $cm^{-1}$.

The invention also provides a process for preparing crystalline mycophenolate sodium M15 by precipitation from 1,4-dioxane. Precipitation may be carried out by preparing a mixture of sodium mycophenolate in 1,4-dioxane; heating the mixture; cooling the mixture; and recovering the crystalline form. Preferably, the ratio of 1,4-dioxane to sodium mycophenolate is less than about 100 ml/g, more preferably less than about 50 ml/g.

Form M16

One embodiment of the invention encompasses a crystalline mycophenolate sodium, denominated Form M16, characterized by data selected from at least one of a powder XRD pattern with peaks at 5.2, 5.5, 8.1, 11.0, 16.1, 16.6, 17.3, and 22.0±0.2 degrees 2-theta or an FTIR spectrum with peaks at 3436, 1721, 1685, 1654, 1614, 1552, 1320, 1275, 1253, 1219, 1133, 1111, 1080, 1038, 975, 878, 807, 778, and 722 $cm^{-1}$.

The invention also provides a process for preparing crystalline mycophenolate sodium M16 by precipitation from 4-methyl-2-pentanone. Precipitation may be carried out by preparing a mixture of sodium mycophenolate in 4-methyl-2-pentanone; heating the mixture; cooling the mixture; and recovering the crystalline form.

Form M17

One embodiment of the invention encompasses a crystalline mycophenolate sodium, denominated Form M17, characterized by data selected from at least one of a powder XRD pattern with peaks at 5.5, 7.7, 8.1, 9.8, 10.7, 11.0, 16.5, 22.0, and 26.0±0.2 degrees 2-theta or an FTIR spectrum with peaks at 3470, 1722, 1650, 1608, 1560, 1254, 1083, 1040, 974, and 772 $cm^{-1}$.

The invention also provides a process for preparing crystalline mycophenolate sodium M17 by precipitation from dimethylcarbonate. Precipitation may be carried out by preparing a mixture of sodium mycophenolate in dimethylcarbonate; heating the mixture; cooling the mixture; and recovering the crystalline form.

Form M18

One embodiment of the invention encompasses a crystalline mycophenolate sodium, denominated Form M18, characterized by data selected from at least one of a powder XRD pattern with peaks at 5.6, 8.1, 9.9, 10.8, 13.7, 16.6, 19.1, and 22.1±0.2 degrees 2-theta or an FTIR spectrum with peaks at 3449, 1723, 1686, 1614, 1552, 1320, 1253, 1134, 1110, 1078, 1036, 974, 879, 856, 831, 808, 764, and 722 $cm^{-1}$.

The invention also provides a process for preparing crystalline mycophenolate sodium M18 by precipitation from 2-methyl-2-propanol. Precipitation may be carried out by preparing a mixture of sodium mycophenolate in 2-methyl-2-propanol; heating the mixture; cooling the mixture; and recovering the crystalline form.

Form M19

One embodiment of the invention encompasses a crystalline mycophenolate sodium, denominated Form M19, characterized by data selected from at least one of a powder XRD pattern with peaks at 7.6, 8.3, 10.7, 11.7, 15.9, 18.2, 21.0, and 21.6±0.2 degrees 2-theta or an FTIR spectrum with peaks at 3422, 1710, 1569, 1264, 1190, 1133, 1111, 1074, 1032, 971, 943, 918, 864, 829, 796, and 722 $cm^{-1}$.

The invention also provides a process for preparing crystalline mycophenolate sodium M19 by precipitation from methanol, with use of carbon tetrachloride as an antisolvent. As exemplified, carbon tetrachloride is combined with a solution of sodium mycophenolate in methanol, followed by cooling to optimize crystallization. The crystals are then recovered by conventional techniques.

Form M20

One embodiment of the invention encompasses a crystalline mycophenolate sodium, denominated Form M20, characterized by data selected from at least one of a powder XRD pattern with peaks at 5.1, 5.5, 6.7, 10.0, 10.9, 13.1, 14.6, 17.3, and 24.8±0.2 degrees 2-theta or an FTIR spectrum with peaks at 1731, 1694, 1618, 1588, 1568, 1405, 1262, 1204, 1164, 1136, 1111, 1081, 1033, 974, 948, 922, 870, 790, 764, and 722 $cm^{-1}$.

The invention also provides a process for preparing crystalline mycophenolate sodium M20 by precipitation from N,N-dimethyl-acetamide, with use of acetonitrile as an antisolvent. As exemplified, acetonitrile is combined with a solution of sodium mycophenolate in N,N-dimethyl-acetamide, followed by cooling to optimize crystallization. The crystals are then recovered by conventional techniques.

Form M21

One embodiment of the invention encompasses a crystalline mycophenolate sodium, denominated Form M21, characterized by data selected from at least one of a powder XRD pattern with peaks at 5.4, 6.2, 7.9, 8.7, 8.9, 16.8, 20.0, and 25.2±0.2 degrees 2-theta or an FTIR spectrum with peaks at 3488, 1720, 1615, 1550, 1403, 1323, 1288, 1260, 1208, 1137, 1114, 1084, 979, 927, 869, 812, and 722 $cm^{-1}$.

The invention also provides a process for preparing crystalline mycophenolate sodium M21 by crystallization from a mixture of water and 1,4-dioxane. As exemplified, the crystallization is carried out by preparing a mixture of sodium mycophenolate in a first portion of 1,4-dioxane and a first portion of water; combining a second portion of water with the mixture to dissolve the sodium mycophenolate; combining a second portion of 1,4-dioxane with the mixture to precipitating the crystalline form; and recovering the crystalline form. The solution may be cooled to optimize precipitation. The process may be modified so that all of the water is added on one portion.

Form M22

One embodiment of the invention encompasses a crystalline mycophenolate sodium, denominated Form M22, characterized by data selected from at least one of a powder XRD pattern with peaks at 3.8, 4.7, 5.3, 6.6, 8.1, 9.8, 10.6, 11.1, 15.5, and 23.3±0.2 degrees 2-theta or an FTIR spectrum with peaks at 3432, 1748, 1720, 1618, 1564, 1414, 1268, 1192, 1134, 1107, 1077, 1031, 971, 949, 875, 824, 794, and 723 $cm^{-1}$.

The invention also provides a process for preparing crystalline mycophenolate sodium M22 by crystallization from dichloromethane. As exemplified, the process includes preparing a solution of mycophenolic acid in a first portion of dichloromethane; combining a base and a source of sodium with the solution to precipitate the crystalline form; and recovering the crystalline form. A second portion of dichloromethane may be added to dilute the reaction mixture after addition of the base.

Form M26

One embodiment of the invention encompasses a crystalline mycophenolate sodium, denominated Form M26, characterized by data selected from at least one of a powder XRD pattern with peaks at 5.8, 9.2, 9.5, 10.0, 13.4, 13.7, 15.8, 17.6, 23.6, and 24.1±0.2 degrees 2-theta or an FTIR spectrum with peaks at 1741, 1612, 1584, 1316, 1272, 1256, 1219, 1195, 1134, 1122, 1104, 1083, 1032, 966, 874, 794, 722, and 679 $cm^{-1}$.

The invention also provides a process for preparing crystalline mycophenolate sodium M26 by crystallization from 1,4 dioxane. As exemplified, this process includes preparing a solution of mycophenolic acid in 1,4-dioxane; combining a base and a source of sodium with the solution to precipitate the crystalline form; and recovering the crystalline form.

Form M27

One embodiment of the invention encompasses a crystalline mycophenolate sodium, denominated Form M27, characterized by data selected from at least one of a powder XRD pattern with peaks at 6.2, 9.4, 12.6, 13.1, 13.7, 14.0, 15.9, 17.5, and 24.1±0.2 degrees 2-theta or an FTIR spectrum with peaks at 1727, 1593, 1327, 1275, 1221, 1195, 1139, 1114, 1082, 1031, 965, 874, 798, 763, 723, and 666 cm$^{-1}$.

The invention also provides a process for preparing crystalline mycophenolate sodium M27 by crystallization from 1,4 dioxane followed by drying. Drying of wet Form 26 results in Form M27. Drying may be carried out under ambient conditions.

Form M28

One embodiment of the invention encompasses a crystalline mycophenolate sodium, denominated Form M28, characterized by data selected from at least one of a powder XRD pattern with peaks at 7.7, 8.5, 9.9, 12.3, 16.0, 21.4, 23.2, and 26.0±0.2 degrees 2-theta or an FTIR spectrum with peaks at 1730, 1696, 1612, 1588, 1570, 1403, 1301, 1263, 1194, 1165, 1135, 1109, 1079, 1033, 973, 948, 869, 832, 791, 763, and 723 cm$^{-1}$.

The invention also provides a process for preparing crystalline mycophenolate sodium M28 by precipitation from carbon-tetrachloride. As exemplified, this process includes preparing a solution of mycophenolic acid in carbon-tetrachloride; combining a base and a source of sodium with the solution to precipitate the crystalline form; and recovering the crystalline form. Preferably the base is sodium methoxide.

Form D1

Figure 17:
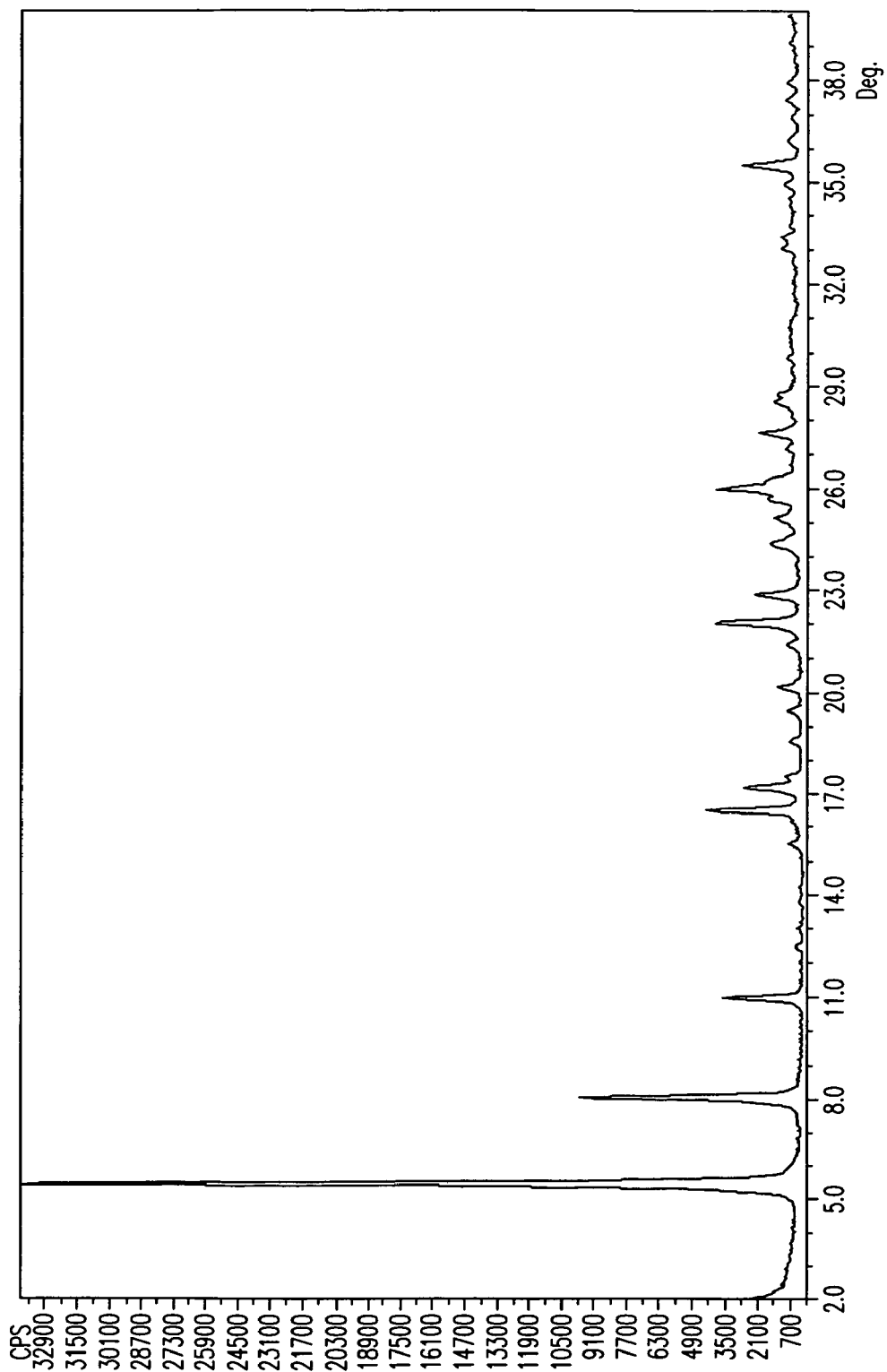
FIG. 17 is a characteristic X-ray powder diffraction pattern for disodium mycophenolate form D1.
Figure 18:
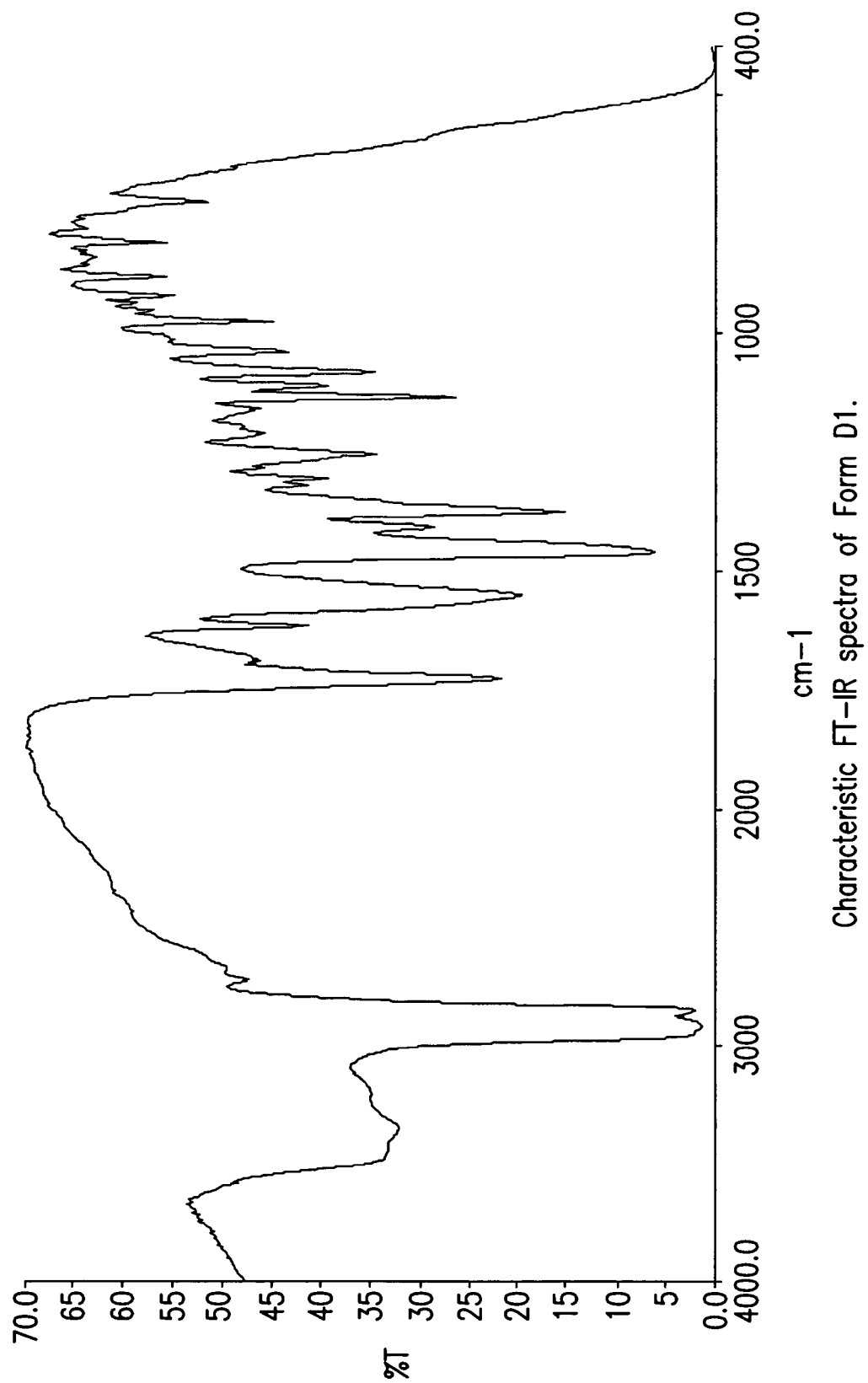
FIG. 18 is a characteristic FT-IR spectrum for disodium mycophenolate form D1.

In another aspect, the present invention is a crystalline disodium mycophenolate, denominated Form D1, characterized by a powder XRD pattern with peaks at 5.5, 8.1, 11.0, 16.5, and 26.0±0.2 degrees 2 theta (FIG. 17) and FTIR peaks at 3344 and 1552 cm$^{-1}$ (FIG. 18). Form D1 may be further characterized by an XRD peak at 22.1±0.2 degrees 2 theta. Form D1 may be even further characterized by FTIR peaks at 1723, 1614, 1254 and 1133 cm$^{-1}$. Form D1 may be substantially free of other crystalline forms of mycophenolate sodium.

The invention provides a process for preparing mycophenolate disodium Form D1. First, sodium carbonate is added to solution of mycophenolate acid in methanol. Second, the solution is concentrated, preferably by rotary evaporation. The solution is preferably concentrated to about ⅓ volume to about half volume. Third, the crystalline form is precipitated from the mixture, preferably by cooling the solution to about −10° C. to −20° C. Finally, the crystalline form is recovered.

Form D2

Figure 19:
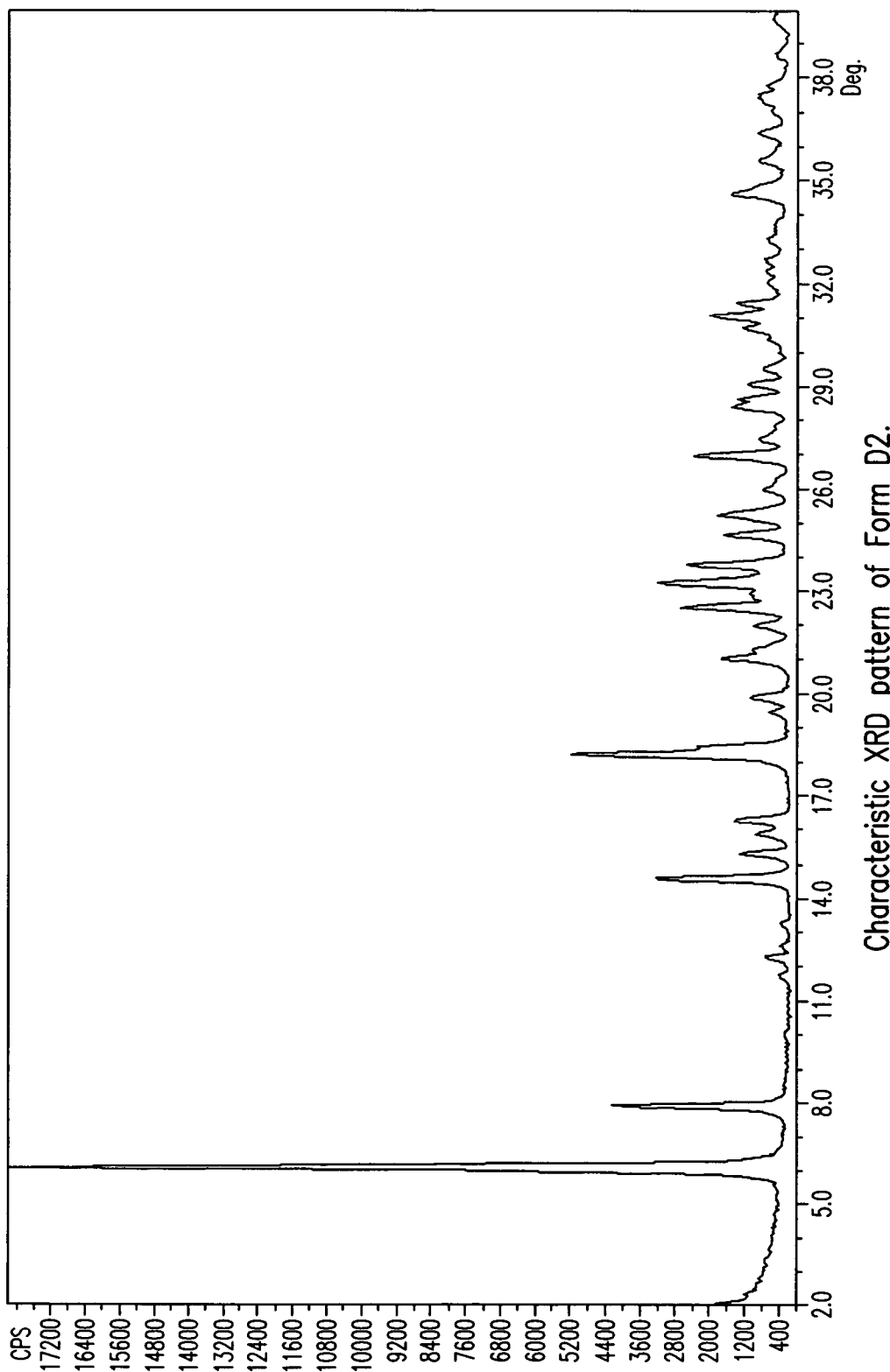
FIG. 19 is a characteristic X-ray powder diffraction pattern for disodium mycophenolate form D2.
Figure 20:
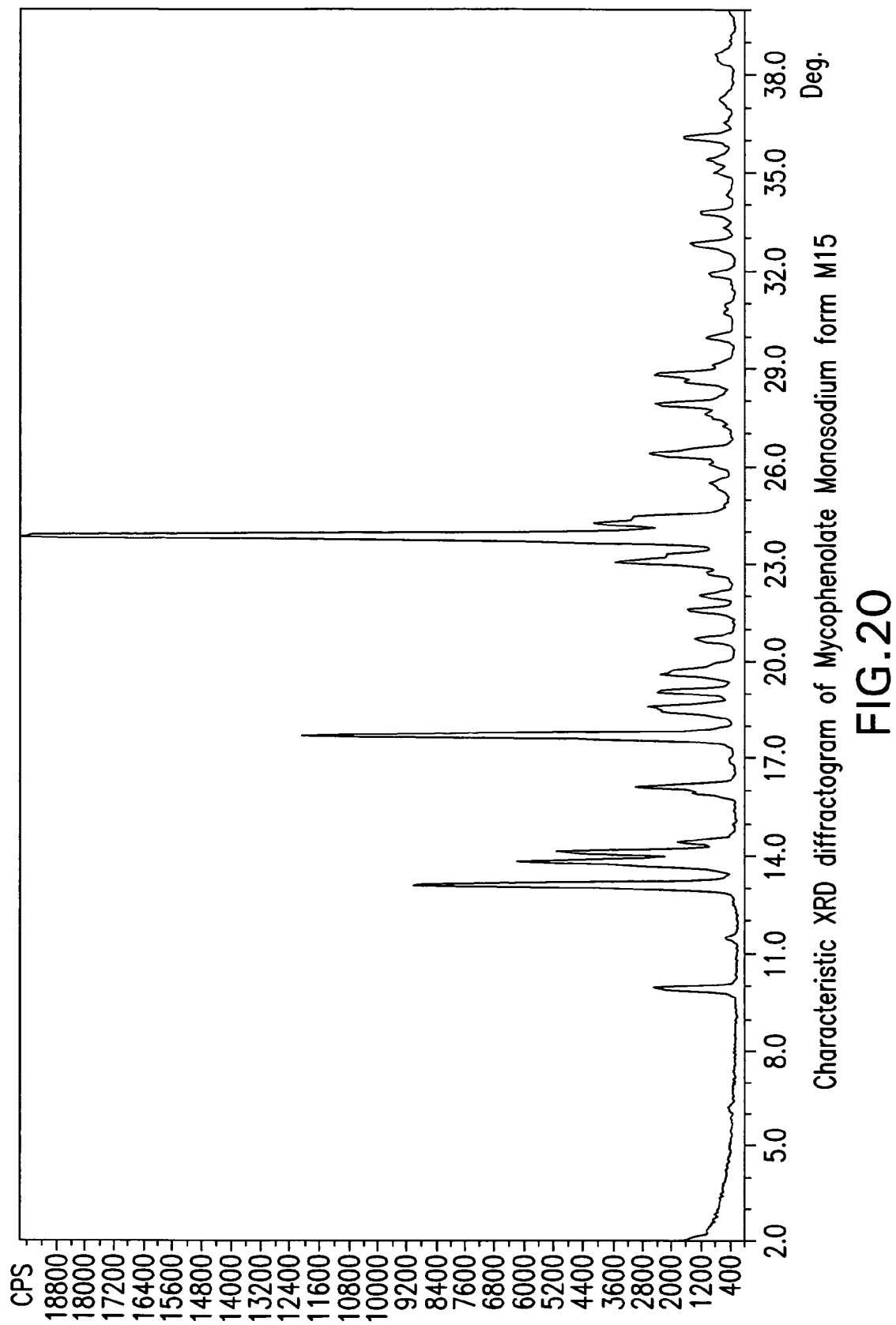
FIG. 20 is a characteristic X-ray powder diffraction pattern for monosodium mycophenolate form M15.
Figure 21:
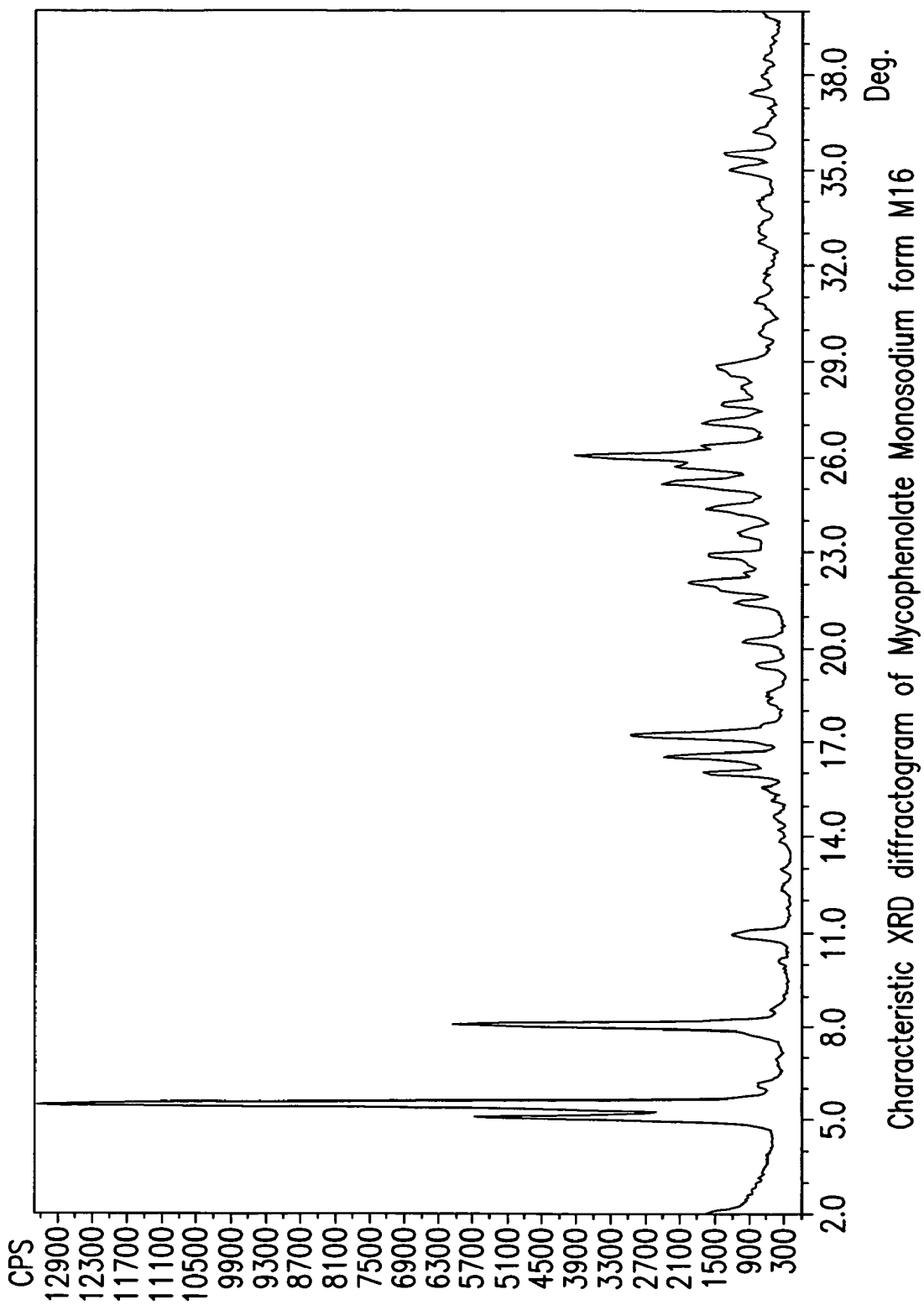
FIG. 21 is a characteristic X-ray powder diffraction pattern for monosodium mycophenolate form M16.
Figure 22:
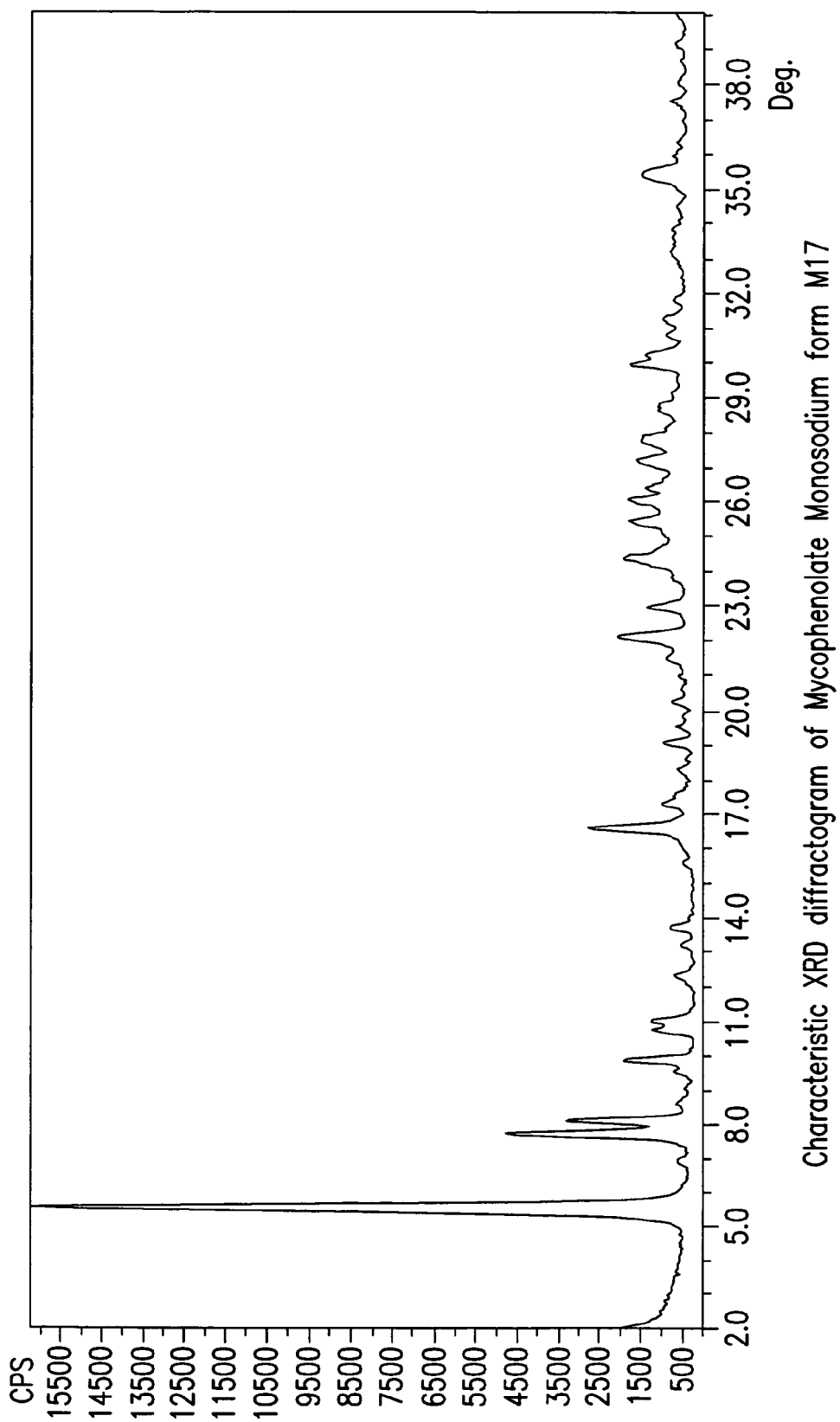
FIG. 22 is a characteristic X-ray Powder Diffraction pattern for monosodium mycophenolate form M17.
Figure 23:
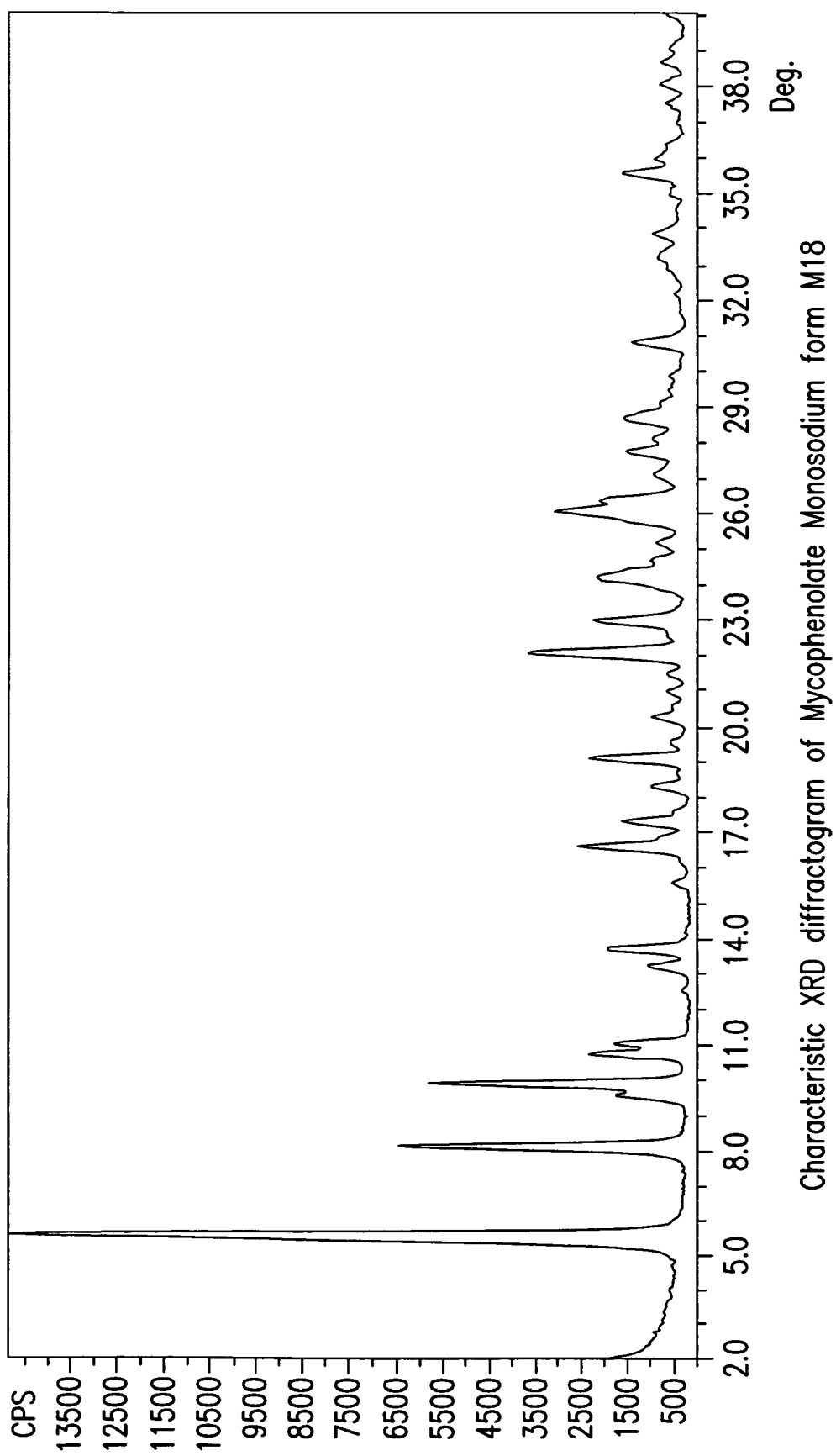
FIG. 23 is a characteristic X-ray powder diffraction pattern for monosodium mycophenolate form M18.
Figure 24:
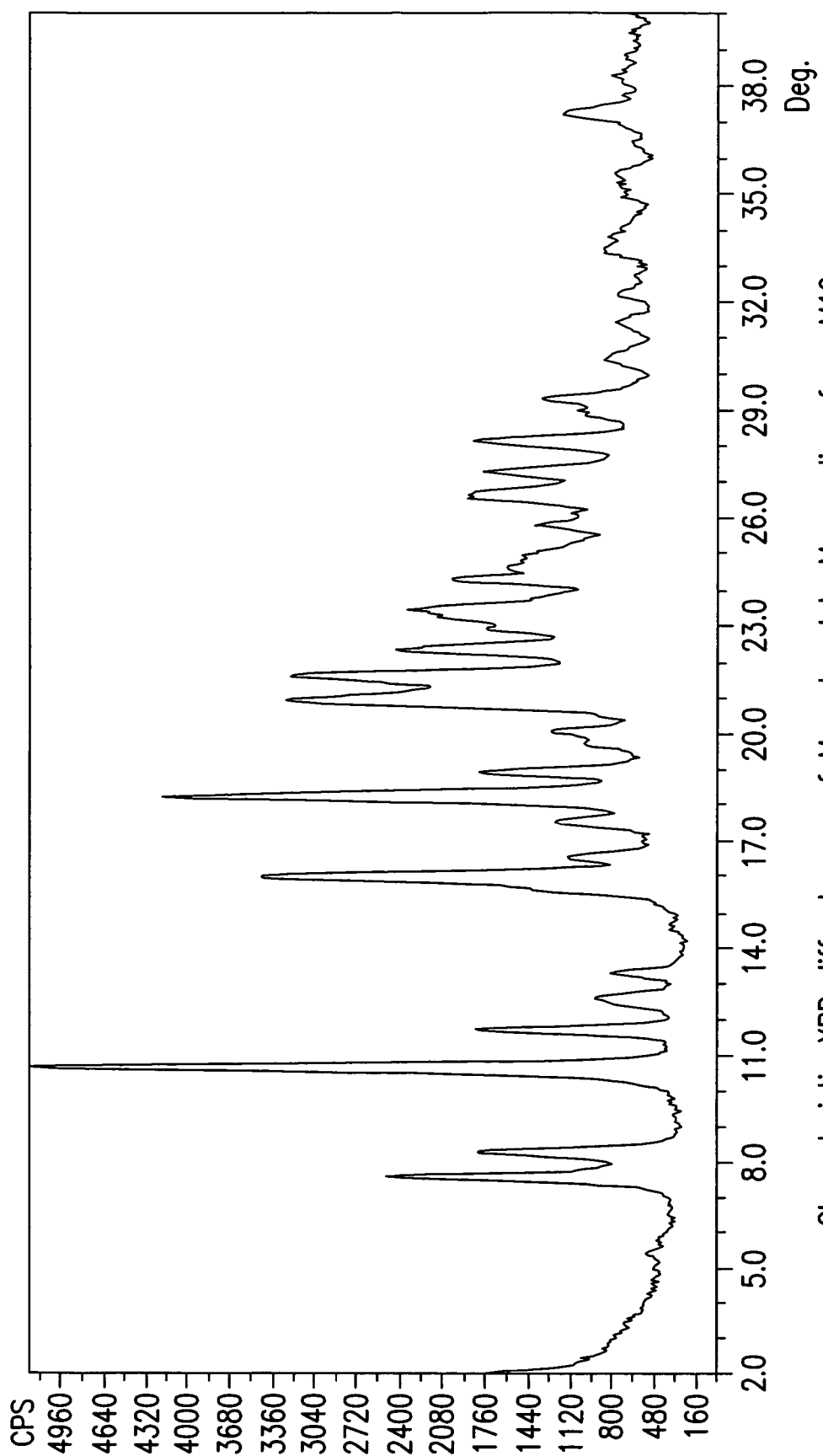
FIG. 24 is a characteristic X-ray powder diffraction pattern for monosodium mycophenolate form M19.
Figure 25:
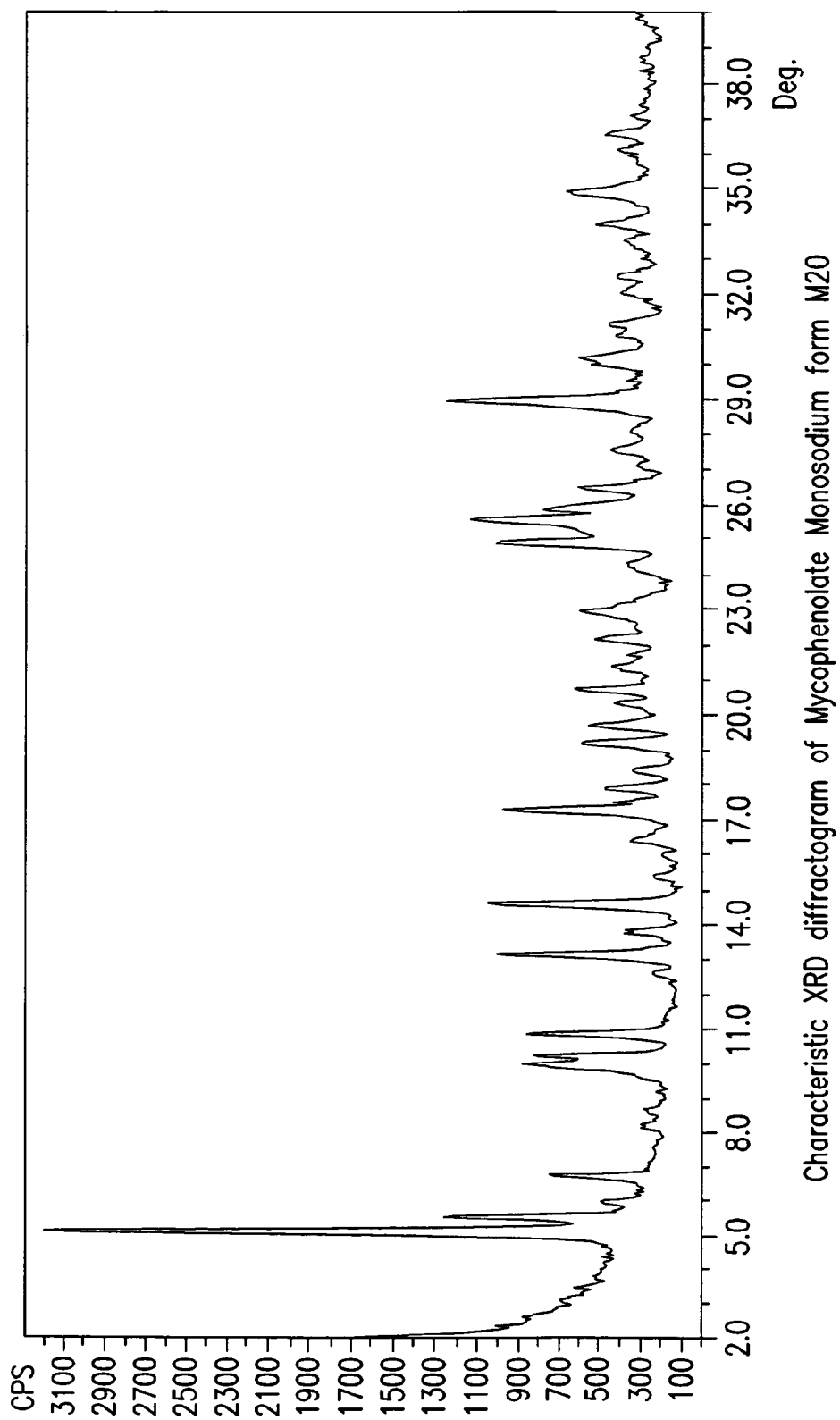
FIG. 25 is a characteristic X-ray powder diffraction pattern for monosodium mycophenolate form M20.
Figure 26:
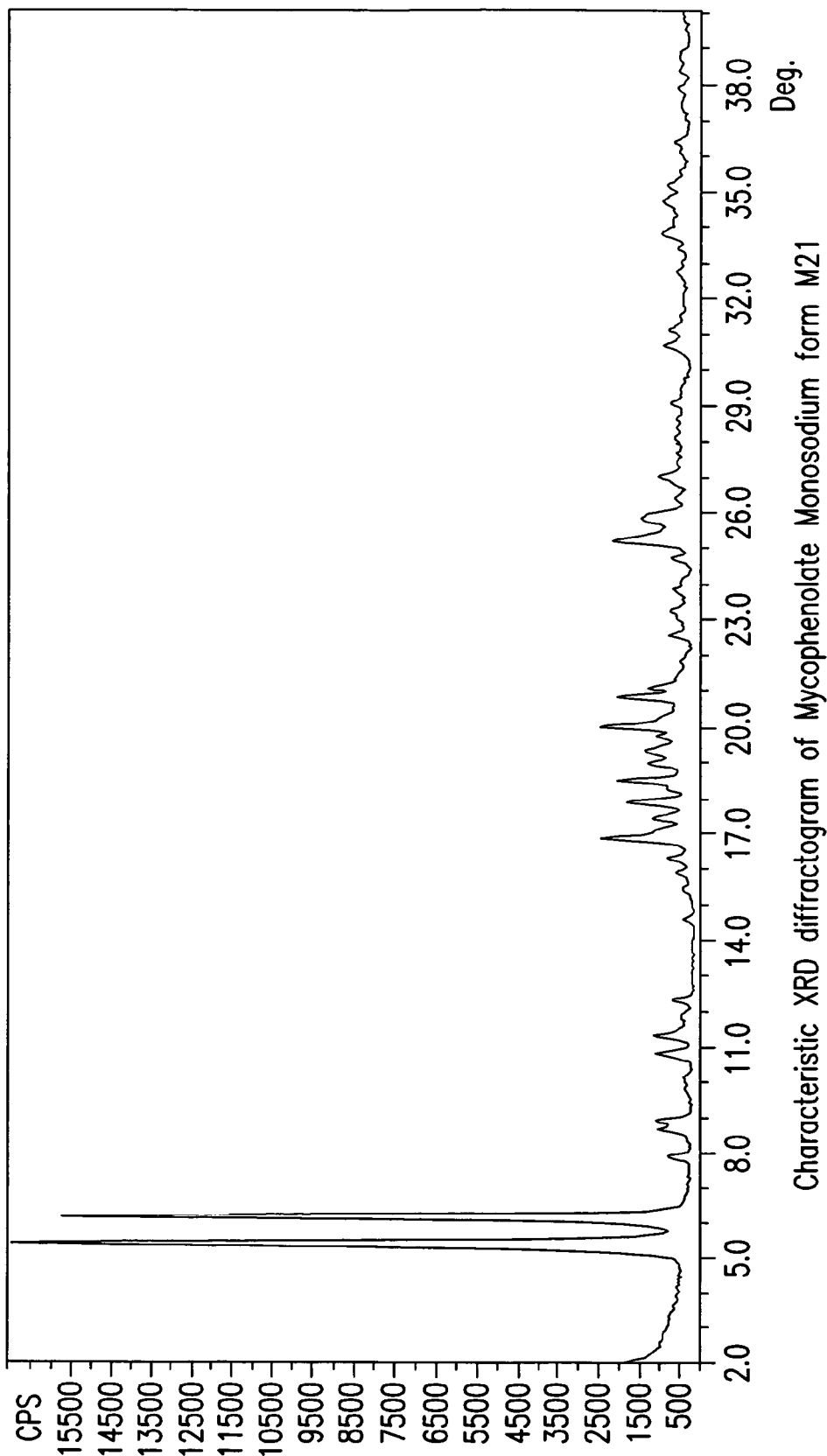
FIG. 26 is a characteristic X-ray powder diffraction pattern for monosodium mycophenolate form M21.
Figure 27:
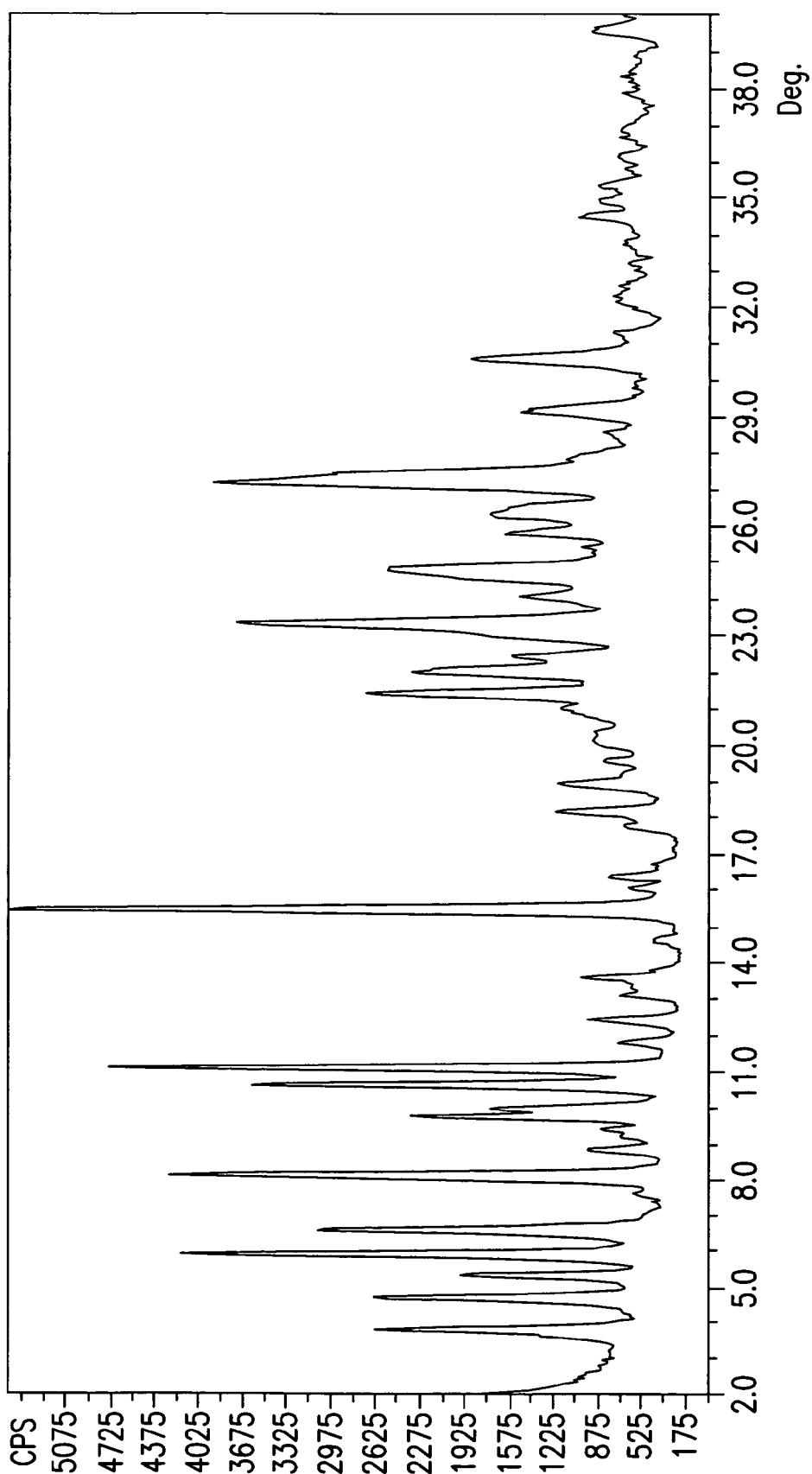
FIG. 27 is a characteristic X-ray powder diffraction pattern for monosodium mycophenolate form M22.
Figure 28:
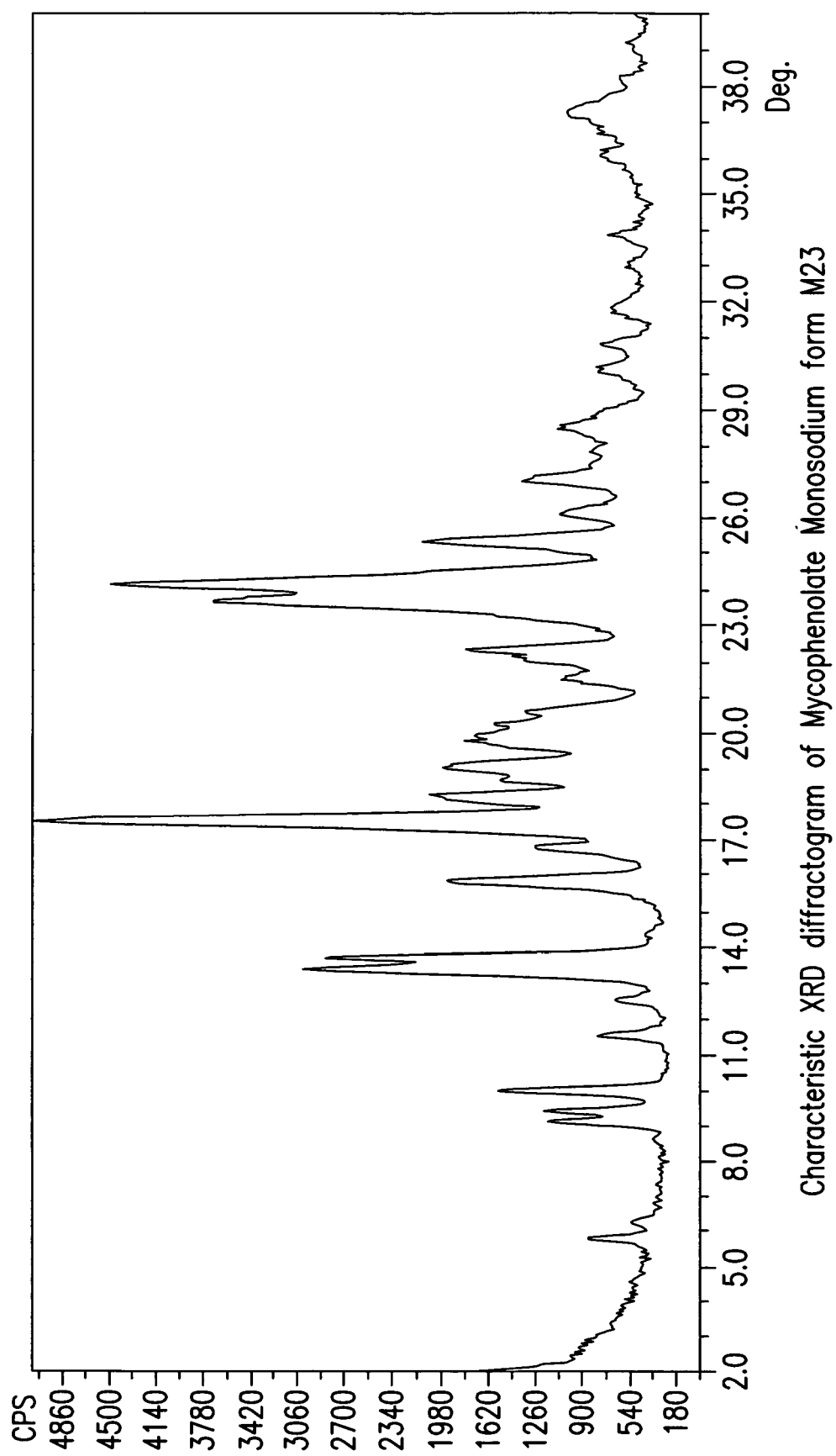
FIG. 28 is a characteristic X-ray powder diffraction pattern for monosodium mycophenolate form M26.
Figure 29:
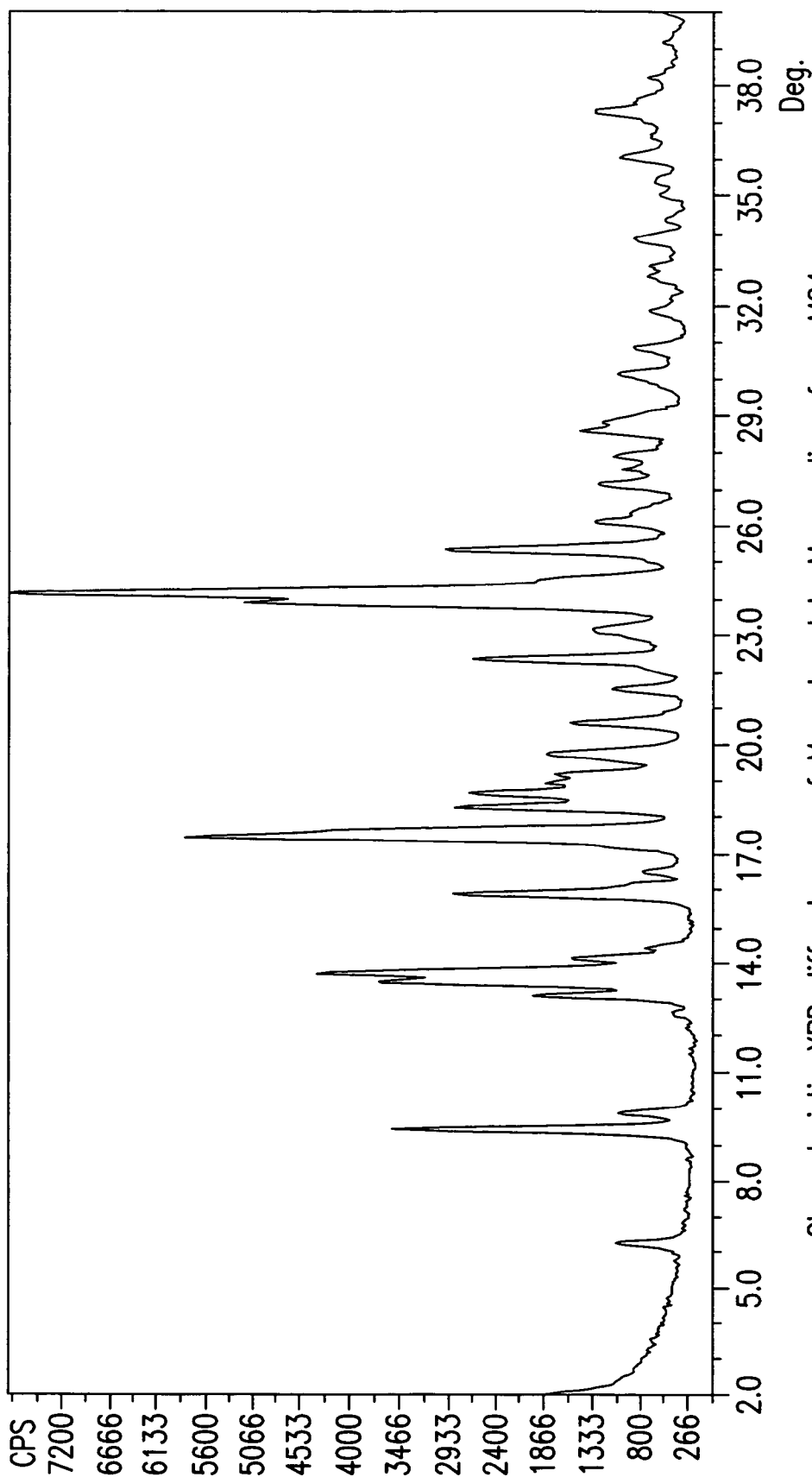
FIG. 29 is a characteristic X-ray powder diffraction pattern for monosodium mycophenolate form M27.
Figure 30:
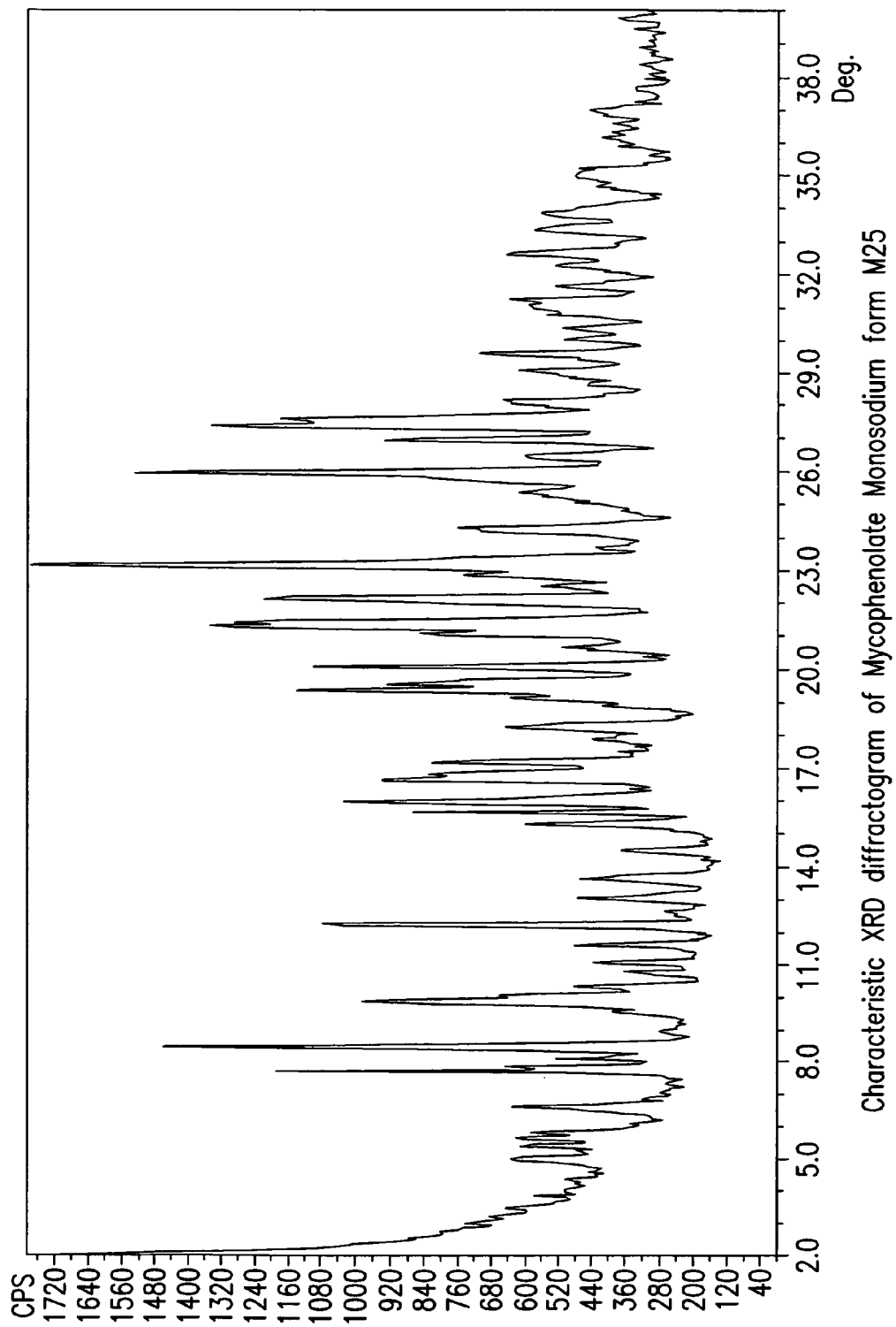
FIG. 30 is a characteristic X-ray powder diffraction pattern for monosodium mycophenolate form M28.
Figure 31:
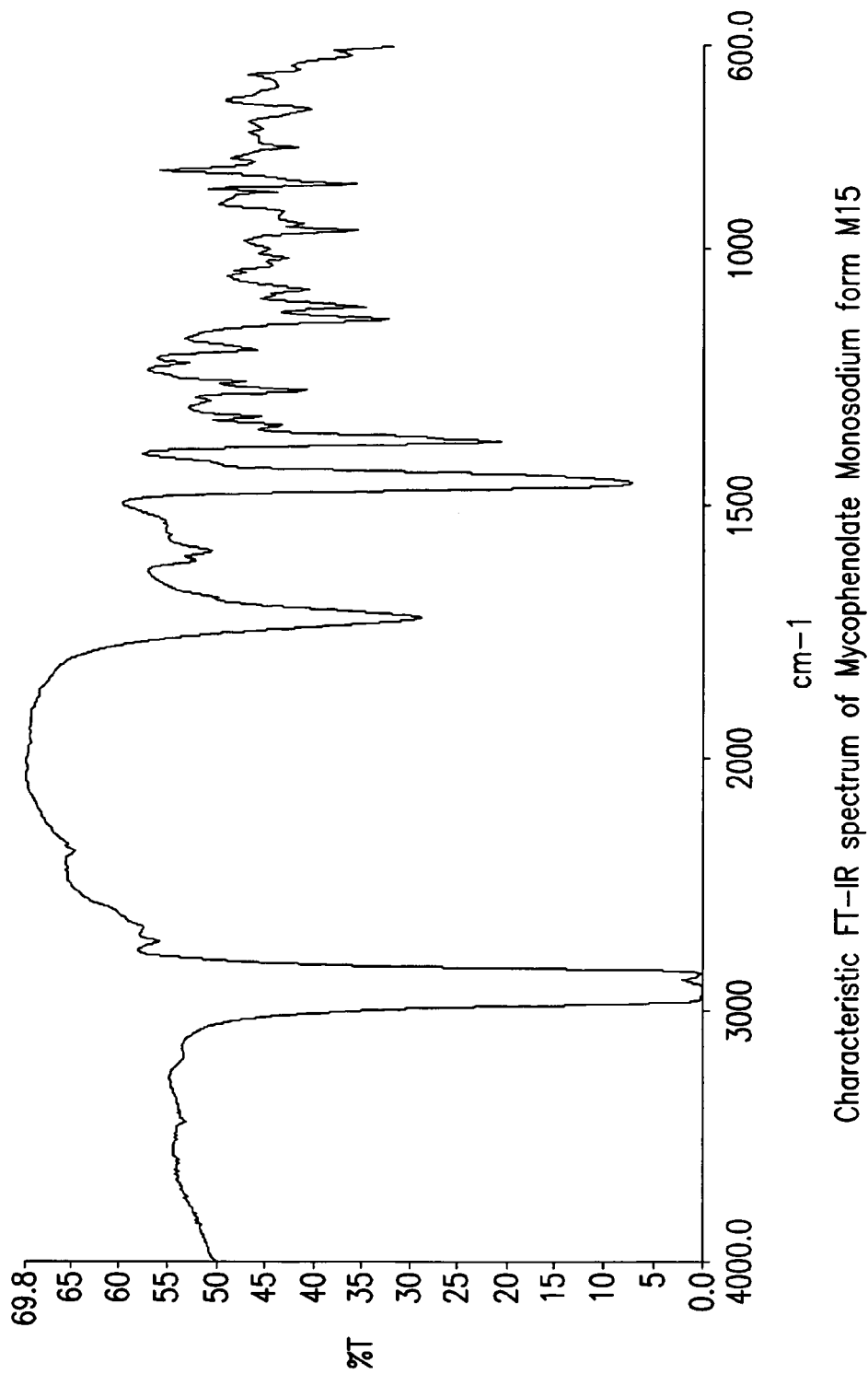
FIG. 31 is a characteristic FTIR spectrum for monosodium mycophenolate form M15.
Figure 32:
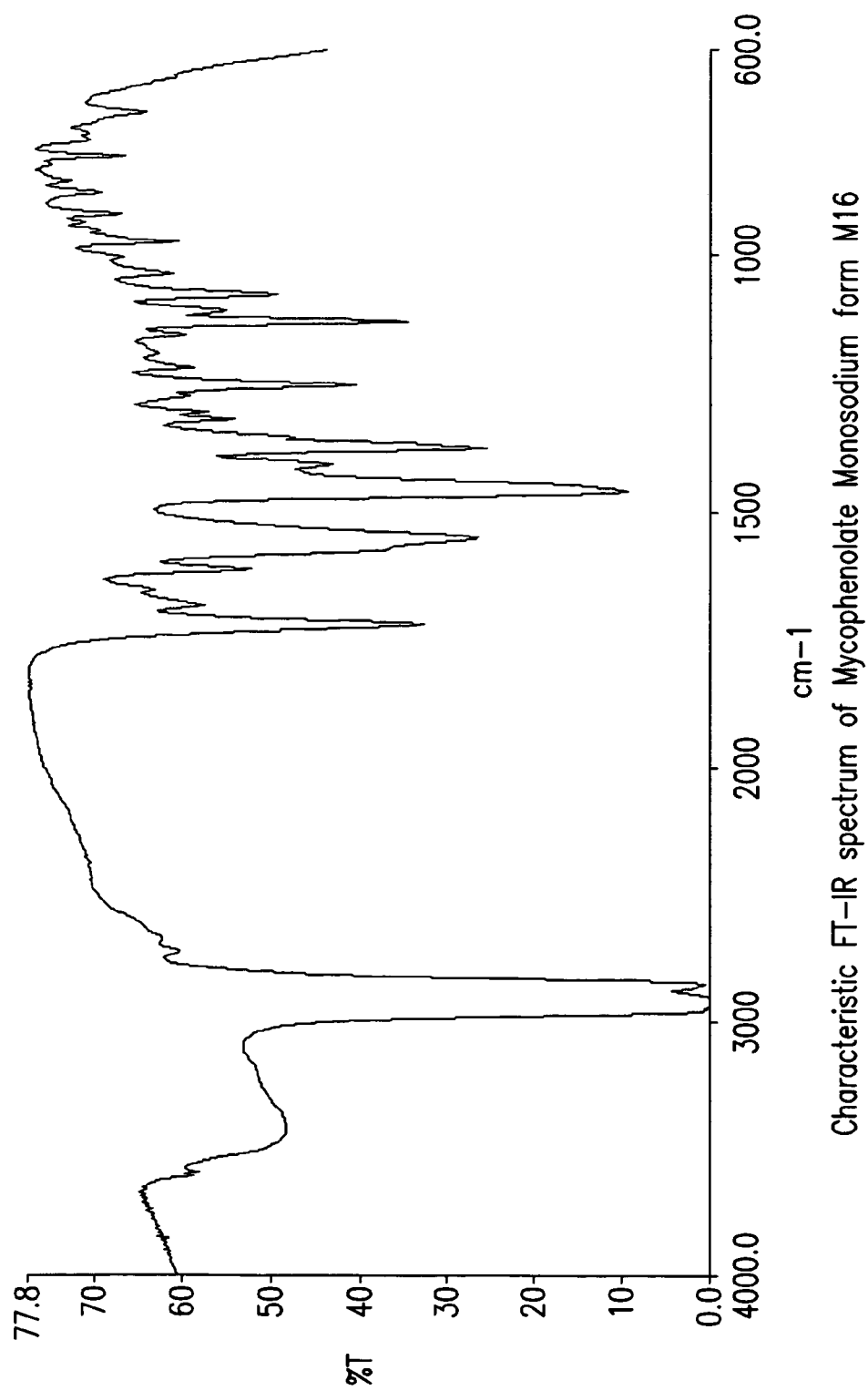
FIG. 32 is a characteristic FTIR spectrum for monosodium mycophenolate form M16.
Figure 33:
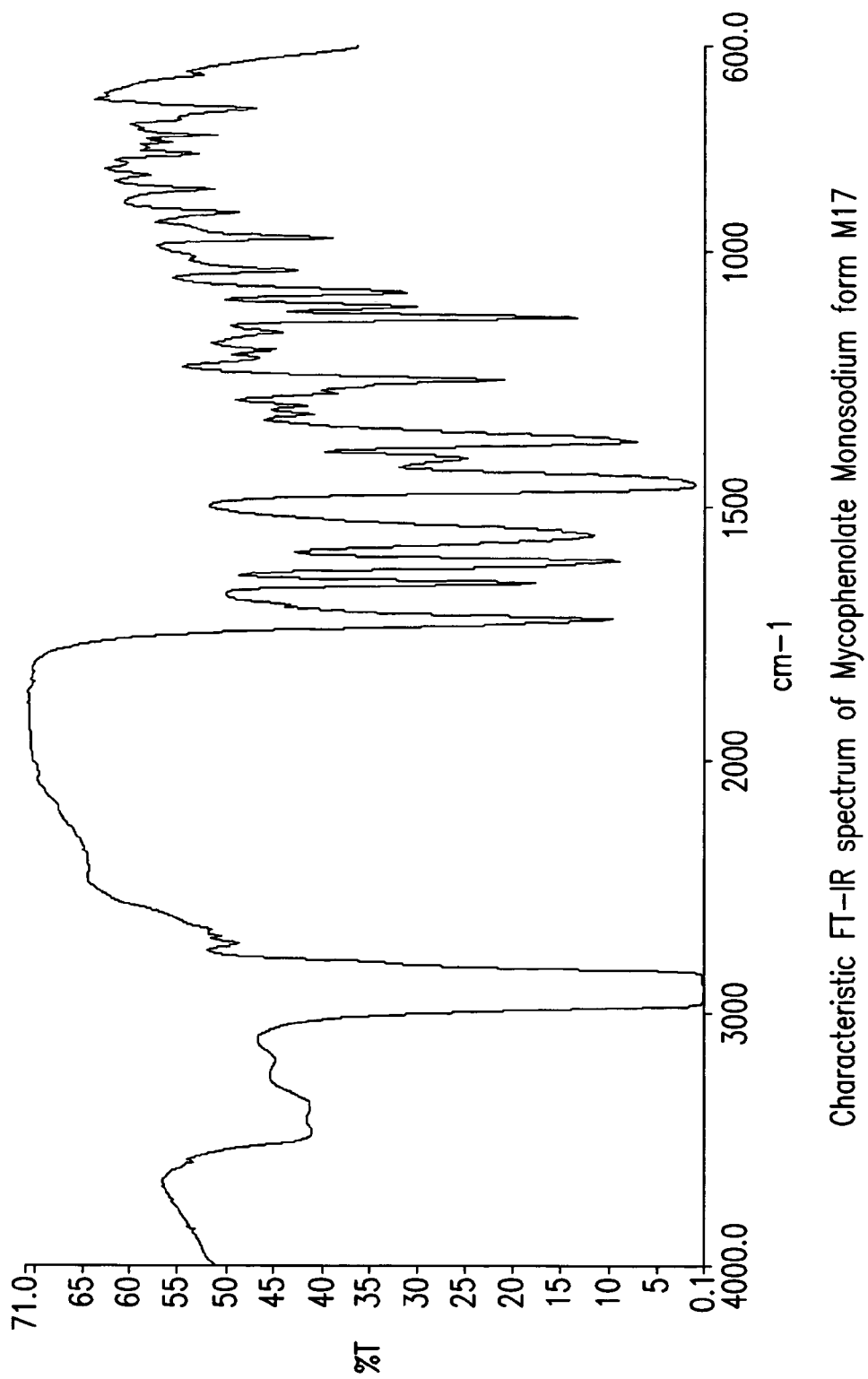
FIG. 33 is a characteristic FTIR spectrum for monosodium mycophenolate form M17.
Figure 34:
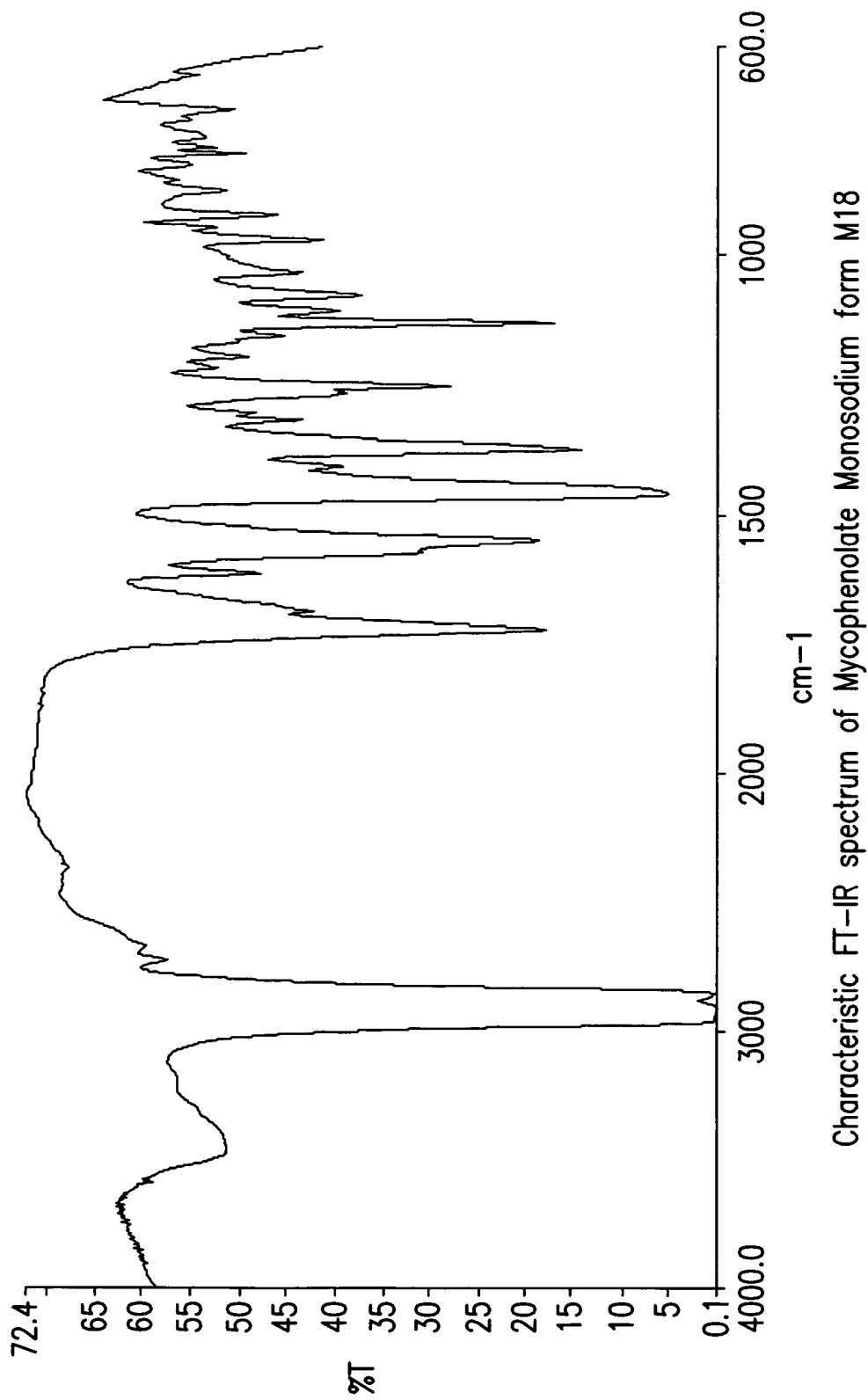
FIG. 34 is a characteristic FTIR spectrum for monosodium mycophenolate form M18.
Figure 35:
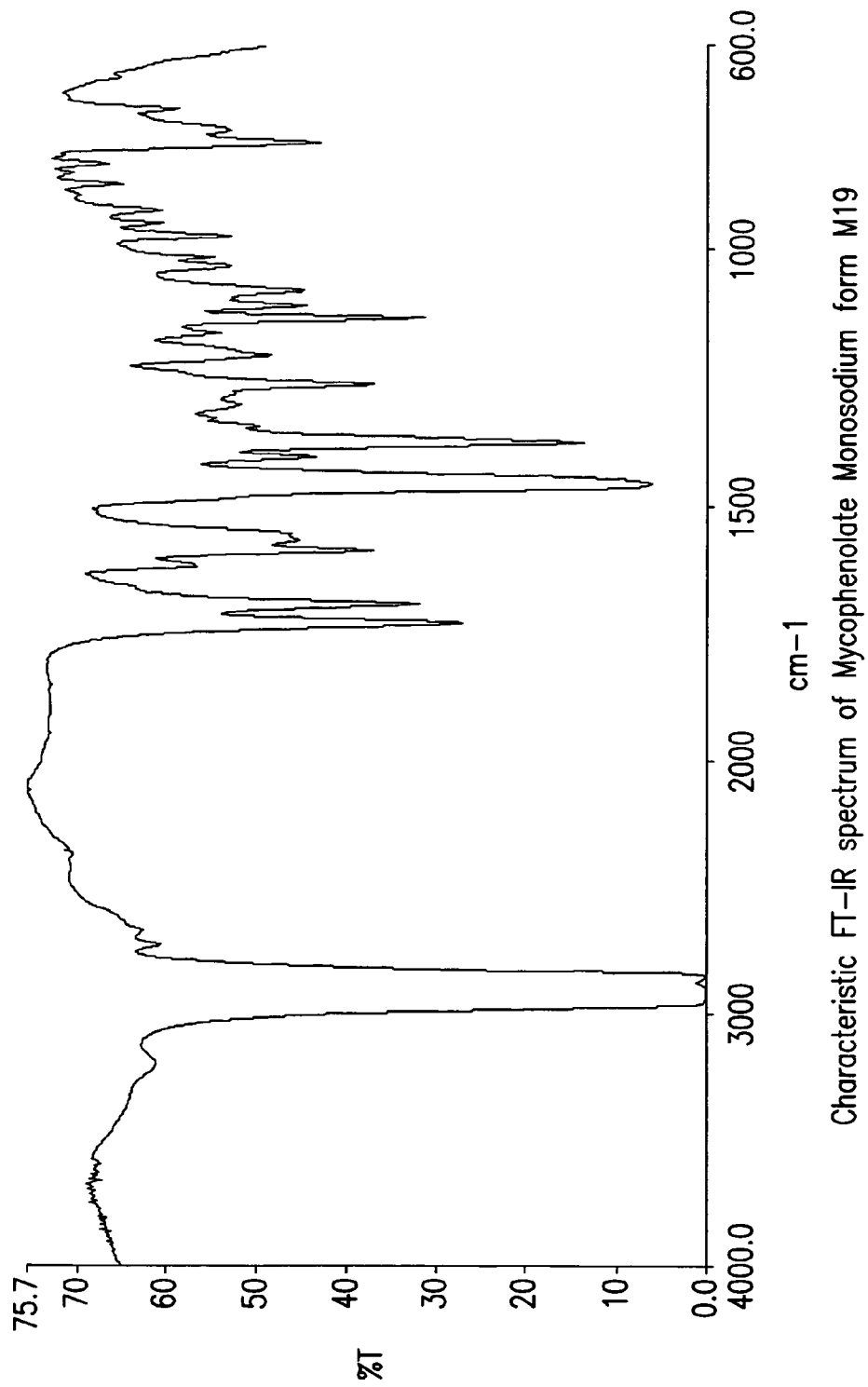
FIG. 35 is a characteristic FTIR spectrum for monosodium mycophenolate form M19.
Figure 36:
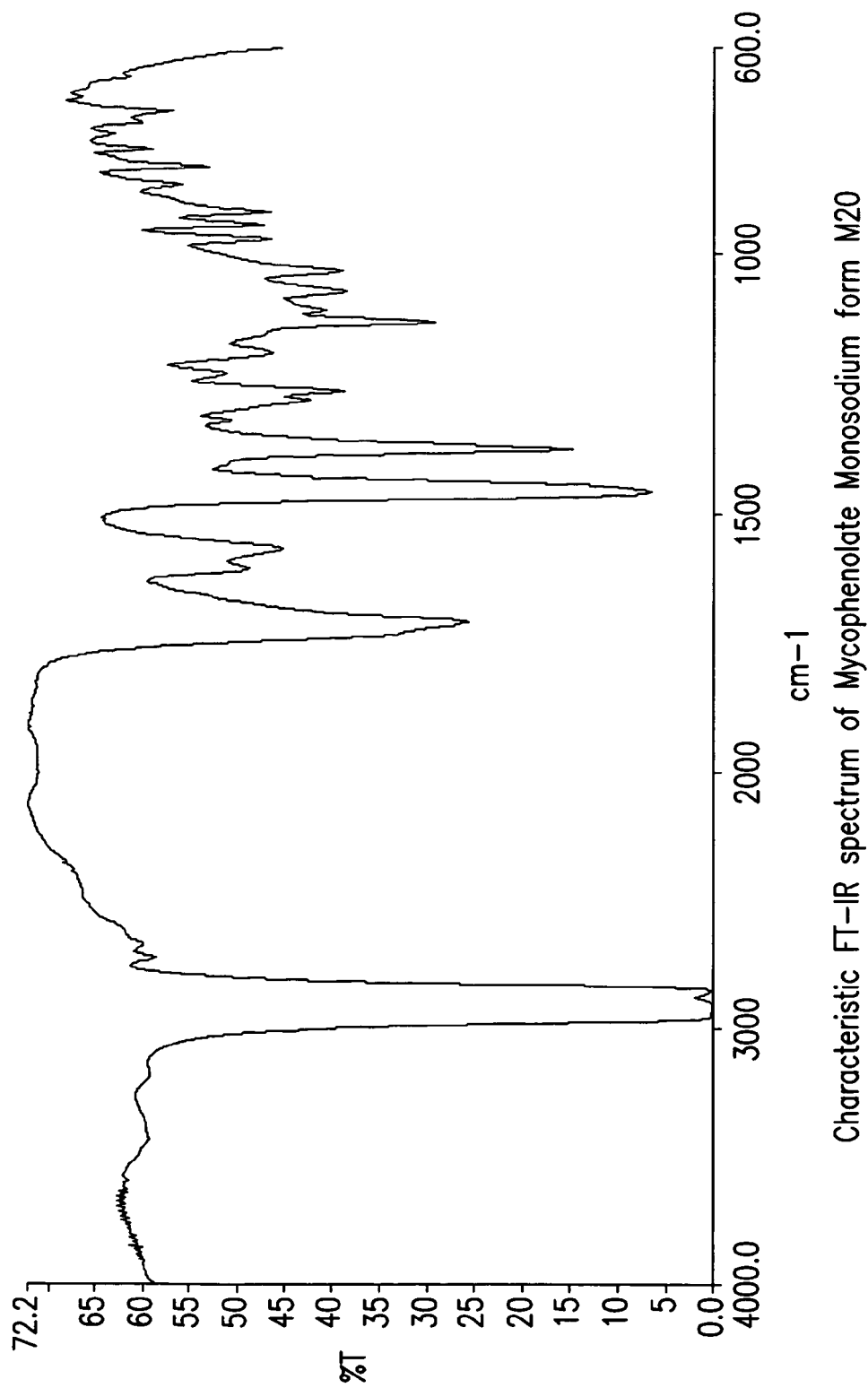
FIG. 36 is a characteristic FTIR spectrum for monosodium mycophenolate form M20.
Figure 37:
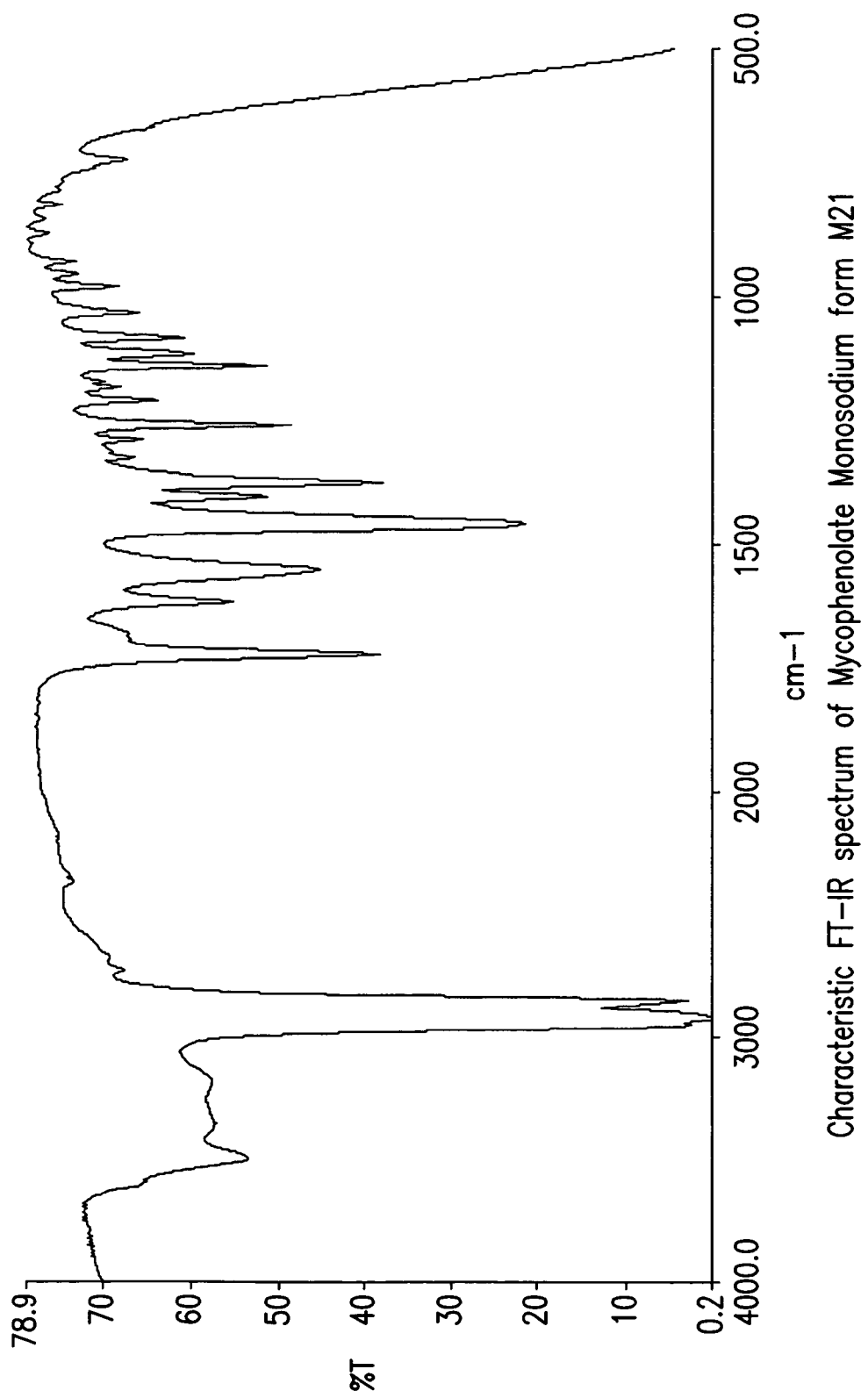
FIG. 37 is a characteristic FTIR spectrum for monosodium mycophenolate form M21.
Figure 38:
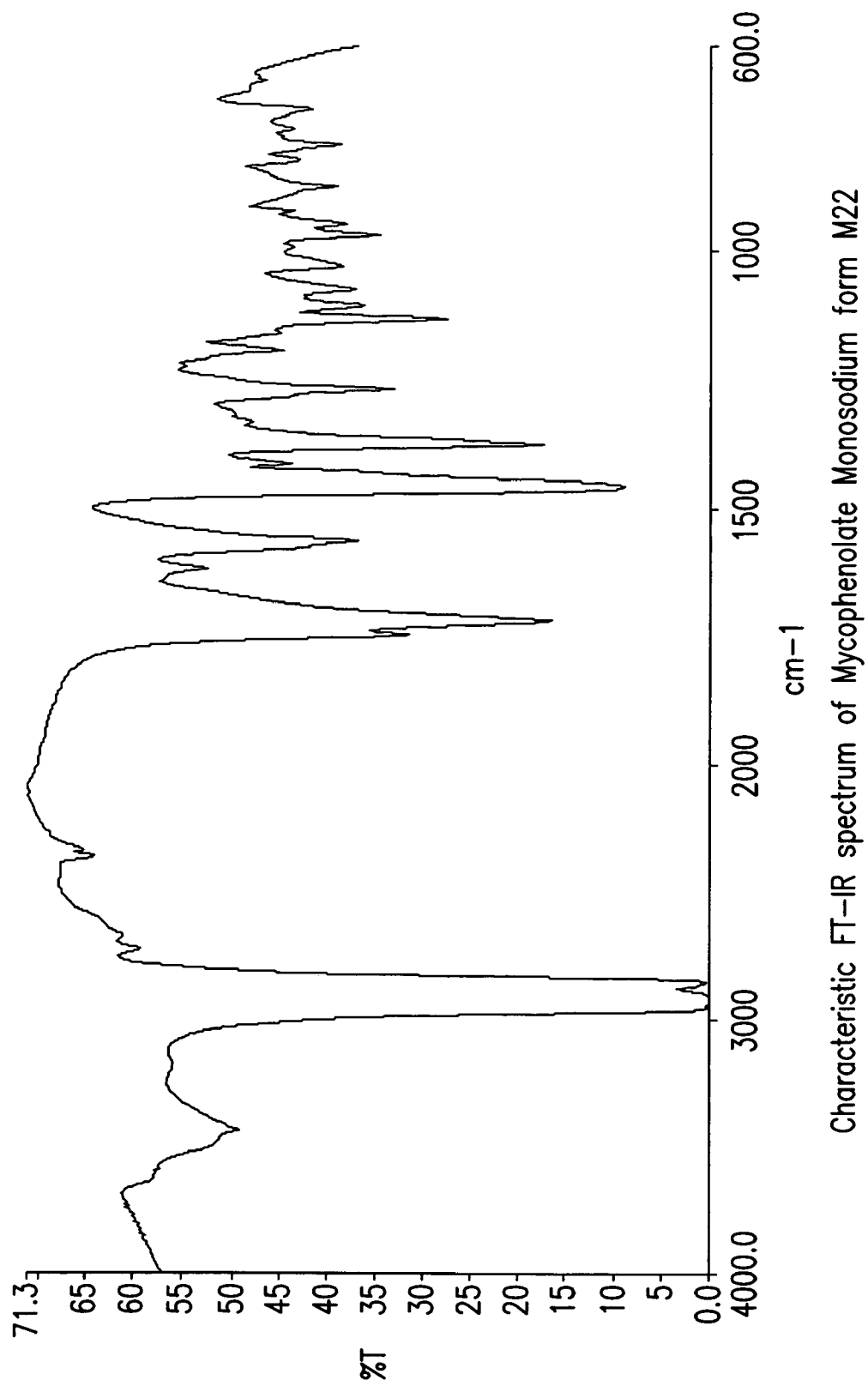
FIG. 38 is a characteristic FTIR spectrum for monosodium mycophenolate form M22.
Figure 39:
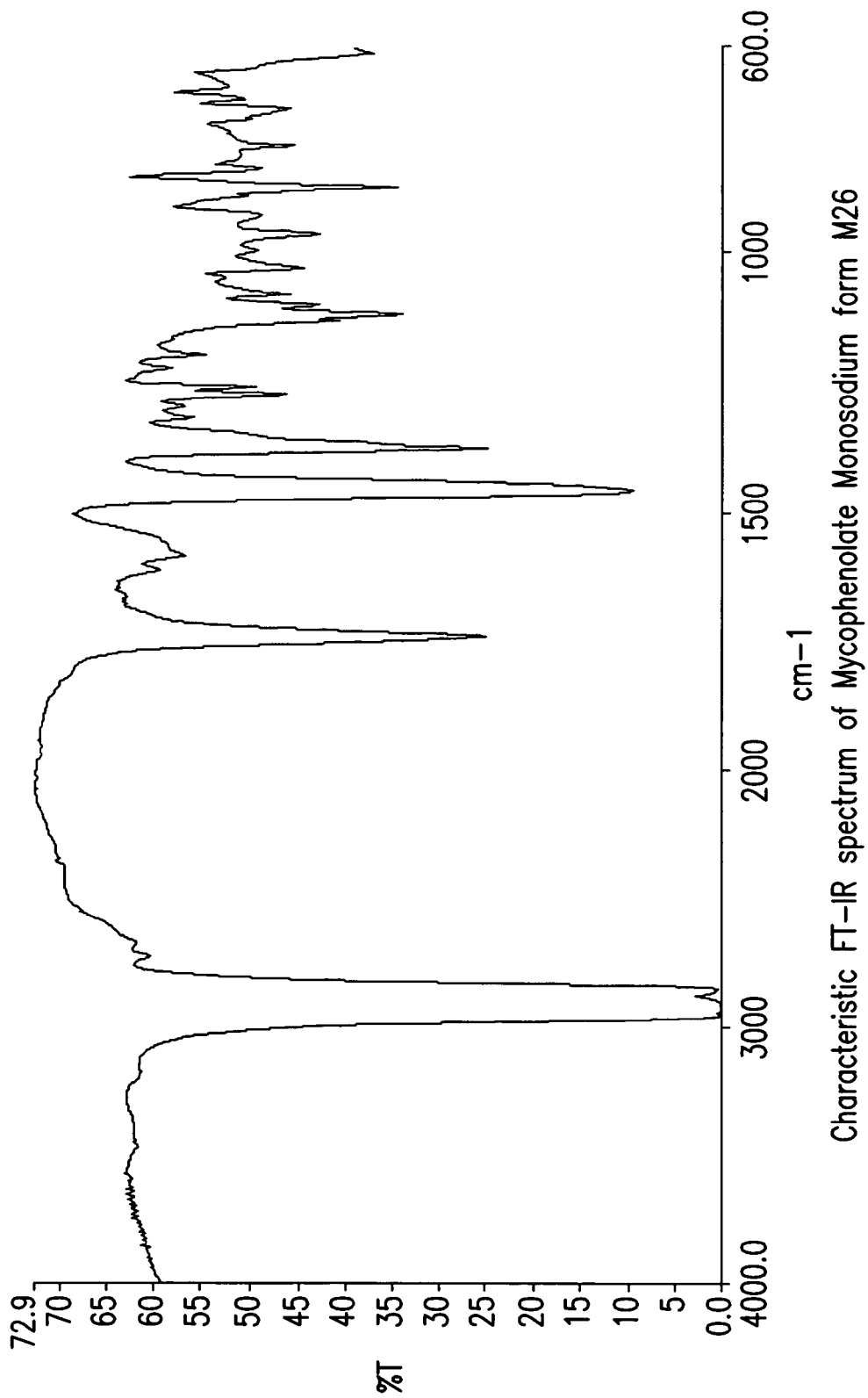
FIG. 39 is a characteristic FTIR spectrum for monosodium mycophenolate form M26.
Figure 40:
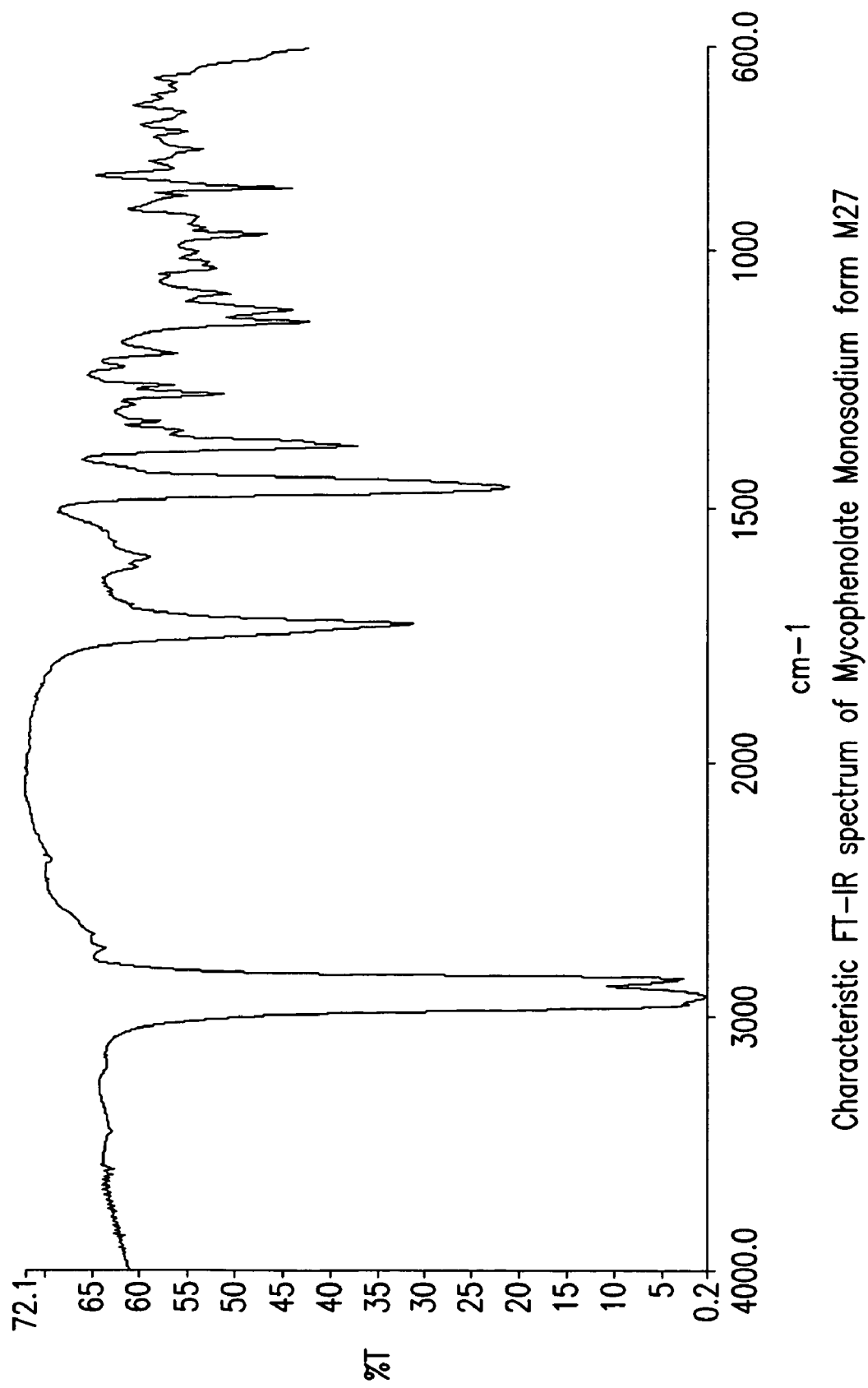
FIG. 40 is a characteristic FTIR spectrum for monosodium mycophenolate form M27.
Figure 41:
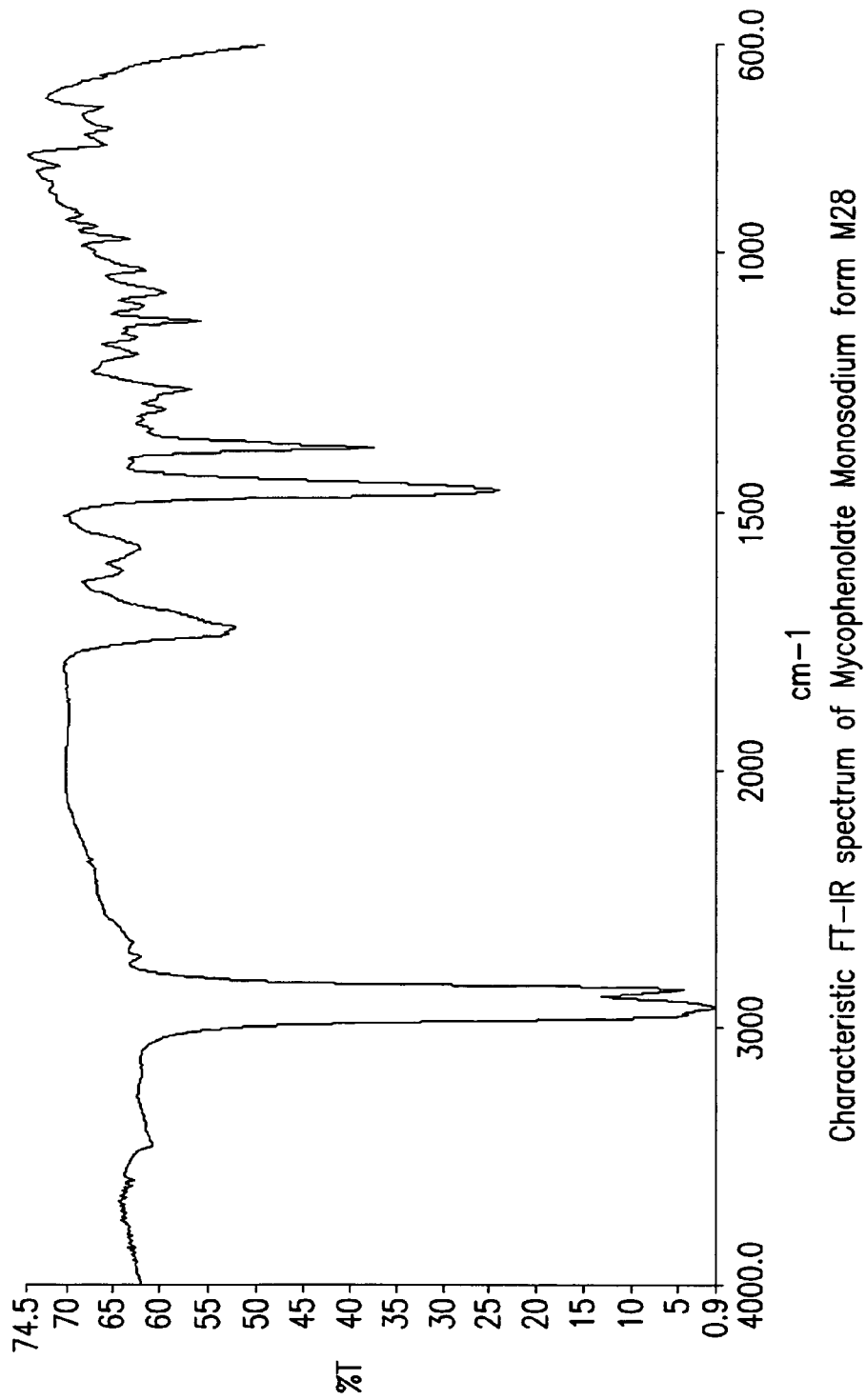
FIG. 41 is a characteristic FTIR spectrum for monosodium mycophenolate form M28.

In another aspect, the present invention is a crystalline disodium mycophenolate, denominated Form D2, characterized by a powder XRD pattern with peaks at 6.2, 8.0, 18.3, 18.5 and 25.3±0.2 degrees 2 theta (FIG. 19). Form D2 may be further characterized by XRD peaks at 22.6 and 23.3±0.2 degrees 2 theta. Form D2 may be further characterized by IR peaks at 1320, 1306, 1210, 1158, 1109, 1037, 976, 937, 922, 880, 838, 808, 760, 722 and 657 cm$^{-1}$. Form D2 may be substantially free of other crystalline forms of mycophenolate sodium.

The invention provides a process for preparing mycophenolate disodium Form D2. First, mycophenolic acid is dissolved in a mixture of dichloromethane and toluene. Second, a base and source of sodium is combined with the solution, preferably sodium methoxide. Third, the crystalline form is concentrated into a residue, preferably by evaporating to dryness. Fourth, acetone and water are combined, preferably in a ratio of about 10:1 to about 30:1 by volume, with the residue to form a precipitate.

Preparation of Polymorphs by Formation of Sodium Mycophenolate

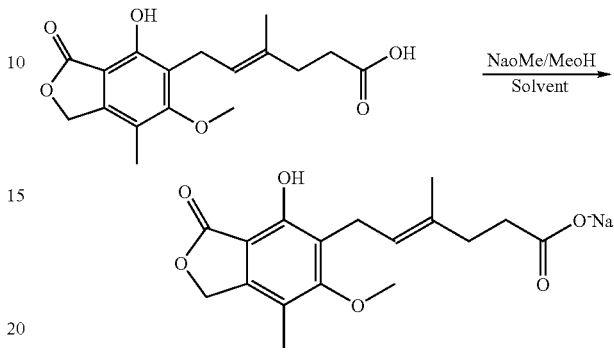

Sodium mycophenolate was obtained when MPA was reacted with methanolic NaOMe in different solvents and the product was crystallized. Form M1 or M2 or M3 were obtained. However, the same reaction resulted in form M4 (in wet form) when the crystallization was performed in methanol at −15° C. for 16-20 hours.

Preparation of Polymorphs by Recrystallization of Sodium Mycophenolate

Polymorphic purity: The crystal forms in the patent contain no more than about 5% of any other crystal forms.

The single particle size measured by polarizing light microscope of crystal forms described in the invention is less than about 100 micrometers.

The hygroscopicity of monosodium mycophenolate crystal forms M1, M2, M3 and disodium mycophenolate crystal forms D1 and D1+D2 were also investigated. Form M1, M2, M3, D1 and D1+D2 were exposed to different level of humidity for one week and after equilibrium they were analysed by TGA and XRD for water content and crystal structure. Table 5 summarizes the results:

TABLE 5

| Crystal forms | Results | | |
|---|---|---|---|
| | % RH | LOD(%) | Form |
| M1 (example 8) | 20 | 4.5 | M1 |
| | 40 | 4.9 | M1 |
| | 60 | 5.1 | M1 |
| | 80 | 5.2 | M1 |
| | 100 | 31.2 | M1 |
| M2 (example 3) | 40 | 0.1 | M2 |
| | 60 | 0.2 | M2 |
| | 80 | 0.4 | M2 |
| | 100 | 45.2 | M1 |
| M3 (example 13 dry) | 40 | 1.5 | M3 >> M1 |
| | 60 | 2.3 | M3 + M1 |
| | 80 | 4.9 | M1 |
| | 100 | 34.3 | M1 |
| D1 (example 44) | 40 | 2.17 | D1 |
| | 60 | 11.64 | D1 + D2 |
| | 80 | 17.20 | D2 |
| | 100 | 31.87 | D2 |
| D1 + D2 (example 45) | 20 | 10.2 | D1 + D2 |
| | 40 | 10.3 | D1 + D2 |
| | 80 | 16.9 | D2 |
| | 100 | 42.1 | D2 |

It can be established from the results that among the forms of monosodium salts, the most stable form at room temperature, at high relative humidity is the monohydrate form M1. Among the disodium salts, form D2 is the most stable form at room temperature, at high relative humidity.

The equilibrium water content of M1 is about 5%. All tested monosodium crystal forms transform to M1 when achieving this water content.

In case of all tested samples, a very high level of water content were measured at 100% relative humidity.

The equilibrium water content of disodium mycophenolate is about 17%. All tested disodium forms transform to crystal form D2 when reaching 17% water content.

Representatives of all monosodium and disodium mycophenolate crystal forms, M1, M2, M1+M3, D1 and D1+D2 were heated in an oven at atmospheric pressure at 130° C. and 170° C. for 30 minutes. The samples were analyzed by XRD before and after heating. Results are summarized in Table 6.

TABLE 6

Crystal forms transformation by heating

| Crystal form before heating (XRD) | Crystal form after heating (XRD) | |
|---|---|---|
| | 130° C., 30 min. | 170° C., 30 min. |
| M1 | M3 >>M1 | No data |
| M2 | M2 | M2 |
| M1 + M3 | M3 > Ml | M2 |
| D1 | D1 | D1 |
| D1 + D2 | D1 | No data |

It can be seen in the table that heating of the sodium mycophenolate samples causes mostly change in the crystal form, except for form M2 of Monosodium salt and form D1 of Disodium salt. These forms are the most stable forms at high temperature.

Forms M15-M28 were studies by DSC, TGA and KF. The DSC curves of the forms of mycophenolate monosodium indicates endothermic peaks due to dehydration, desolvation and melting.

TABLE

Thermal analysis and KF data of mycophenolate monosodium forms

| XRD form | DSC (° C.) | DSC (J/g) | TGA (° C.) | TGA LOD(%) | KF LOD(%) |
|---|---|---|---|---|---|
| M15 | 96.9 | 60 | 26-96 | 22.5 | 1.0 |
| | 191.4 | 63 | 135-191 | 7.8 | |
| | 197.8 | 70 | | | |
| M15 | 71.3 | 13 | 26-95 | 0.3 | 0.8 |
| | 189.6 | 60 | 144-190 | 10.2 | |
| | 197.7 | 77 | | | |
| M16 | 100.0 | 28 | 28-108 | 3.2 | |
| | 209.3 | 75 | 107-171 | 2.2 | |
| | | | 172-209 | 1.2 | |
| M16 | 77.7 | 16 | 28-91 | 3.8 | 7.6 |
| | 92.0 | 23 | 92-172 | 2.7 | |
| | 101.4 | 49 | | | |
| | 208.6 | 105 | 172-210 | 1.1 | |
| | 212.1 | 84 | | | |
| M17 | 95.3 | 48 | 28-89 | 2.6 | |
| | | | 91-170 | 1.4 | |
| | 186.9 | 68 | 170-202 | 0.5 | |
| M17 | 71.0 | 2 | 28-88 | 2.3 | 4.2 |
| | 90.7 | 40 | 90-174 | 1.5 | |
| | 183.5 | 46 | | | |
| | 200.1 | 7 | 175-203 | 0.4 | |
| M18 | 54.0 | 4 | 24-94 | 19.0 | |
| | | | 94-165 | 1.2 | |
| | 189.8 | 92 | 165-200 | 0.4 | |

TABLE-continued

Thermal analysis and KF data of mycophenolate monosodium forms

| XRD form | DSC (° C.) | DSC (J/g) | TGA (° C.) | TGA LOD(%) | KF LOD(%) |
|---|---|---|---|---|---|
| M18 | 81.9 | 5 | 27-92 | 0.8 | 3.3 |
| | | | 92-169 | 1.6 | |
| | 185.9 | 102 | 169-206 | 0.8 | |
| M19 | 109.8 | 8 | 27-122 | 10.2 | |
| | 145.6 | 86 | 122-161 | 9.8 | |
| | 189.4 | 5 | 162-189 | 0.7 | |
| M20 | 72.6 | 2 | 24-128 | 7.6 | |
| | 127.2 | 3 | | | |
| | 178.5 | 78 | 132-202 | 1.4 | |
| M21 | 94.4 | 42 | 25-167 | 2.4 | |
| | 111.1 | 297 | 67-118 | 12.9 | |
| | | | 118-179 | 1.2 | |
| | 221.4 | 49 | | | |
| M22 | 103.2 | 53 | 28-53 | 0.1 | 3.1 |
| | 109.7 | 29 | 53-133 | 3.7 | |
| | 190.9 | 104 | | | |
| M26 | 98.6 | 65 | 26-91 | 19.8 | |
| | 103.1 | 49 | 91-144 | 10.0 | |
| | 189.3 | 44 | 150-191 | 4.5 | |
| | 199.6 | 64 | 192-229 | 2.8 | |
| M27 | 78.6 | 25 | 26-126 | 5.0 | 0.5 |
| | | | 126-185 | 7.3 | |
| | 190.5 | 83 | 185-230 | 3.1 | |
| | 196.4 | 78 | | | |
| M28 | 112.4 | 59 | | | 1.8 |
| | 131.4 | 6 | 27-152 | 18.8 | |
| | 154.3 | 15 | | | |
| | 184.9 | 46 | | | |
| M28 | 86.7 | 15 | 28-89 | 1.4 | 1.4 |
| | 105.9 | 46 | 89-150 | 14.0 | |
| | 154.1 | 22 | | | |
| | 184.4 | 54 | | | |

Based on the TGA and Karl Fischer results, forms M15, M19, M20, M21, M26, M27, and M28 are solvates. Forms M16, M17, M18, and M22 are hydrates.

The present invention polymorphic forms preferably contains less than 30%, more preferably less than 20%, more preferably less than 10% of other polymorphic forms by weight. The single particle size for the polymorphs of the present invention is less than about 100 micrometers, as measured by polarizing light microscope of crystal described in the invention The starting material used for the processes of the present invention, unless otherwise specified, may be any crystalline or amorphous form of mycophenolate sodium or acid, including various solvates and hydrates.

The processes of the present invention may also be practiced as the last step of prior art processes that synthesize mycophenolate sodium.

The base and the source of sodium as used throughout this invention can be different, or they can be the same. For example, sodium methoxide, sodium ethoxide, or sodium hydroxide can be used as both the base and the source of sodium. The preferred base and source of sodium is sodium methoxide.

Many processes of the present invention involve crystallization out of a particular solvent. One skilled in the art would appreciate that the conditions concerning crystallization may be modified without affecting the form of the polymorph obtained. For example, when mixing mycophenolate sodium in a solvent to form a solution, warming of the mixture may be necessary to completely dissolve the starting material. If warming does not clarify the mixture, the mixture may be diluted or filtered. To filter, the hot mixture may be passed through paper, glass fiber or other membrane material, or a clarifying agent such as celite. Depending upon the equipment used and the concentration and temperature of the solution, the filtration apparatus may need to be preheated to avoid premature crystallization.

The conditions may also be changed to induce precipitation. A preferred way of inducing precipitation is to reduce the solubility of the solvent. The solubility of the solvent may be reduced, for example, by cooling the solvent or adding an anti-solvent.

In one embodiment, an anti-solvent is added to a solution to decrease its solubility for a particular compound, thus resulting in precipitation. Another way of accelerating crystallization is by seeding with a crystal of the product or scratching the inner surface of the crystallization vessel with a glass rod.

Pharmaceutical compositions of the present invention contain mycophenolate sodium Form M2. In addition to the active ingredient(s), the pharmaceutical compositions of the present invention may contain one or more excipients. Excipients are added to the composition for a variety of purposes.

Diluents increase the bulk of a solid pharmaceutical composition and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage Form like a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of non-compacted solid composition and improve the accuracy of dosing. Excipients that may function as glidants include colloidal silicon dixoide, magnesium trisilicate, powdered cellulose, starch, talc and tribasic calcium phosphate.

When a dosage Form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product Form the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage Form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention hydrochloride Forms and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste. Preservatives and chelating agents such as alcohol, sodium benzoate, butylated hydroxy toluene, butylated hydroxyanisole and ethylenediamine tetraacetic acid may be added at levels safe for ingestion to improve storage stability.

A liquid composition according to the present invention may also contain a buffer such as guconic acid, lactic acid, citric acid or acetic acid, sodium guconate, sodium lactate, sodium citrate or sodium acetate.

Selection of excipients and the amounts to use may be readily determined by the Formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage Form and prepared by any of the methods well-known in the pharmaceutical arts.

Dosage Forms include solid dosage Forms like tablets, powders, capsules, suppositories, sachets, troches and lozenges as well as liquid syrups, suspensions and elixirs.

A dosage Form of the present invention is a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be Formulated into compositions and dosage Forms according to methods known in the art.

A composition for tableting or capsule filing may be prepared by wet granulation. In wet granulation some or all of the active ingredients and excipients in powder Form are blended and then further mixed in the presence of a liquid, typically water, that causes the powders to clump up into granules. The granulate is screened and/or milled, dried and then screened and/or milled to the desired particle size. The granulate may then be tableted or other excipients may be added prior to tableting such as a glidant and or lubricant.

A tableting composition may be prepared conventionally by dry blending. For instance, the blended composition of the actives and excipients may be compacted into a slug or a sheet and then comminuted into compacted granules. The compacted granules may be compressed subsequently into a tablet.

As an alternative to dry granulation, a blended composition may be compressed directly into a compacted dosage Form using direct compression techniques. Direct compression produces a more uniform tablet without granules. Excipients that are particularly well suited to direct compression tableting include microcrystalline cellulose, spray dried lactose, dicalcium phosphate dihydrate and colloidal silica. The proper use of these and other excipients in direct compression tableting is known to those in the art with experience and skill in particular Formulation challenges of direct compression tableting.

A capsule filling of the present invention may comprise any of the aforementioned blends and granulates that were described with reference to tableting, only they are not subjected to a final tableting step.

Experimental Methodology (Physical)

XRD

ARL X-ray powder diffractometer model X'TRA-030, Peltier detector, round standard aluminum sample holder with round zero background quartz plate was used. Scanning parameters: Range: 2-40 deg. 2 θ, continuous Scan, Rate: 3 deg./min. The accuracy of peak positions is defined as +/−0.2 degrees due to experimental differences like instrumentations, sample preparations etc.

FTIR Spectroscopy

Perkin-Elmer Spectrum 1000 Spectrometer, at 4 $cm^{-1}$ resolution with 16 scans, in the range of 4000-400 $cm^{-1}$ was used. The samples were analyzed in Nujol mull. The spectra were recorded using an empty cell as a background.

Differential Scanning Calorimetry (DSC)

DSC $822^e$/700, Mettler Toledo, Sample weight: 3-5 mg. Heating rate: 10° C./min., Number of holes of the crucible: 3 In $N_2$ stream: flow rate=40 ml/min
Scan range: 30-250° C., 10° C./minutes heating rate.

The DSC curves of the novel forms of mycophenolate monosodium indicates only endothermic peaks due to dehydration, desolvation and melting.

Thermal Gravimetric Analysis (TGA)

TGA/SDTA $851^e$, Mettler Toledo, Sample weight 7-15 mg. Heating rate: 10° C./min., In $N_2$ stream: flow rate=50 ml/min
Scan range: 30-250° C.

Microscope

The particle size of single crystals was observed by a polarizing light Microscope, Type: Zeiss TOPIC-B. Sample preparation was done by dispersing a sample in one drop of mineral oil. The magnification was 200.

Abbreviations
MPA=Mycophenolic acid
NaOMe=Sodium methoxide
DMF=Dimethyl formamide Preparation of Mycophenolate Monosodium Crystal Forms

EXAMPLE 1

To a stirred solution of MPA (6.4 g) in methanol (32 ml), 30% sodium methoxide in methanol (3.8 ml) was added dropwise at room temperature. The reaction mixture was stored at −15° C. After 3 hours, the precipitated product was filtered and then washed with cold methanol. The solid material was dried at 40-45° C. in a vacuum oven. Form M1 of mycophenolate sodium was obtained in 48% yield.

EXAMPLE 2

To a stirred solution of MPA (6.4 g) in methanol (64 ml), 30% sodium methoxide in methanol (3.8 ml) was added dropwise at room temperature. The reaction mixture was cooled to −15° C. within 1 hour and stirred at this temperature for an additional 2 hours. The precipitated product was filtered and then washed with cold methanol. The solid material was dried at 40-45° C. in a vacuum oven. Form M1 of mycophenolate sodium was obtained in 54% yield.

EXAMPLE 3

To a stirred solution of MPA (6.4 g) in methanol (32 ml), 30% sodium methoxide in methanol (4.5 ml) was added dropwise at room temperature. After stirring at room temperature for 0.5 h, the reaction mixture was stored at −15° C. After 1.5 hours, the precipitated product was filtered off and washed with cold methanol. The solid material was dried at 40-45° C. in a vacuum oven. Form M1 of mycophenolate sodium was obtained in 43% yield.

Examples of Mixtures

EXAMPLE 4

To a stirred solution of MPA (6.4 g) in methanol (64 ml) 30% of sodium methoxide in methanol (3.8 ml) was added dropwise at room temperature. The reaction mixture was cooled to −15° C. within 1 hour and stirred at this temperature for additional 20 hours. The precipitated product was filtered, then washed with cold methanol. A part of the solid material was dried at 40-45° C. in vacuum oven. The yield was 40%. Forms M4>>M1 of mycophenolate sodium were obtained from the wet sample. Form M3 of mycophenolate sodium was obtained from the dry sample.

EXAMPLE 5

To a stirred solution of MPA (6.4 g) in methanol (64 ml) 30% of sodium methoxide in methanol (3.8 ml) was added dropwise at room temperature. The reaction mixture was stored at −15° C. After 24 hours the precipitated product was filtered off and washed with cold methanol. The solid material was dried at 40-45° C. in vacuum oven. The yield was 60%. Forms M1+M3 of mycophenolate sodium were obtained.

EXAMPLE 6

To a stirred solution of MPA (6.4 g) in methanol (32 ml) 30% of sodium methoxide in methanol (3:8 ml) was added dropwise at room temperature. The reaction mixture was stored at −15° C. After 24 hours the precipitated product was filtered off and washed with cold methanol. The solid material was dried at 40-45° C. in vacuum oven. The yield was 72%. Forms M1+M3 of mycophenolate sodium were obtained.

EXAMPLE 7

To a stirred solution of MPA (6.4 g) in methanol (32 ml) sodium hydroxide (0.8 g) in water (2 ml) was added dropwise at room temperature. The stirring was continued at this temperature for 0.5 hours. The precipitated product was filtered off and washed with cold methanol. The solid material was dried at 40-45° C. in vacuum oven. The yield was 43%. Forms M1+M3 of mycophenolate sodium were obtained.

EXAMPLE 8

To a stirred solution of MPA (12.8 g) in methanol (64 ml) 30% of sodium methoxide in methanol (7.4 ml) was added dropwise at room temperature. The reaction mixture was cooled to −15° C. within 5 hours and stirred at this temperature for additional 17 hours. The precipitated product was filtered, then washed with cold methanol. A part of the solid material was dried at 40-45° C. in vacuum oven. The yield was 65%. Form M4 of mycophenolate sodium was obtained from the wet sample. Forms M1+M2+M3 of mycophenolate sodium were obtained from the dry sample.

EXAMPLE 9

To a stirred solution of MPA (12.8 g) in methanol (128 ml) 30% of sodium methoxide in methanol (7.4 ml) was added dropwise at room temperature. The reaction mixture was cooled to −15° C. within 5 hours and stirred at this temperature for additional 17 hours. The precipitated product was filtered, then washed with cold methanol. A part of the solid material was dried at 40-45° C. in vacuum oven. The yield was 37%. Form M4 of mycophenolate sodium was obtained from the wet sample. Forms M1+M2+M3 of mycophenolate sodium were obtained from the dry sample.

EXAMPLE 10

To a stirred solution of MPA (16 g) in acetonitrile (500 ml) 30% of sodium methoxide in methanol (9.3 ml) was added dropwise at 40° C. The reaction mixture was cooled to room temperature, then stirred for additional 30 minutes at this temperature The precipitated product was filtered off and washed with acetonitrile. A part of the solid material was dried at 40-45° C. in vacuum oven. The yield was 86%. Form M10 of mycophenolate sodium was obtained from the wet sample. Form M11 of mycophenolate sodium was obtained from the dry sample.

EXAMPLE 11

To a stirred solution of MPA (16 g) in acetonitrile (500 ml), 30% sodium methoxide in methanol (9.3 ml) was added dropwise at 40° C. The reaction mixture was cooled to room temperature and then stirred for an additional 30 minutes at this temperature. The precipitated product was filtered off and washed with acetonitrile. A part of the solid material was dried at 40-45° C. in a vacuum oven. The yield was 86%. Form M10 of mycophenolate sodium was obtained from the wet sample. Form M11 of mycophenolate sodium was obtained from the dry sample.

EXAMPLE 12

Sodium mycophenolate (1 g) was heated to reflux temperature in 1,4-dioxane (400 ml). The salt was not dissolved completely. The mixture was allowed to cool to room temperature, and crystallized at this temperature overnight. The solid was filtered off, and a part of the wet material was dried at normal pressure at room temperature. Form M5 of mycophenolate sodium was obtained from both the wet sample and the dry sample. Water content of the dry sample was 1.8% measured by KF.

EXAMPLE 13

Sodium mycophenolate (1 g) was dissolved at reflux temperature in absolute ethanol (165 ml). The solution was allowed to cool to room temperature, and crystallized at this temperature overnight. The solid was filtered off, and a part of the wet material was dried at normal pressure at room temperature. Form M1 of mycophenolate sodium was obtained from the wet sample. Form M2 of mycophenolate sodium was obtained from the dry sample.

EXAMPLE 14

Sodium mycophenolate (1 g) was dissolved at reflux temperature in 1-butanol (175 ml). The solution was allowed to cool to room temperature, and crystallized at this temperature overnight. The solid was filtered off, and a part of the wet material was dried at normal pressure at room temperature. Form M2 of mycophenolate sodium was obtained from both the dry and the wet sample.

EXAMPLE 15

Sodium mycophenolate (1 g) was dissolved at about 60° C. in water (5 ml). The solution was allowed to cool to room temperature. The solution was then allowed to evaporate to dryness at room temperature in an open dish. Form M1 of mycophenolate sodium was obtained

EXAMPLE 16

Sodium mycophenolate (1 g) was dissolved at about 60° C. in water (5 ml). The solution was allowed to cool to room temperature, then acetone (55 ml) was added to the solution. The product was precipitated, and the mixture was allowed to crystallize at room temperature overnight. The solid was filtered off, and a part of the wet material was dried at normal pressure at room temperature. Form M6 of mycophenolate sodium was obtained from both the dry and the wet sample. Water content of the wet sample was 21.0, and of the dry sample was 20.0% by KF.

EXAMPLE 17

Sodium mycophenolate (0.5 g) was dissolved at about 60° C. in ethyl lactate (5 ml). The solution was allowed to cool to room temperature, then ethyl acetate (300 ml) was added to the solution. The solution was stored at ±4° C. overnight. The solid was filtered off and a part of the wet material was dried at normal pressure at room temperature. Form. M8 of mycophenolate sodium was obtained from both the dry and the wet sample. Water content of the dry sample was 2.1% by KF.

EXAMPLE 18

Sodium mycophenolate (0.5 g) was dissolved at about 60° C. in DMF (5 ml). The solution was allowed to cool to room temperature, then acetone (300 ml) was added to the solution. The solution was stored at +4° C. overnight. The solid was filtered off, and a part of the wet material was dried at normal pressure at room temperature. Form M7 of mycophenolate sodium was obtained from both the dry and the wet sample. Water content of the dry sample was 2.1% by KF.

EXAMPLE 19

Sodium mycophenolate (1 g) was dissolved at room temperature in methanol (15 ml), then methylene chloride (280 ml) was added to the solution. The solution was allowed to stand at room temperature overnight to promote crystallization of the product. The solid was then filtered off, and a part of the wet material was dried at normal pressure at room temperature. Form M9 of mycophenolate sodium was obtained from both the wet and the dry sample. Water content of the dry sample was 4.5% by KF.

EXAMPLE 20

Sodium mycophenolate (1 g, example 5) was dissolved at about 60° C. in water (5 ml). The solution was allowed to cool to room temperature, then 2-propanol (80 ml) was added to the solution. The product was precipitated, and the mixture was allowed to crystallize at room temperature overnight. The solid was filtered off, and a part of the wet material was dried at normal pressure at room temperature. Forms M1+M6 of mycophenolate sodium were obtained from the wet sample. Forms M1>M2 of mycophenolate sodium were obtained from the dry sample.

EXAMPLE 21

Sodium mycophenolate (1 g) was dissolved at room temperature in water (100 ml), then the solution was filtered. The filtrate was lyophilized overnight. Form M12 of mycophenolate sodium was obtained

EXAMPLE 22

Sodium mycophenolate (12 g,) was refluxed in 1,4-dioxane (240 ml). The salt did not dissolve totally. The mixture was allowed to cool to room temperature, and crystallized at this temperature for 3 days. The solid was filtered off, and the polymorphism was determined by X-ray diffraction from this wet sample. The obtained material was form M15. A part of the wet sample was dried at normal pressure at room temperature. Polymorphism was determined by X-ray diffraction. The obtained material was form M15.

EXAMPLE 23

Sodium mycophenolate (1 g,) was heated to reflux temperature in 4-methyl-2-pentanone (400 ml). The salt did not dissolve totally. The mixture was allowed to cool to room temperature, and crystallized at this temperature for 16 hours. The solid was filtered off, and the polymorphism was determined by X-ray diffraction from this wet sample. The obtained material was form M16. A part of the wet sample was dried at normal pressure at room temperature. Polymorphism was determined by X-ray diffraction. The obtained material was form M16.

EXAMPLE 24

Sodium mycophenolate (0.5 g, example 5) was dissolved at about 60° C. in DMF (5 ml). The solution was allowed to cool to room temperature, then 2-propanol (300 ml) was added to the solution. The solution was stored at +4° C. overnight. The solid was filtered off, and a part of the wet material was dried at normal pressure at room temperature. Forms M1+M2 of mycophenolate sodium were obtained from the wet sample. Form M2 of mycophenolate sodium was obtained from the dry sample.

EXAMPLE 25

Sodium mycophenolate (1 g,) was heated to reflux temperature in dimethylcarbonate (400 ml). The salt did not dissolve totally. The mixture was allowed to cool to room temperature, and crystallized at this temperature for 16 hours. The solid was filtered off, and the polymorphism was determined by X-ray diffraction from this wet sample. The obtained material was form M17. A part of the wet sample was dried at normal pressure at room temperature. Polymorphism was determined by X-ray diffraction. The obtained material was form M17.

EXAMPLE 26

Sodium mycophenolate (1 g,) was heated to reflux temperature in 2-methyl-2-propanol (400 ml). The salt did not dissolve totally. The mixture was allowed to cool to room temperature, and crystallized at this temperature for 16 hours. The solid was filtered off, and the polymorphism was determined by X-ray diffraction from this wet sample. The obtained material was form M18. A part of the wet sample was dried at normal pressure at room temperature. Polymorphism was determined by X-ray diffraction. The obtained material was form M18.

EXAMPLE 27

Sodium mycophenolate (1 g,) was dissolved at room temperature in methanol (15 ml). Carbon tetrachloride (250 ml) was added to the solution. After some minutes separation of crystals started. The solution was put into fridge for 16 hours. The formed crystals were filtered off, and the polymorphism was determined by X-ray diffraction from this wet sample. The obtained material was form M19.

EXAMPLE 28

Sodium mycophenolate (1 g,) was dissolved in N,N-dimethyl-acetamide (19 ml). Acetonitrile (400 ml) was added to the solution. The solution was put into the fridge for 16 hours. The formed crystals were filtered off, and the polymorphism was determined by X-ray diffraction from this wet sample. The obtained material was form M20.

EXAMPLE 29

Sodium mycophenolate (1 g,) was heated to reflux temperature in a mixture of water (20 ml) and 1,4-dioxane (380 ml). Water (10 ml) was added, the salt dissolved totally. The solution was allowed to cool to room temperature, dioxane (150 ml) was added, then put into fridge for 16 hours. The solid was filtered off, dried at normal pressure at room temperature. Polymorphism was determined by X-ray diffraction. The obtained material was form M21.

EXAMPLE 30

Mycophenolic acid (3.20 g, 10 mmol) was dissolved in dichloromethane (64 ml). To this solution sodium methoxide (9 mmol, 1.67 ml of its 30% methanolic solution) was added under stirring. The formed suspension was diluted with 256 ml of dichloromethane. After 2 hours stirring at room temperature the solid was filtered off, dried at normal pressure at room temperature. Polymorphism was determined by X-ray diffraction. The obtained material was form M22.

EXAMPLE 31

Mycophenolic acid (3.20 g, 10 mmol) was dissolved in 1,4-dioxane (64 ml). To this solution sodium methoxide (9 mmol, 1.67 ml of its 30% methanolic solution) was added under stirring. After 1 hour stirring at room temperature the solid was filtered off. The polymorphism was determined by X-ray diffraction from this wet sample. The obtained material was form M26.

EXAMPLE 32

A part of the wet sample obtained by method described in Example 35 was dried at normal pressure at room temperature. Polymorphism was determined by X-ray diffraction. The obtained material was form M27.

EXAMPLE 33

Mycophenolic acid (3.20 g, 10 mmol) was dissolved in carbon-tetrachloride (180 ml). To this slightly opal solution sodium methoxide (9 mmol, 1.67 ml of its 30% methanolic solution) was added under stirring. After 3 hour stirring at room temperature the mixture was put into fridge for 16 hours. The solid was filtered off, and the polymorphism was determined by X-ray diffraction from this wet sample. The obtained material was form M28. A part of the wet sample was dried at normal pressure at room temperature. Polymorphism was determined by X-ray diffraction. The obtained material was form M28.

Preparation of Mycophenolate Disodium Crystal Forms

EXAMPLE 34

To a stirred solution of MPA (6.4 g) in methanol (128 ml), sodium carbonate (4.24 g) was added at room temperature. The mixture was stirred at room temperature for 4 hours, then it was filtered. The filtrate was evaporated on a rotary evaporator to about 50 ml and the concentrated solution was stored at −15° C. for overnight. The precipitated product was filtered off and washed with methanol. The solid material was dried at 40-45° C. in a vacuum oven. The yield was 20%. Polymorphism was determined by X-ray diffraction. The obtained material was form D1

EXAMPLE 35

To a stirred solution of MPA (5 g) in dichloromethane (90 ml) and toluene (180 ml), methanolic sodium methoxide (5.9 ml 30% sodium methoxide in methanol diluted with 78 ml of methanol) was added at room temperature. The mixture was stirred at room temperature for 20 minutes and evaporated to dryness. The residue was suspended in 95:5 acetone:water, then the precipitated product was filtered off and washed with cold acetone. The solid material was dried at 40-45° C. in a vacuum oven. The yield was 85%. Polymorphism was determined by X-ray diffraction. The obtained material was form D2

Preparation of Mycophenolate Monosodium Crystal Forms

EXAMPLE 36

Preparation of Form M15 of Sodium Mycophenolate

Sodium mycophenolate (12 g, 533-90) was refluxed in 1,4-dioxane (240 ml). The salt did not dissolve totally. The mixture was allowed to cool to room temperature, and crystallized at this temperature for 3 days. The solid was filtered off, and the polymorphism was determined by X-ray diffraction from this wet sample. The obtained material was form M15. A part of the wet sample was dried at normal pressure at room temperature. Polymorphism was determined by X-ray diffraction. The obtained material was form M15.

EXAMPLE 37

Preparation of Form M16 of Sodium Mycophenolate

Sodium mycophenolate (1 g, 533-69) was heated to reflux temperature in 4-methyl-2-pentanone (400 ml). The salt did not dissolve totally. The mixture was allowed to cool to room temperature, and crystallized at this temperature for 16 hours. The solid was filtered off, and the polymorphism was determined by X-ray diffraction from this wet sample. The obtained material was form M16. A part of the wet sample was dried at normal pressure at room temperature. Polymorphism was determined by X-ray diffraction. The obtained material was form M16.

EXAMPLE 38

Preparation of Form M17 of Sodium Mycophenolate

Sodium mycophenolate (1 g, 533-69) was heated to reflux temperature in dimethylcarbonate (400 ml). The salt did not dissolve totally. The mixture was allowed to cool to room temperature, and crystallized at this temperature for 16 hours. The solid was filtered off, and the polymorphism was determined by X-ray diffraction from this wet sample. The obtained material was form M17. A part of the wet sample was dried at normal pressure at room temperature. Polymorphism was determined by X-ray diffraction. The obtained material was form M17.

EXAMPLE 39

Preparation of Form M18 of Sodium Mycophenolate

Sodium mycophenolate (1 g, 533-69) was heated to reflux temperature in 2-methyl-2-propanol (400 ml). The salt did not dissolve totally. The mixture was allowed to cool to room temperature, and crystallized at this temperature for 16 hours. The solid was filtered off, and the polymorphism was determined by X-ray diffraction from this wet sample. The obtained material was form M18. A part of the wet sample was dried at normal pressure at room temperature. Polymorphism was determined by X-ray diffraction. The obtained material was form M18.

EXAMPLE 40

Preparation of Form M19 of Sodium Mycophenolate

Sodium mycophenolate (1 g, 533-69) was dissolved at room temperature in methanol (15 ml). Carbon tetrachloride (250 ml) was added to the solution. After some minutes separation of crystals started. The solution was put into fridge for 16 hours. The formed crystals were filtered off, and the polymorphism was determined by X-ray diffraction from this wet sample. The obtained material was form M19.

EXAMPLE 41

Preparation of Form M20 of Sodium Mycophenolate

Sodium mycophenolate (1 g, 533-69) was dissolved in N,N-dimethyl-acetamide (19 ml). Acetonitrile (400 ml) was added to the solution. The solution was put into the fridge for 16 hours. The formed crystals were filtered off, and the polymorphism was determined by X-ray diffraction from this wet sample. The obtained material was form M20.

EXAMPLE 42

Preparation of Form M21 of Sodium Mycophenolate

Sodium mycophenolate (1 g, 533-69) was heated to reflux temperature in a mixture of water (20 ml) and 1,4-dioxane (380 ml). Water (10 ml) was added, the salt dissolved totally. The solution was allowed to cool to room temperature, dioxane (150 ml) was added, then put into fridge for 16 hours. The solid was filtered off, dried at normal pressure at room temperature. Polymorphism was determined by X-ray diffraction. The obtained material was form M21.

EXAMPLE 43

Preparation of Form M22 of Sodium Mycophenolate

Mycophenolic acid (3.20 g, 10 mmol) was dissolved in dichloromethane (64 ml). To this solution sodium methoxide (9 mmol, 1.67 ml of its 30% methanolic solution) was added under stirring. The formed suspension was diluted with 256 ml of dichloromethane. After 2 hours stirring at room temperature the solid was filtered off, dried at normal pressure at room temperature. Polymorphism was determined by X-ray diffraction. The obtained material was form M22.

EXAMPLE 44

Preparation of Form M26 of Sodium Mycophenolate

Mycophenolic acid (3.20 g, 10 mmol) was dissolved in 1,4-dioxane (64 ml). To this solution sodium methoxide (9 mmol, 1.67 ml of its 30% methanolic solution) was added under stirring. After 1 hour stirring at room temperature the solid was filtered off. The polymorphism was determined by X-ray diffraction from this wet sample. The obtained material was form M26.

EXAMPLE 45

Preparation of Form M27 of Sodium Mycophenolate

A part of the wet sample obtained by method described in Example 9 was dried at normal pressure at room temperature. Polymorphism was determined by X-ray diffraction. The obtained material was form M27.

EXAMPLE 46

Preparation of Form M28 of Sodium Mycophenolate

Mycophenolic acid (3.20 g, 10 mmol) was dissolved in carbon-tetrachloride (180 ml). To this slightly opal solution sodium methoxide (9 mmol, 1.67 ml of its 30% methanolic solution) was added under stirring. After 3 hour stirring at room temperature the mixture was put into fridge for 16 hours. The solid was filtered off, and the polymorphism was determined by X-ray diffraction from this wet sample. The obtained material was form M28. A part of the wet sample was dried at normal pressure at room temperature. Polymorphism was determined by X-ray diffraction. The obtained material was form M28.

Transformation of M1+M3 to M2 by Heating

EXAMPLE 47

200 mg of a mixture of Forms M1+M3 as identified by XRD, was put into an oven in a glass weighing bottle at 170° C. for 0.5 h. Then it was put into a desiccator and allowed to cool to room temperature. Upon XRD analysis, its crystal form was found to be Form M2.

Transformation of M2 to M1, M3 to M1 and D1 to D2 by Water Vapors Absorption

EXAMPLE 48

200 mg of each of the following samples: crystal Form M2, crystal Form M3 and crystal Form D1 were put at room temperature into a hygroscopicity chamber containing 100% relative humidity for one week. After one week they were measured again by XRD to determine their crystal forms. Crystal forms M2 and M3 transformed to M1 and crystal Form D1 transformed to Form D2.

Reproduction of Literature Methods

EXAMPLE 49

*Acta Cryst. Sect. C,* C56 (2000) 432-433

To a stirred solution of MPA (9.6 g) in methanol (300 ml), 30% sodium methoxide in methanol (5.6 ml) was added dropwise at room temperature. The reaction mixture was stirred for an additional 60 minutes, then the solvent was evaporated on a rotary evaporator at 40-45° C. under vacuum. The wet material was dried at 40-45° C. in a vacuum oven and proved to be a mixture of Forms M2 and M3.

EXAMPLE 50

*J. Med. Chem.,* 39 (1996) 1236-1242

To a stirred solution of MPA (9.6 g) in absolute ethanol (360 ml), 21% sodium ethoxide in ethanol (8.6 ml) was added dropwise at room temperature. The reaction mixture was stirred for an additional 60 minutes, then the solvent was evaporated on a rotary evaporator at 40-45° C. under vacuum. The wet material was dried at 40-45° C. in a vacuum oven and proved to be Form M2.

EXAMPLE 51

ZA 68/4,959

To a stirred solution of MPA (13 g) in chloroform (650 ml), sodium methoxide solution (2.3 g NaOMe dissolved in 130 ml of methanol) was added dropwise at room temperature.

The reaction mixture was stirred for an additional 30 minutes, then n-pentane (2.34 L) was added to the solution. After 30 minutes, the reaction mixture was filtered and a part of the wet material was dried at 40-45° C. in a vacuum oven. Both the wet sample and the dried material proved to be Form M2.

What is claimed is:

1. A crystalline mycophenolate sodium selected from the group consisting of a crystalline mycophenolate sodium form (M4) characterized by a powder XRD pattern with peaks at 7.1, 7.6, 10.7, 14.0 and 16.3±0.2 degrees 2-theta; a crystalline mycophenolate sodium form (Form M5) characterized by a powder XRD pattern with peaks at 9.8, 17.4, 22.2, 27.1, and 31.7±0.2 degrees 2-theta; a crystalline mycophenolate sodium form (Form M6) characterized by a powder XRD pattern with peaks at 6.1, 7.9, 14.6, 18.2 and 18.5±0.2 degrees 2-theta; a crystalline mycophenolate sodium form (Form M7) characterized by a powder XRD pattern with peaks at 13.0, 13.7, 17.6, 22.6, and 23.6±0.2 degrees 2-theta; a crystalline mycophenolate sodium form (Form M8) characterized by a powder XRD pattern with peaks at 5.4, 7.5, 9.8, 10.6, 18.2 and 20.9±0.2 degrees 2-theta; a crystalline mycophenolate sodium form (Form M9) characterized by a powder XRD pattern with peaks at 5.6, 6.0, 7.5 and 9.9±0.2 degrees 2-theta; a crystalline mycophenolate sodium form (Form M10) characterized by a powder XRD pattern with peaks at 5.8, 9.0, 9.3, and 19.7±0.2 degrees 2-theta; a crystalline mycophenolate sodium form (Form M11) characterized by a powder XRD pattern with peaks at 10.3, 4.7, 5.3, 6.5, 8.2, 9.9, 15.5 and 19.1±0.2 degrees 2-theta and amorphous mycophenolate sodium form (Form M12) characterized by an FTIR spectrum with peaks at 1735, 1560 and 1133 cm$^{-1}$.

2. Mycophenolate sodium acetone solvate having an acetone content from about 14% to about 18%.

3. Mycophenolate sodium acetonitrile solvate having an acetonitrile content from about 9.5% to about 11.5%.

4. A crystalline mycophenolate sodium selected from the group consisting of a crystalline mycophenolate sodium form (Form M3) characterized by a powder XRD pattern with peaks at 6.0, 9.3, 15.5, and 18.4±0.2 degrees 2 theta; a crystalline mycophenolate sodium form (Form M15) characterized by a powder XRD pattern with peaks at 9.9, 13.1, 14.1, 16.1, 17.7, 18.5, 19.6, and 23.8±0.2 degrees 2-theta; a crystalline mycophenolate sodium form (Form M16) characterized by a powder XRD pattern with peaks at 5.2, 5.5, 8.1, 11.0, 16.1, 16.6, 17.3, and 22.0±0.2 degrees 2-theta; a crystalline mycophenolate sodium form (Form M17) characterized by a powder XRD pattern with peaks at 5.5, 7.7, 8.1, 9.8, 10.7, 11.0, 16.5, 22.0, and 26.0±0.2 degrees 2-theta; a crystalline mycophenolate sodium form (Form M18) characterized by a powder XRD pattern with peaks at 5.6, 8.1, 9.9, 10.8, 13.7, 16.6, 19.1, and 22.1±0.2 degrees 2-theta; a crystalline mycophenolate sodium form (Form M19) characterized by a powder XRD pattern with peaks at 7.6, 8.3, 10.7, 11.7, 15.9, 18.2, 21.0, and 21.6±0.2 degrees 2-theta; a crystalline mycophenolate sodium form (Form M20) characterized by a powder XRD pattern with peaks at 5.1, 5.5, 6.7, 10.0, 10.9, 13.1, 14.6, 17.3, and 24.8±0.2 degrees 2-theta; a crystalline mycophenolate sodium form (Form M21) characterized by a powder XRD pattern with peaks at 5.4, 6.2, 7.9, 8.7, 8.9, 16.8, 20.0, and 25.2±0.2 degrees 2-theta; a crystalline mycophenolate sodium form (Form M22) characterized by a powder XRD pattern with peaks at 3.8, 4.7, 5.3, 6.6, 8.1, 9.8, 10.6, 11.1, 15.5, and 23.3±0.2 degrees 2-theta; a crystalline mycophenolate sodium form (Form M26) characterized by a powder XRD pattern with peaks at 5.8, 9.2, 9.5, 10.0, 13.4, 13.7, 15.8, 17.6, 23.6, and 24.1±0.2 degrees 2-theta; a crystalline mycophenolate sodium form (Form M27) characterized by a powder XRD pattern with peaks at 6.2, 9.4, 12.6, 13.1, 13.7, 14.0, 15.9, 17.5, and 24.1±0.2 degrees 2-theta; and a crystalline mycophenolate sodium form (Form M28) characterized by a powder XRD pattern peaks at 7.7, 8.5, 9.9, 12.3, 16.0, 21.4, 23.2, and 26.0±0.2 degrees 2-theta.

* * * * *

UNITED STATES PATENT AND TRADEMARK OFFICE
CERTIFICATE OF CORRECTION

PATENT NO. : 7,439,373 B2 Page 1 of 1
APPLICATION NO. : 11/186560
DATED : October 21, 2008
INVENTOR(S) : Molnar et al.

It is certified that error appears in the above-identified patent and that said Letters Patent is hereby corrected as shown below:

Column 35
Line 9, change "(M4)" to --(Form M4)--

Column 36
Line 34, change "pattern peaks at" to --pattern with peaks at--

Signed and Sealed this

Twentieth Day of October, 2009

David J. Kappos
*Director of the United States Patent and Trademark Office*